US007744896B1

(12) United States Patent
Ensoli

(10) Patent No.: US 7,744,896 B1
(45) Date of Patent: Jun. 29, 2010

(54) HIV-1 TAT COMPOSITIONS

(75) Inventor: Barbara Ensoli, Rome (IT)

(73) Assignee: Istituto Superiore di Sanita', Rome (IT)

(*) Notice: Subject to any disclaimer, the term of this patent is extended or adjusted under 35 U.S.C. 154(b) by 0 days.

(21) Appl. No.: 09/555,534

(22) PCT Filed: Nov. 30, 1998

(86) PCT No.: PCT/EP98/07721

§ 371 (c)(1),
(2), (4) Date: Jul. 31, 2000

(87) PCT Pub. No.: WO99/27958

PCT Pub. Date: Jun. 6, 1999

(30) Foreign Application Priority Data

Dec. 1, 1997 (IT) ............................ RM97A0743

(51) Int. Cl.
*A61K 39/38* (2006.01)
*A61K 39/12* (2006.01)
*A61K 39/21* (2006.01)
*C07H 21/04* (2006.01)
*C12N 15/09* (2006.01)

(52) U.S. Cl. ............... 424/188.1; 424/184.1; 424/185.1; 424/186.1; 424/187.1; 424/208.1; 536/23.72; 435/69.3

(58) Field of Classification Search ................. 530/350, 530/324, 826; 424/188.1, 208.1
See application file for complete search history.

(56) References Cited

U.S. PATENT DOCUMENTS 5,646,120 A * 7/1997 Sumner-Smith et al. ...... 514/14
5,652,122 A * 7/1997 Frankel et al. ............. 435/69.7

FOREIGN PATENT DOCUMENTS

| WO | WO9403596 | 2/1994 |
| WO | WO9415634 | 7/1994 |
| WO | WO9531999 | 11/1995 |
| WO | 87/02989 | * 5/1997 |
| WO | WO9817309 | 4/1998 |

OTHER PUBLICATIONS

Riffkin et al. "A single amino-acid change between the antigenically different extracellular serine proteases V2 and B2 from *Dichelobacter nodosus*", Gene, vol. 167 (1995), pp. 279-283.*
Abaza et al. "Effects of amino acid substitutions outside an antigenic site on protein binding to monoclonal antibodies of predetermined specificity obtained by peptide immunization", *Journal of Protein Chemistry*, vol. 11, No. 5 (1992), pp. 433-444.*
Cruse et al. *Illustrated Dictionary of Immunology* (Boca Raton, FL, CRC Press, Inc., 1995), p. 309. QR180.4.C78.*

Paul, *Fundamental Immunology*, (Philadelphia & New York, Lippincott-Raven Publishers, 1993), pp. 250 and 1311-1312. QR181.F84.*
Cafaro et al. "Control of SHIV 89.6P infection of cynomolgus monkeys by HIV 1 Tat protein vaccine" Nature Medicine, vol. 5, No. 6(Jun. 1999), pp. 643-650.*
Feinberg et al. "AIDS vaccine models: Challenging challenge viruses" Nature Medicine, vol. 8, No. 3(Mar. 2002), pp. 207-210.*
Chang et al. "HIV-1 Tat protein exits from cells via a leaderless secretory pathway and binds to extracellular matrix-associated heparan sulfate proteoglycans through its basic region", AIDS, vol. 11, No. 12 (Oct. 11, 1997), p. 1421-1431.*
Chengalvala et al. "Enhanced immunogenicity of hepatitis B surface antigen by insertion of a helper T cell epitope from tetanus toxoid", Vaccine, vol. 17, Nos. 9-10(Mar. 5, 1999) pp. 1035-1041.*
Heiman et al. "HIV Vaccines: Where are we Going?" Nature Medicine Vaccine Supplement (May 1998) reproduced by the NIAID Division of AIDS at http://www.niaid.nih.gov/daids/vaccine/1998nature.htm.*
Vogel, F.R., Powell, M.F., 1995. A compendium of vaccine adjuvants and excipients. In: Powell, M.F., Newman, M.J. (Eds.), Vaccine Design. The Subunit and Adjuvant Approach. Plenum, New York, pp. 1, 9, 10, 51, and 52.*
Hengge et al. "Randomized, controlled phase II trial of subcutaneous interleukin-2 in combination with highly active antiretroviral therapy (HAART) in HIV patients", AIDS, vol. 12, No. 17(Nov. 1998), pp. F225-F234.*
Castignolles et al. "A new family of carriers (biovectors) enhances the immunogenicity of rabies antigens", Vaccine, vol. 14, No. 14(Oct. 1996) pp. 1353-1360.*
Ramshaw et al. "Enhanced antibody responses to antigens presented on autologous erythrocytes", Journal of immunological methods, vol. 18, Nos. 3-4,(1977) pp. 251-255. Abstract Only.*

(Continued)

*Primary Examiner*—Robert B Mondesi
*Assistant Examiner*—Louise Humphrey
(74) *Attorney, Agent, or Firm*—Jones Day

(57) ABSTRACT

The present invention refers to Tat as the active principle for a prophylactic and/or therapeutic vaccine against HIV infection, the progression towards AIDS and the development of tumors and other syndromes and symptoms in subjects infected by HIV. Tat is in biologically active form either as recombinant protein or peptide or as DNA. More particularly, the invention refers to a vaccine based on HIV-1 Tat as immunogen, inoculated as DNA and/or recombinant protein or as peptides, alone or in combination with other genes or viral gene products (Nef, Rev, Gag) or parts thereof, or in combination with various immuno modulant cytokines (IL-12, IL-15) or with the gene coding for an immuno modulant cytokine or part thereof. Tat, Nef, Rev, Gag and the immuno modulant cytokines are administrated both as a mixture of recombinant proteins, peptides or fusion proteins (Tat/Nef, Tat/Rev, Tat/Gag, Tat/IL-12, Tat/IL-15) or as plasmid DNA.

83 Claims, 17 Drawing Sheets

OTHER PUBLICATIONS

Livingston et al. "The hepatitis B virus-specific CTL responses induced in humans by lipopeptide vaccination are comparable to those elicited by acute viral infection", Journal of Immunology, vol. 159, No. 3 (Aug. 1, 1997), pp. 1383-1392.*

Barry et al. "Protease inhibitors in patients with HIV disease. Clinically important pharmacokinetic considerations", Clinical Pharmacokinetics, vol. 32, No. 3 (Mar. 1997), pp. 194-209.*

Ramshaw et al. "Enhanced antibody responses to antigens presented on autologous erythrocytes", Journal of Immunological Methods, vol. 18, Nos. 3-4,(1977) pp. 251-255. Complete reference.*

Naryshkin et al. RNA recognition and regulation of HIV-1 gene expression by viral factor Tat. Biochemistry (Mosc) May, 1998 vol. 63(5), pp. 489-503. Abstract only.*

Campbell et al. The C Terminus of HIV-1 Tat Modulates the Extent of CD178-mediated Apoptosis of T Cells. The Journal of Biological Chemistry. Nov. 18, 2005. vol. 280, No. 46, pp. 38376-38382.*

Martinez-Picado. HIV-1 Drug Resistance Assays in Clinical Management. AIDS Clinical Care Nov. 1998, vol. 10 No. 11, pp. 81-88.*

Kusumi et al. Human Immunodeficiency Virus Type 1 Envelope Gene Structure and Diversity in Vivo and after Cocultivation in Vitro. Journal of Virology, Feb. 1992, vol. 66, No. 2, pp. 875-885.*

Meyerhans et al. Temporal fluctuations in HIV quasispecies in vivo are not reflected by sequential HIV isolations. Cell 1989 Sep. 8, vol. 58(5), pp. 901-910. Abstract only.*

Altman et al. HIV escape: there and back again. Nature Medicine Mar. 2004, vol. 10, No. 3, pp. 229-230.*

Desrosiers. Prospects for an AIDS vaccine. Nature Medicine Mar. 2004, vol. 10, No. 3, pp. 221-223.*

Leslie et al. HIV evolution: CTL escape mutation and reversion after transmission. Nature Medicine Mar. 2004, vol. 10, No. 3, pp. 282-289.*

Friedrich et al. Reversion of CTL escape-variant immunodeficiency viruses in vivo. Nature Medicine Mar. 2004, vol. 10, No. 3, pp. 275-281.*

Gu et al. Phase separation of acetonitrile—water mixture in protein purification. Separation Techonology, Oct. 1994, vol. 4, pp. 258-260.*

Kim et al., "Introduction of Soluble Proteins into the MHC Class I Pathway by Conjugation to an HIV tat Peptide", *The Journal of Immunology*, 1997, 159: 1666-1668.

Hinkula et al., "Nucleic Acid Vaccination with HIV Regulatory Genes: A Combination of HIV-1 Genes in Separate Plasmids Induces Strong Immune Responses", *Vaccine* 1997, vol. 15, No. 8.

Hinkula et al., "Recognition of Prominent Viral Epitopes Induced by Immunization with Human Immunodeficiency Virus Type 1 Regulatory Genes", *Journal of Virology*, Jul. 1997, pp. 5528-5539.

Samaniego, "Inflammatory Cytokines Induce Endothelial Cells to Produce and Release Basic Fibroblast Growth Factor and to Promote Karposi's Sarcoma-Like Lesions in Nude Mice", *Immunology*, 1997, 158: 1887-1894.

Allen et al., 2002, "Tat-Vaccinated Macaques Do Not Control Simian Immunodeficiency Virus SIVmac239 Replication," *J. Virology*, 76(8): 4108-4112.

Cafaro et al., 2000, "SHIV89.6P pathogenicity in cynomolgus monkeys and control of viral replication and disease onset by human immunodeficiency virus type 1 Tat vaccine," *J. Med. Primatol.*, 29: 193-208.

Calarota et al., 1999, "Immune Responses in Asymptomatic HIV-1-Infected Patients After HIV-DNA Immunization Followed by Highly Active Antiretroviral Treatment," *J. Immunology*, 163(4): 2330-2338.

Calarota et al., 1998, "Cellular cytotoxic response induced by DNA vaccination in HIV-1-infected patients," *The Lancet*, 351:1320-1325.

Fanales-Belasio et al., 2002, "HIV-1 Tat-Based Vaccines: From Basic Science to Clinical Trials," *DNA and Cell Biology*, 21(9): 599-610.

Frankel et al., 1988, "Tat Protein from Human Immunodeficiency Virus Forms a Me0Otal-Linked Dimer," *Science*, 240 (4848):70-73.

Johnston, Margaret, 2000, "The role of nonhuman primate models in AIDS vaccine development," *Molecular Medicine Today*, 6:267-270.

Lu, Yichen, 1997, "HIV-1 Vaccine Candidate Evaluation in Non-Human Primates," *Critical Reviews in Oncogenesis*, 8(2&3):273-291.

McMichael, Andrew and Rowland-Jones, Sarah, 2001, "Cellular immune responses to HIV," *Nature*, 410:980-987.

Nath et al., 2000, "The chimpanzee and other non-human-primate models in HIV-1 vaccine research," *Trends Microbiol,.* 8(9):426-431.

Silvera et al., 2002, "Outcome of Simian—Human Immmunodeficiency Virus Strain 89.6p Challenge following Vaccination of Rhesus Macaques with Human Immunodeficiency Virus Tat Protein," *J. Virology*, 76(8): 3800-3809.

Stott, et al., 1998, "Candidate Vaccines Protect Macaques against Primate Immunodeficiency Viruses," *AIDS Research and Human Retroviruses*, 14(Supp. 3): S-265-S-270.

Wang, et al., 2002, "Comprehensive Analyses of a Unique HIV-1-Infected Nonprogressor Reveal a Complex Association of Immunobiological Mechanisms in the Context of Replication-Incompetent Infection," *Virology*, 304: 246-264.

Ahmed et al., Studies on the mechanism of acetonitrile toxicity. I: Whole body autoradiographic distribution and macromolecular interaction of 2-14C-acetonitrile in mice. Pharmacol Toxicol. May 1992;70(5 Pt 1):322-30.

Bohan et al., Analysis of Tat transactivation of human immunodeficiency virus transcription in vitro. Gene Expr. 1992;2(4):391-407.

Michael E. Byrnes, Methods in Molecular Biology, vol. 32: Basic Protein and Peptide Protocols, Chapter 4, p. 42, Edited by B.M. Dunn and M.W. Pennington, 1994, Humana Press Inc.

Ensoli et al., Release, uptake, and effects of extracellular human immunodeficiency virus type I Tat protein on cell growth and viral transactivation. J Virol. Jan. 1996;67(1):277-87.

Gomez-Cambronero et al. Actions of the protease inhibitor phenylmethylsulfonyl fluoride on neutrophil granule enzyme secretion and superoxide production induced by fMet-Leu-Phe and phorbol 12-myristate-13-acetate. Int Arch Allergy Appl Immunol. 1989;89(4):362-8.

Jan-Chister Janson and Lars Rydén in Protein Purification, Chapter 1, pp. 16-18. Edited by VCH Publishers Inc., 1989.

Lotti et al., Promotion of organophosphate—induced delayed polyneuropathy by phenylmethanesulfonyl fluoride. Toxicol Appl Pharmacol. Apr. 1991;108(2):234-41.

Massicotte et al., Neuropathologic effects of phenylmethylsulfonyl fluoride (PMSF)-induced promotion and protection in organophosphorus ester-induced delayed neuropathy (OPIDN) in hens. Neurotoxicology. Oct. 1999;20(5):749-59.

Robles et al., 2005, Acetonitrile, in *Encyclopedia of Toxicology, Second Edition*, (Wexler, ed.) Elsevier, Philadelphia. PA, pp. 28-30.

Paul C. Sadek, The HPLC Solvent Guide, Chapter 7, Section 7.6.4 on p. 251, 1996, John Wiley & Sons, Inc.

Chris Shaw, Methods in Molecular Biology, vol. 32: Basic Protein and Peptide Protocols, Chapter 31, p. 275.6[th] sentence under Introduction, Edited by J.M. Walker, 1994, Humana Press Inc.

Toxsys database Record No. AL7700000 for Acetonitrile.

Toxsys database Record No. AJ9625000 for Acetic acid, trifluoro.

Istituto Superiore di Sanitá, "Comunicato Stampa N° 06/05," Jul. 5, 2005.

Linn S., "Strategies and considerations for protein purifications," Methods Enzymol. 1990;182:9-15.

McGrath et al., "Production of crystallizable human chymase from a *Bacillus subtilis* system," FEBS Lett. Aug. 25, 1997;413(3):486-8.

James et al., "Purification and biochemical characterization of a vacuolar serine endopeptidase induced by glucose starvation in maize roots," Biochem J. Nov. 15, 1996;320 (Pt 1):283-92.

Goldberg et al., "Proteases in *Escherichia coli*," Methods Enzymol. 1981;80 Pt C:680-702.

Pirrotta et al., "General purification schemes for restriction endonucleases," Methods Enzymol. 1980;65(1):89-95.

Goldstein G., "HIV-1 Tat protein as a potential AIDS vaccine," Nat Med. Sep. 1996;2(9):960-4.

Takacs et al., "Purification of clinical grade proteins produced by recombinant DNA technologies," J Immunol Methods. Oct 25, 1991;143(2):231-40.

Voet et al., Biochemistry, 2nd Edition, 1995, John Wiley & Sons, Inc., p. 73.

Buanec et al., "A prophylactic and therapeutic AIDS vaccine containing as a component the innocuous Tat toxoid," Biomedicine and Pharmacotherapy, 1998;52(10):431-435.

Buonaguro et al., "Effects of the human immunodeficiency virus type 1 Tat protein on the expression of inflammatory cytokines," Journal of Virology, Dec. 1992;66(12):7159-7167.

Chen et al., "The Tat protein of HIV-1 induces tumor necrosis factor-αproduction. Implications for HIV-1-associated neurological diseases," Journal of Biological Chemistry, Sep. 5, 1997;272(36):22385-22388.

Chirmule et al., "Human immunodeficiency virus Tat induces functional unresponsiveness in T cells," Journal of Virology. Jan 1995;69(1):492-498.

Conant et al., "Extracellular human immunodeficiency virus type 1 Tat protein is associated with an increase in both NF-kappa B binding and protein kinase C activity in primary human astrocytes," Journal of Virology, Mar. 1996;70(3):1384-1389.

Ehret et al. "Resistance of chimpanzee T cells to human immunodeficiency virus type 1 Tat-enhanced oxidative stress and apoptosis." Journal of Virology, Sep. 1996;70(9):6502-6507.

Ensoli et al., "Tat protein of HIV-1 stimulates growth of cells derived from Kaposi's sarcoma lesions of AIDS patients," Nature, May 3, 1990;345(6270):84-86.

Ensoli et al., "Synergy between basic fibroblast growth factor and HIV-1 Tat protein in induction of Kaposi's sarcoma," Nature, Oct. 20, 1994;371(6499):674-680.

Frankel et al., "Tat protein from human immunodeficiency virus forms a metal-linked dimer." Science. Apr. 1, 1988;240(4848):70-73.

Frankel et al.. "Cellular uptake of the tat protein from human immunodeficiency virus." Cell. Dec. 23, 1988 ;55(6):1189-1193.

Gallo, "Tat as one key to HIV-induced immune pathogenesis and Tat (correction of Pat) toxoid as an important component of a vaccine," Proceedings of the National Academy of Sciences of the United States of America, Jul. 20, 1999;96(15):8324-8326.

Gentz et al. "Bioassay for trans-activation using purified human immunodeficiency virus tat-encoded protein: trans-activation requires mRNA synthesis," Proceedings of the National Academy of Sciences of the United States of America, Feb. 1989;86(3):821-824.

Gibellini et al., "Tat-expressing Jurkat cells show an increased resistance to different apoptotic stimuli, including acute human immunodeficiency virus-type 1 (HIV-1) infection," British Journal of Haematology, Jan. 1995;89(1):24-33.

Gibellini et al., "Upregulation of c-Fos in activated T lymphoid and monocytic cells by human immunodeficiency virus-1 Tat protein," Blood, Mar. 1, 1997;89(5):1654-1664.

Gringeri et al., "Safety and immunogenicity of HIV-1 Tat toxoid in immunocompromised HIV-1-infected patients," Journal of Human Virology, May-Jun. 1, 1998;(4):293-298.

Gringeri et al., "Tat toxoid as a component of a preventive vaccine in seronegative subjects," Journal of Acquired Immune Deficiency Syndromes and Human Retroviology, 1999 Apr. 1, 199;20(4):371-375.

Hayman et al., "Neurotoxicity of peptide analogues of the transactivating protein tat from Maedi-Visna virus and human immunodeficiency virus," Neuroscience, Mar. 1993;53(1):1-6.

Huang et al., "Human immunodeficiency virus type 1 Tat protein activates B lymphocytes," Biochemical and Biophysical Research Communications, 1997 Aug. 18, 1997;237(2):461-464.

James, "Biological treatment approaches, including Tat toxoid vaccine: interview with Robert Gallo, M.D.," AIDS Treatment News, Sept. 17, 1999;327:1-5.

Katsikis et al., "HIV type 1 Tat protein enhances activation—but not Fas (CD95)-induced peripheral blood T cell apoptosis in healthy individuals," International Immunology, Jun. 1997;9(6):835-841.

Kolesnitchenko et al. "A major human immunodeficiency virus type 1-initiated killing pathway distinct from apoptosis." Journal of Virology, Dec. 1997;71( 12):9753-9763.

Kolson et al., "HIV-1 Tat alters normal organization of neurons and astrocytes in primary rodent brain cell cultures: RGD sequence dependence," AIDS Research and Human Retroviruses, 1993 Jul;9(7):677-685.

Lafrenie et al., "HIV-1-Tat protein promotes chemotaxis and invasive behavior by monocytes," Journal of Immunology, Aug. 1, 1996 ;157(3):974-977.

Li et al., "Induction of apoptosis in uninfected lymphocytes by HIV-1 Tat protein," Science, Apr. 21, 1995; 268(5209):429-431.

Li et al., "Tat protein induces self-perpetuating permissivity for productive HIV-1 infection," Proceedings of the National Academy of Sciences of the United States of America, Jul. 22, 1997;94( 15):8116-8120.

Ma et al., "Molecular determinants for cellular uptake of Tat protein of human immunodeficiency virus type 1 in brain cells," Journal of Virology, Mar. 1997;71(3):2495-2499.

Magnuson et al., "Human immunodeficiency virus type 1 tat activates non-N-methyl-D-aspartate excitatory amino acid receptors and causes neurotoxicity," Annals of Neurology, Mar. 1995;37(3):373-380.

McCloskey et al., "Dual role of HIV Tat in regulation of apoptosis in T cells," Journal of Immunology, Jan. 15, 1997;158(2):1014-1019.

Nath et al., "Identification of a human immunodeficiency virus type 1 Tat epitope that is neuroexcitatory and neurotoxic," Journal of Virology, Mar. 1996;70(3):1475-1480.

New et al., "Human immunodeficiency virus type 1 Tat protein induces death by apoptosis in primary human neuron cultures," Journal of NeuroVirology, Apr. 3, 1997;3(2):168-173.

Orsini et al., "Extracellular human immunodeficiency virus type 1 Tat protein promotes aggregation and adhesion of cerebellar neurons," Journal of Neuroscience, Apr. 15, 1996;16(8):2546-2552.

Orsini et al., "Purification and functional characterization of wild-type and mutant HIV-1 and HIV-2 Tat proteins expressed in *Escherichia coli*," Protein Expression and Purification, Sep. 8, 1996;(2):238-246.

Orsini et al., "Inhibition of human immunodeficiency virus type 1 and type 2 Tat function by transdominant Tat protein localized to both the nucleus and cytoplasm," Journal of Virology, Nov. 1996;70(11):8055-8063.

Ott et al., "Immune hyperactivation of HIV-1-infected T cells mediated by Tat and the CD28 pathway," Science, Mar. 7, 1997;275(5305):1481-1485.

Philippon et al., "The basic domain of the lentiviral Tat protein is responsible for damages in mouse brain: involvement of cytokines," Virology. Dec. 1994;205(2):519-529.

Purvis et al., "HIV type 1 Tat protein induces apoptosis and death in Jurkat cells," AIDS Research and Human Retroviruses. 1995 Apr. 11, 1995(4):443-450.

Re et al., "Effect of antibody to HIV-1 Tat protein on viral replication in vitro and progression of HIV-1 disease in vivo," Journal of Acquired Immune Deficiency Syndromes and Human Retrovirology. Dec. 1, 1995 ;10(4):408- 416.

Sabatier et al., "Evidence for neurotoxic activity of tat from human immunodeficiency virus type 1," Journal of Virology. Feb. 1991;65(2):961-967.

Tonelli, "AIDS, a vaccine [which allows] to hope—Announcement made at the San Marino Conference, in front of an international audience of scientists: 5 macaques out of 7 did not develop HIV. "We strike at the heart the protein which allows the virus to replicate" Fight Against AIDS," La Repubblica, Oct. 24, 1998 p. 10 (with English translation).

Viscidi et al., "Inhibition of antigen-induced lymphocyte proliferation by Tat protein from HIV-1," Science, Dec. 22, 1989;246(4937):1606-1608.

Weeks et al., "Neurotoxicity of the human immunodeficiency virus type 1 tat transactivator to PC12 cells requires the Tat amino acid 49-58 basic domain," Journal of Neuroscience Research, Sep. 1, 1995;42(1):34-40.

Westendorp et al., "HIV-1 Tat potentiates TNF-induced NF-κB activation and cytotoxicity by altering the cellular redox state," the EMBO Journal, Feb. 1, 1995; 14(3):546-554.

Westendorp et al., "Sensitization of T cells to CD95-mediated apoptosis by HIV-1 Tat and gp120," Nature, Jun. 8, 1995;375(6531):497-500.

Wu et al. "Decreased ability of HIV-1 tat protein-treated accessory cells to organize cellular clusters is associated with partial activation of T cells." Proceedings of the National Academy of Sciences of the United States of America. Dec. 9, 1997;94(25):13832-13837.

Zagury et al., "A critical role of Tat and IFNα in the HIV-1 -induced immunosuppression leading to AIDS," Cellular Pharmacology, 1996;3:97-103.

Zauli et al., "Tat protein stimulates production of transforming growth factor-β 1 by marrow macrophages: a potential mechanism for human immunodeficiency virus-1-induced hematopoietic suppression," Blood, Dec. 15, 1992;80(12):3036-3043.

Zauli et al., "Human immunodeficiency virus type 1 Tat protein protects lymphoid, epithelial, and neuronal cell lines from death by apoptosis," Cancer Research, Oct. 1, 1993;53(19):4481-4485.

Zauli et al., "An autocrine loop of HIV type-1 Tat protein responsible for the improved survival/proliferation capacity of permanently Tat-transfected cells and required for optimal HIV-1 LTR transactivating activity," Journal of Acquired Immune Deficiency Syndromes and Human Retrovirology, Nov. 1, 1995;10(3):306-316.

Zauli et al., "The human immunodeficiency virus type-1 Tat protein upregulates Bcl-2 gene expression in Jurkat T-cell lines and primary peripheral blood mononuclear cells," Blood. Nov. 15, 1995 ;86(10):3823-3834.

Zauli et al., "The human immunodeficiency virus type-1 (HIV-1) Tat protein and Bcl-2 gene expression," Leukemia and Lymphoma, Nov. 23, 1996;23(5-6):551-560.

Agostini et al. Interleukin—15 triggers activation and growth of the CD8 T-cell pool in extravascular tissues of patients with acquired immunodeficiency syndrome. Blood. Aug. 1, 1997;91(3):1115-23.

Albini et al. Angiogenic properties of human immunodeficiency virus type 1 Tat protein. Proc Natl Acad Sci USA. May 23, 1995;92(11):4838-42.

Allan et al. A new HTLV-III/LAV encoded antigen detected by antibodies from AIDS patients. Science. Nov. 15, 1985;230(4727):810-3.

Harlow et al, Eds., *Antibodies—A Laboratory Manual*, Cold Spring Harbor Laboratory, 1988.

Arya et al. Trans-activator gene of human T-lymphotropic virus type III (HTLV-III). Science. Jul. 5, 1985;229(4708):69-73.

Ariyoshi et al. HIV-2-specific cytotoxic T-lymphocyte activity is inversely related to proviral load. AIDS. Jun. 9, 1995;(6):555-9.

Audibert and Lise, Adjuvants: current status, clinical perspectives and future prospects. Immunol Today. Jun. 14, 1993;(6):281-4.

Badolato et al. Interleukin-15 (IL-15) induces IL-8 and monocyte monocyte chemotactic protein 1 production in human monocytes. Blood. Oct. 1, 1997 ;90(7):2804-9.

Barillari et al. Effects of cytokines from activated immune cells on vascular cell growth and HIV-1 gene expression. Implications for AIDS-Kaposi's sarcoma pathogenesis. J Immunol. Dec. 1, 1992 ;149(11):3727-34.

Barillari et al. The Tat protein of human immunodeficiency virus type 1, a growth factor for AIDS Kaposi sarcoma and cytokine-activated vascular cells, induces adhesion of the same cell types by using integrin receptors recognizing the RGD amino acid sequence. Proc Natl Acad Sci U S A. Sep. 1, 1993;90(17):7941-5.

Blomberg and Ulfstedt, Fluorescent europium chelates as target cell markers in the assessment of natural killer cell cytotoxicity. J Immunol Methods. Mar. 15, 1993;160(1):27-34.

Blomberg K. Simultaneous measurement of natural killer cell cytotoxicity against each of three different target cell lines. J Immunol Methods. Feb. 10, 1994;168(2):267-73.

Blomberg et al. Time-resolved fluorometric assay for natural killer activity using target cells labelled with a fluorescence enhancing ligand. J Immunol Methods. Jun. 21, 1996;193(2):199-206.

Bohan et al. Analysis of Tat transactivation of human immunodeficiency virus transcription in vitro. Gene Expr. 1992;2(4):391-407.

Bourgault et al. Three epitopic peptides of the simian immunodeficiency virus Nef protein recognized by macaque cytolytic T lymphocytes. J Virol. Feb. 1992;66(2):750-6.

Boyer et al. Protection of chimpanzees from high-dose heterologous. HIV-1 challenge by DNA vaccination. Nat Med. May 3, 1997;(5):526-32.

Bruisten et al. Concordance of human immunodeficiency virus detection by polymerase chain reaction and by serologic assays in a Dutch cohort of seronegative homosexual men J Infect Dis. Sep. 1992;166(3):620-2.

Buseyne et al. Gag—specific cytotoxic T lymphocytes from human immunodeficiency virus type 1-infected individuals: Gag epitopes are clustered in three regions of the p24gag protein. J Virol. Feb. 1993;67(2):694-702.

Butera et al. Oscillation of the human immunodeficiency virus surface receptor is regulated by the state of viral activation in a CD4+ cell model of chronic infection. J Virol. Sep. 1991;65(9):4645-53.

Butera et al. Human immunodeficiency virus type 1 RNA expression by four chronically infected cell lines indicates multiple mechanisms of latency. J Virol. Apr. 1994;68(4):2726-30.

Cafaro et al. T-cell activation of HIV-infected mothers and their susceptible children. AIDS Res Hum Retroviruses. vol. 7, n.2: 204, 1991.

Carroll et al. Differential regulation of HIV-1 fusion cofactor expression by CD28 costimulation of CD4+ T cells. Science. Apr. 11, 1997;276(5310):273-6.

Carson et al. A potential role for interleukin-15 in the regulation of human natural killer cell survival. J Clin Invest. Mar. 1, 1997;99(5):937-43.

Chang et al. Regulation of Cellular Gene Expression and Function by the Human Immunodeficiency Virus Type 1 Tat Protein. J Biomed Sci. 1995 Aug. 2, 1995;(3):189-202.

Chang et al. HIV-1 Tat protein exits from cells via a leaderless secretory pathway and binds to extracellular matrix-associated heparan sulfate proteoglycans through its basic region. AIDS. Oct. 11, 1997;(12):1421-31.

Chavany et al. Adsorption of oligonucleotides onto polyisohexylcyanoacrylate nanoparticles protects them against nucleases and increases their cellular uptake. Pharm Res. Sep. 1994;11(9):1370-8.

Chen et al. Cytotoxic T lymphocytes do not appear to select for mutations in an immunodominant epitope of simian immunodeficiency virus gag. J Immunol. Dec. 15, 1992;149(12):4060-6.

Chiarantini et al. Red blood cells as delivery system for recombinant HSV-1 glycoprotein B: immunogenicity and protection in mice. Vaccine. Feb. 15, 1997;(3):276-80.

Chiarantini et al. AIDS vaccination studies using an ex vivo feline immunodeficiency virus model: homologous erythrocytes as a delivery system for preferential immunization with putative protective antigens. Clin Diagn Lab Immunol. Mar. 1998 5(2):235-41.

Chirmule et al. Human immunodeficiency virus Tat induces functional unresponsiveness in T cells. J Virol. Jan. 1995;69(1):492-8.

Choppin et al. HLA-binding regions of HIV-1 proteins. I. Detection of seven HLA binding regions in the HIV-1 Nef protein. J Immunol. Jul. 15, 1991;147(2):569-74.

Corallini et al. Systemic expression of HIV-1 tat gene in transgenic mice induces endothelial proliferation and tumors of different histotypes. Cancer Res. Nov. 15, 1993;53(22):5569-75.

Culmann et al.. Six epitopes reacting with human cytotoxic CD8+ T cells in the central region of the HIV-1 Nef protein. J Immunol. Mar. 1, 1991;146(5):1560-5.

Couillin et al. Impaired cytotoxic T lymphocyte recognition due to genetic variations in the main immunogenic region of the human immunodeficiency virus 1 NEF protein. J Exp Med. Sep. 1, 1994;180(3):1129-34.

Danko and Wolff. Direct gene transfer into muscle. Vaccine. Dec. 1994;12(16):1499-502.

Di Fabio et al. Vaginal immunization of Cynomolgus monkeys with *Streptococcus gordonii* expressing HIV-1 and HPV 16 antigens. Vaccine. Mar. 1998;16(5):485-92.

Ensoli et al., IV International Conference on AIDS, Stockholm, 3087:241 (1988).

Ensoli et al. Tat protein of HIV-1 stimulates growth of cells derived from Kaposi's sarcoma lesions of AIDS patients. Nature. May 3, 1990;345(6270):84-6.

Ensoli et al. Release, uptake, and effects of extracellular human immunodeficiency virus type 1 Tat protein on cell growth and viral transactivation. J Virol. Jan. 1993;67(1):277-87.

Ensoli et al. Synergy between basic fibroblast growth factor and HIV-1 Tat protein in induction of Kaposi's sarcoma. Nature. Oct. 20, 1994;371(6499):674-80.

Ensoli et al., *AIDS Updates*, Eds. V. De Vita Jr., Hellman S., Rosenberg S.A., Lippincott J. B., 7:1 (1994), Philadelphia.

Felber et al. rev protein of human immunodeficiency virus type 1 affects the stability and transport of the viral mRNA. Proc Natl Acad Sci U S A. Mar. 1989 ;86(5):1495-9.

Fine and Dingman, Hypersensitivity dermatitis following suction-assisted lipectomy: A complication of local anesthetic. Ann Plast Surg. Jun. 1988;20(6):573-5.

Fiorelli et al. Cytokines from activated T cells induce normal endothelial cells to acquire the phenotypic and functional features of AIDS-Kaposi's sarcoma spindle cells. J Clin Invest. Apr. 1995;95(4):1723-34.

Folks et al. Cytokine—induced expression of HIV-1 in a chronically infected promonocyte cell line. Science. Nov. 6, 1987;238(4828):800-2.

Franchini et al. Cytoplasmic localization of the HTLV-III 3'orf protein in cultured T cells. Virology. Dec. 1986;155(2):593-9.

Frankel and Pabo, Cellular uptake of the tat protein from human immunodeficiency virus. Cell. Dec. 23, 1988;55(6):1189-93.

Fugier-Vivier et al. Measles virus suppresses cell-mediated immunity by interfering with the survival and functions of dendritic and T cells. J Exp Med. Sep. 15, 1997;186(6):813-23.

Gait MJ, Karu J: RNA recognition by the human immunodeficiency virus Tat and Rev proteins. Trends Biochem Sci 1993;18:255-259.

Glorioso et al. Development and application of herpes simplex virus vectors for human gene therapy. Annu Rev Microbiol. 1995;49:675-710.

Gombert et al. Antigenic epitopes of NEF proteins from differen HIV-1 strains as recognized by sera from patients with manifest and latent HIV infection. Virology. Jun. 1990;176(2) 458-66.

Goletti et al. Effect of cellular differentiation on cytokine-induced expression of human immunodeficiency virus in chronically infected promonocytic cells: dissociation of cellular differentiation and viral expression. J Virol. Apr. 1995;69(4):2540-6.

Gorman et al. Recombinant genomes which express chloramphenicol acetyltransferase in mammalian cells. Mol Cell Biol. Sep. 1982;2(9):1044-51.

Grabstein et al. Cloning of a T cell growth factor that interacts with the beta chain of the interleukin-2 receptor. Science. May 13, 1994;264(5161):965-8.

Grosjean et al. Measles virus infects human dendritic cells and blocks their allostimulatory properties for CD4+ T cells. J Exp Med. Sep. 15, 1997;186(6):801-12.

Guy et al. HIV F/3' orf encodes a phosphorylated GTP-binding protein resembling an oncogene product. Nature. Nov 19-25, 1987;330(6145):266-9.

Harrer et al. Strong cytotoxic T cell and weak neutralizing antibody responses in a subset of persons with stable nonprogressing HIV type 1 infection. AIDS Res Hum Retroviruses. May 1, 1996;12(7):585-92.

Harrich et al. Tat is required for efficient HIV-1 reverse transcription. EMBO J. Mar. 17, 1997;16(6):1224-35.

Hinkula et al. Recognition of prominent viral epitopes induced by immunization with human immunodeficiency virus type 1 regulatory genes. J Virol. Jul. 1997;71(7):5528-39.

Haneberg et al. Induction of specific immunoglobulin A in the small intestine, colon-rectum, and vagina measured by a new method for collection of secretions from local mucosal surfaces. Infect Immun. Jan. 1994;62(1):15-23.

Huang et al. Human immunodeficiency viruses regulated by alternative trans-activators: genetic evidence for a novel non-transcriptional function of Tat in virion infectivity. EMBO J. Jun. 15, 1994;13(12):2886-96.

Huard et al. Herpes simplex virus type 1 vector mediated gene transfer to muscle. Gene Ther. Aug. 1995;2(6):385-92.

Igarashi et al. Persistent infection with SIVmac chimeric virus having tat, rev, vpu, env and nef of HIV type 1 in macaque monkeys. AIDS Res Hum Retroviruses. Aug. 1994;10(8):1021-9.

Jonuleit et al. Induction of IL-15 messenger RNA and protein in human blood-derived dendritic cells: A role for IL-15 in attraction of T cells. J Immunol. Mar. 15, 1997;158(6):2610-5.

Jullien et al.. IL-15, an immunomodulator of T cell responses in intracellular infection. J Immunol. Jan. 15, 1997;158(2):800-6.

Kanai et al. IL-15 stimulates the expansion of AIDS virus-specific CTL. J Immunol. Oct. 15, 1996;157(8):3681-7.

Karlsson et al. Characterization of molecularly cloned simian-human immunodeficiency viruses causing rapid CD4+ lymphocyte depletion in rhesus monkeys. J Virol. Jun. 1997;71(6):4218-25.

Kashanchi et al. Interaction of human immunodeficiency virus type 1 Tat with a unique site of TFIID inhibits negative cofactor Dr1 and stabilizes the TFIID-TFIIA complex. J Virol. Aug. 1996;70(8):5503-10.

Kestler et al. Induction of AIDS in rhesus monkeys by molecularly cloned simian immunodeficiency virus. Science. Jun. 1, 1990;248(4959):1109-12.

Kim et al. The HIV tat gene transforms human keratinocytes. Oncogene. Aug. 1992;7(8):1525-9.

Koup et al. Temporal association of cellular immune responses with the initial control of viremia in primary human immunodeficiency virus type 1 syndrome. J Virol. Jul. 1994;68(7):4650-5.

Krisky et al. Rapid method for construction of recombinant HSV gene transfer vectors. Gene Ther. Oct. 1997;4(10):1120-5.

Kuklin et al. Modulation of mucosal and systemic immunity by enteric administration of nonreplicating herpes simplex virus expressing cytokines. Virology. Jan. 20, 1998;240(2):245-53.

Pozzi et al., *Gram—Positive Bacteria as Vaccine vehicles for mucosal immunization*. Pozzi and Wells eds., Landes Austin, p. 107, (1997).

Lanzavecchia A. Identifying strategies for immune intervention. Science. May 14, 1993;260(5110):937-44.

Lasic, D. D., and D. Needham. The "stealth" liposome: a prototypical biomaterial. Chem Revs. 95:2601-2628 (1995).

M. Laus, C. Dinnella, M. Zannoni, G. Lanzarini, A. Casagrande. Functional Particles by Dispersion Polymerization 2: Synthesis and Characterization of Core Shell Microspheres. Polymer. 37:343 (1996).

Dinnella C., Laus M., Lanzarini G., Doria M. Functional particles by dispersion polymerization 4: Double shell tunable surface microspheres for selective enzyme adsorption. Polymers for Adv Techn. 7:548 (1996).

Lehner et al. Mucosal model of genital immunization in male rhesus macaques with a recombinant simian immunodeficiency virus p27 antigen. J Virol. Mar. 1994;68(3):162 -32.

Levine et al. Antiviral effect and ex vivo CD4+ T cell proliferation in HIV-positive patients as a result of CD28 costimulation. Science. Jun. 28, 1996;272(5270):1939-43.

Lewis et al., *Vaccine Protocol*. Robinson et al. Eds., Human Press, Totowa, New Jersey (1996).

Li et al. Tat protein induces self-perpetuating permissivity for productive HiV-1 infection. Proc Natl Acad Sci U S A. Jul. 22, 1997;94(15):8116-20.

Li et al. Infection of cynomolgus monkeys with a chimeric HIV-1/SIVmac virus that expresses the HIV-1 envelope glycoproteins. J Acquir Immune Defic Syndr. 1992;5(7):639-46.

Li et al. Induction of apoptosis in uninfected lymphocytes by HIV-1 Tat protein. Science. Apr. 21, 1995;268(5209):429-31.

Littaua et al. An HLA-C-restricted CD8+ cytotoxic T-lymphocyte clone recognizes a highly conserved epitope on human immunodeficiency virus type 1 gag. J Virol. Aug. 1991;65(8 ):4051-6.

Bengtsson and Sjolander, Adjuvant activity of iscoms; effect of ratio and co-incorporation of antigen and adjuvant. Vaccine. 1996 Jun;14(8):753-60.

Lu et al. Simian immunodeficiency virus DNA vaccine trial in macaques. J Virol. Jun. 1996;70(6):3978-91.

Lubaki et al. Characterization of a polyclonal cytolytic T lymphocyte response to human immunodeficiency virus in persons without clinical progression. J Infect Dis. Jun. 1997;175(6) 1360-7.

Lucey et al. In vitro immunologic and virologic effects of interleukin 15 on peripheral blood mononuclear cells from normal donors and human immunodeficiency virus type 1-infected patients. Clin Diagn Lab lmmunol. Jan. 1997;4(1):43-8.

Luciw et al. Persistent infection of rhesus macaques with T-cell-line-tropic and macrophage—tropic clones of simian/human immunodeficiency viruses (SHIV). Proc Natl Acad Sci U S A. Aug. 1, 1995;92(16):7490-4.

Magnani et al. Red blood cells as an antigen-delivery system. Biotechnol Appl Biochem. Oct. 1992;16(2):188-94.

Magnani et al. Preparation and characterization of biotinylated red blood cells. Biotechnol Appl Biochem. Dec. 1994;20 ( Pt 3):335-45.

Malim et al. The HIV-1 rev trans-activator acts through a structured target sequence to activate nuclear export of unspliced viral mRNA. Nature. Mar. 16, 1989;338(6212):254-7.

Mann and Frankel, Endocytosis and targeting of exogenous HIV-1 Tat protein. EMBO J. Jul. 1991; 10(7):1733-9.

Marconi et al. Replication—defective herpes simplex virus vectors for gene transfer in vivo. Proc Natl Acad Sci U S A. Oct. 15, 1996;93(21):11319-20.

Marcuzzi et al. Transcellular activation of the human immunodeficiency virus type 1 long terminal repeat in cocultured lymphocytes. J Virol. Jul. 1992;66(7):4228-32.

McLean et al. Protective vaccination against primary and recurrent disease caused by herpes simplex virus (HSV) type 2 using a genetically disabled HSV-1. J Infect Dis. Nov. 1994; 70(5):1100-9.

McLean et al. Induction of a protective immune response by mucosal vaccination with a DISC HSV-1 vaccine. Vaccine. 1996 Jul;1996;14(10):987-92.

McFarland et al. High frequency of Gag— and envelope—specific cytotoxic T lymphocyte precursors in children with vertically acquired human immunodeficiency virus type 1 infection, J Infect Dis. Oct. 1994;170(4):766-74.

Medaglini et al. Mucosal and systemic immune responses to a recombinant protein expressed on the surface of the oral commensal bacterium *Streptococcus gordonii* after oral colonization. Proc Natl Acad Sci U S A. Jul. 18, 1995;92(15):6868-72.

Medaglini et al. Commensal bacteria as vectors for mucosal vaccines against sexually transmitted diseases: vaginal colonization with recombinant streptococci induces local and systemic antibodies in mice. Vaccine. Aug.-Sep. 1997;15(12-13):1330-7.

Medaglini D, Ricci S, Maggi T, Rush CM, Manganelli R, Oggioni Mr, Pozzi G: Recombinant Gram—positive bacteria as vehicles of vaccine antigens. Biotechnol Annu Rev 1997, 3:297,312.

Medaglini et al. Vaginal immunization with recombinant gram—positive bacteria. Am J Reprod Immunol. Mar. 1998;39(3):199-208.

Meyerhans et al. Temporal fluctuations in HIV quasispecies in vivo are not reflected by sequential HIV isolations. Cell. Sep. 8, 1989;58(5):901-10.

Morein et al. Mechanisms behind the immune response induced by immunostimulating complexes. AIDS Res Hum Retroviruses. 1994;10 Suppl 2:S I09-14.

Molecular cloning— A laboratory manual; Eds. Maniatis T., Fritsch E.F., Sambrook J., Cold spring Harbor Laboratory, Cold Spring Harbor, New York (1992).

Molecular cloning— A laboratory manual; Eds. Maniatis T., Fritsch E.F., Sambrook J., Cold spring Harbor Laboratory, Cold Spring Harbor, New York (1992).

Human Retroviruses and AIDS 1993: a Compilation and Analysis of Nucleic Acid and Amino Acid Sequences. Myers G, Korber B, Wain-Hobson S and Smith RF, Eds. Theoretical Biology and Biophysics Group, Los Alamos National Laboratory, Los Alamos, NM.

Human Retroviruses and AIDS 1995: a Compilation and Analysis of Nucleic Acid and Amino Acid Sequences. Myers G, Korber B, Hahn BH, Jeang K-T, Mellors JW, McCutchan FE, Henderson LE and Pavlakis GN, Eds. Theoretical Biology and Biophysics Group, Los Alamos National Laboratory, Los Alamos, NM.

Neuveut and Jeang. Recombinant human immunodeficiency virus type 1 genomes with tat unconstrained by overlapping reading frames reveal residues in Tat important for replication in tissue culture. J Virol. Aug. 1996;70(8):5572-81.

Nietfield et al. Sequence constraints and recognition by CTL of an HLA-B27-restricted HIV-1 gag epitope. J Immunol. Mar. 1, 1995;154(5):2189-97.

Nixon et al. HIV-1 gag-specific cytotoxic T lymphocytes defined with recombinant vaccinia virus and synthetic peptides. Nature. Dec. 1, 1988;336(6198):484-7.

Oggioni et al. Immunization of mice by oral colonization with live recombinant commensal streptococci. Vaccine, 1995;13(8):775-9.

Oggioni et al. A host-vector system for heterologous gene expression in *Streptococcus gordonii*. Gene. Feb. 22, 1996;169(1):85-90.

O'Hagan et al., *Novel Delivery Systems for Oral Vaccines*, Eds., H'Hagan D. T. CRC Press, Boca Raton, FL, pp. 176 (1994).

Parslow, *Human Retroviruses*, Cullen B.R. Ed., IRL Press, Oxford, England, pp. 101 (1993).

Pilkington et al. Recombinant human Fab antibody fragments to HIV-1 Rev and Tat regulatory proteins: direct selection from a combinatorial phage display library. Mol Immunol. Mar.-Apr. 1996;33(4-5):439-50.

Pozzi et al., in *Gram—Positive Bacteria as Vaccine Vehicles for Muscosal Immunization*. Pozzi & Well Eds., Landes, Austin, pp. 35, (1997).

Puri and Aggarwal, Human immunodeficiency virus type 1 tat gene up-regulates interleukin 4 receptors on a human B-lymphoblastoid cell line. Cancer Res. Jul. 1, 1992;52(13):3787-90.

Puri et al., Constitutive expression of human immunodeficiency virus type 1 tat gene inhibits interleukin 2 and interleukin 2 receptor expression in a human CD4+ T lymphoid (H9) cell line. AIDS Res Hum Retroviruses. Jan. 1995;11(1):31-40.

Quesada-Rolander et al., Abs. # 6-S1, $2^{nd}$ European Conference on Experimental AIDS Research, Stockholm, Sweden, May 31-Jun. 3, (1997).

Quinn et al. Interleukin-15 stimulates C2 skeletal myoblast differentiation. Biochem Biophys Res Commun. Oct. 9, 1997;239(1):6-10.

Ratner et al. Complete nucleotide sequence of the AIDS virus, HTLV-III Nature. Jan. 24-30, 1985;313(6000):277-84.

Re et al. Effect of antibody to HIV-1 Tat protein on viral replication. in vitro and progression of HIV-1 disease in vivo. J Acquir Immune Defic Syndr Hum Retrovirol. Dec. 1, 1995;10(4):408-16.

Joag et al. Chimeric simian/human immunodeficiency virus that causes progressive loss of CD4+ T cells and AIDS in pig-tailed macaques. J Virol. May 1996;70(5):3189-97.

Reimann et al. A chimeric simian/human immunodeficiency virus expressing a primary patient human immunodeficiency virus type 1 isolate env causes an AIDS-like disease after in vivo passage in rhesus monkeys. J Virol. Oct. 1996;70(10):6922-8.

Reiss et al. Speed of progression to AIDS and degree of antibody response to accessory gene products of HIV-1. J Med Virol. Mar. 1990;30(3):163-8.

Reiss et al. Low antigenicity of HIV-1 rev: rev-specific antibody response of limited value as correlate of rev gene expression and disease progression. AIDS Res Hum Retroviruses. Dec. 1989;5(6):621-8. Erratum in: AIDS Res Hum Retroviruses Jan. 1990;6(1):171.

Riley et al. Intrinsic resistance to T cell infection with HIV type 1 induced by CD28 costimulation. J Immunol. Jun. 1, 1997;158(11):5545-53.

Rinaldo et al. Anti-HIV type 1 cytotoxic T lymphocyte effector activity and disease progression in the first 8 years of HIV type 1 infection of homosexual men. AIDS Res Hum Retroviruses. Apr. 1995;11(4):481-9.

Rinaldo et al. High levels of anti-human immunodeficiency virus type 1 (HIV-1) memory cytotoxic T-lymphocyte activity and low viral load are associated with lack of disease in HIV-1-infected long-term nonprogressors. J Virol. Sep. 1995;69(9):5838-42.

Rodman et al. Epitopes for natural antibodies of human immunodeficiency virus (HIV)—negative (normal) and HIV—positive sera are coincident with two key functional sequences of HIV Tat protein. Proc Natl Acad Sci U S A. Aug. 15, 1993;90(16):7719-23.

Rodman et al. Human immunodeficiency virus (HIV) Tat—reactive antibodies present in normal HIV—negative sera and depleted in HIV—positive sera. Identification of the epitope. J Exp Med. May 1, 1992;175(5):1247-53.

Rosenberg et al. Virus—induced cytokines regulate circulating lymphocyte levels during primary SIV infections. Int Immunol. May 1997;9(5):703-12.

Rosenthal and Gallichan, Challenges for vaccination against sexually-transmitted diseases: induction and long-term maintenance of mucosal immune responses in the female genital tract. Semin Immunol. Oct. 1997;9(5):303-14.

Rush et al., in *Gram—Positive Bacteria as Vaccine Vehicles for Mucosal Immunization*. Pozzi & Well Eds., Landes, Austin, pp. 107, (1997).

Sadaie et al. Activation of tat-defective human immunodeficiency virus by ultraviolet light. New Biol. May 1990;2(5):479-86.

Saiki et al. Enzymatic amplification of beta-globin genomic sequences and restriction site analysis for diagnosis of sickle cell anemia. Science. Dec. 20, 1985;230(4732):1350-4.

Sakuragi et al. Infection of macaque monkeys with a chimeric human and simian immunodeficiency virus. J Gen Virol. Nov. 1992;73 ( Pt 11):2983-7.

Salter et al. Genes regulating HLA class I antigen expression in T-B lymphoblast hybrids. Immunogenetics. 1985;21(3):235-46.

Schnorr et al. Induction of maturation of human blood dendritic cell precursors by measles virus is associated with immunosuppression. Proc Natl Acad Sci U S A. May 13, 1997;94(10:5326-31.

Sharma et al. Differential expression of cytokine genes in HIV-1 tat transfected T and B cell lines. Biochem Biophys Res Commun. Mar 17, 1995;208(2):704-13.

Shibata et al. Generation of a chimeric human and simian immunodeficiency virus infectious to monkey peripheral blood mononuclear cells. J Virol. Jul. 1991;65(7):3514-20.

Sipsas et al. Identification of type-specific cytotoxic T lymphocyte responses to homologous viral proteins in laboratory workers accidentally infected with HIV-1. J Clin Invest. Feb. 15, 1997;99(4):752-62.

Sodroski et al. Trans-acting transcriptional regulation of human T-cell leukemia virus type III long terminal repeat. Science. Jan. 11, 1985;227(4683):171-3.

Steinaa et al. Antibody to HIV-1 Tat protein inhibits the replication of virus in culture. Arch Virol.1994;139(3- 4):263-71.

Steinman RM. Dendritic cells and immune-based therapies. Exp Hematol. Jul. 1996;24(8):859-62.

Tahtinen et al. Fine specificity of the B-cell epitopes recognized in. HIV-1 NEF by human sera. Virology. Mar. 1992;187(1):156-64.

Titti, F., De Rossi, A., Geraci, S., Corrias, F., Panzini, G.L., Sernicola, L., Maggiorella, M.T., Baroncelli, S., Fabiani, M., Amadori, A., Chieco-Bianchi, L., Verani, P.; Immunotherapy of SIV—infected macaca fasciculais with an inactivated whole SIV immunogen. Cell Pharmacol, 3, 269-276, 1996.

Trinchieri G. Function and clinical use of interleukin-12. Curr 0pin Hematol. Jan. 1997;4(1):59-66.

Van Baalen et al. Fine-specificity of cytotoxic T lymphocytes which recognize conserved epitopes of the Gag protein of human immunodeficiency virus type 1. J Gen Virol. Aug. 1996; 77 ( Pt 8):1659-65.

Van Baalen et al. Human immunodeficiency virus type I Rev— and Tat-specific cytotoxic T lymphocyte frequencies inversely correlate with rapid progression to AIDS. J Gen Virol. Aug. 1997;78 ( Pt 8):1913-8.

Vellutini et al. Development of lymphoid hyperplasia in transgenic mice expressing the HIV tat gene. AIDS Res Hum Retroviruses. Jan. 1995;11(1):21-9.

Venet et al. Cytotoxic T lymphocyte response against multiple simian immunodeficiency virusA (SIV) proteins in SIV-infected macaques. J Immunol. May 1, 1992;148(9):2899-908.

Viscidi et al. Inhibition of antigen—induced lymphocyte proliferation by Tat protein from HIV-1. Science. Dec. 22, 1989;246(4937):1606-8.

Vogel et al. The HIV tat gene induces dermal lesions resembling Kaposi's sarcoma in transgenic mice. Nature. Oct. 13, 1988;335(6191):606-11.

Voss et al. Human immunodeficiency virus type 1 envelope glycoprotein-specific cytotoxic T lymphocytes in simian—human immunodeficiency virus—infected rhesus monkeys. Virology. Apr. 20, 1995;208(2):770-5.

Wain-Hobson S. The fastest genome evolution ever described: HIV variation in situ. Curr Opin Genet Dev. Dec. 1993;3(6):878-83.

Westendorp et al. Human immunodeficiency virus type I Tat upregulates interleukin-2 secretion in activated T cells. J Virol. Jul. 1994;68(7):4177-85.

Westendorp et al. Sensitization of T cells to CD95-mediated apoptosis by HIV-1 Tat and gp120. Nature. Jun. 8, 1995;375(6531):497-500.

Wolf et al. Cloning of cDNA for natural killer cell stimulatory factor, a heterodimeric cytokine with multiple biologic effects on T and natural killer cells. J Immunol. May 1, 1991;146(9):3074-81.

Yang et al. The human immunodeficiency virus Tat proteins spedifically associate with TAK in vivo and require the carboxyl—terminal domain of RNA polymerase II for function. J Virol. Jul. 1996;70(7):4576-84.

Yang et al. Efficient lysis of human immunodeficiency virus type 1-infected cells cytotoxic T lymphocytes. J Virol. Sep. 1996;70(9):5799-806.

Yasutomi et al. Simian immunodeficiency virus-specific cytotoxic T-lymphocyte induction through DNA vaccination of rhesus monkeys. J Virol. Jan. 1996;70( 1 ):678-81.

Zauli et al. The human immunodeficiency virus type-1 Tat protein upregulates Bcl-2 gene expression in Jurkat T—cell lines and primary peripheral blood mononuclear cells. Blood. Nov. 15, 1995;86(10):3823-34.

Zauli et al. Tat protein stimulates production of transforming growth factor-beta 1 by marrow macrophages: a potential mechanism for human immunodeficiency virus-1-induced hematopoietic suppression. Blood. Dec. 15, 1992;80(12):3036-43.

Zauli et al. Pleiotropic effects of immobilized versus soluble recombinant HIV-1 Tat protein on CD3-mediated activation, induction of apoptosis, and HIV-1 long terminal repeat transactivation in purified CD4+ T lymphocytes J Immunol. Sep. 1, 1996;157(5):2216-24.

Zobel et al. Cationic polyhexylcyanoacrylate nanoparticles as carriers for antisense oligonucleotides. Antisense Nucleic Acid Drug Dev. Oct. 1997;7(5):483-93.

Gibellini et al. Upregulation of c-Fos in activated T lymphoid and monocytic cells by human immunodeficiency virus-1 Tat protein. Blood. Mar. 1, 1997;89(5):1654-64.

Baur et al. Viral culture and p24 antigenemia of human immunodeficiency virus (HIV)-infected individuals correlated with antibody profiles determined with recombinant polypeptides of all HIV-1 open—reading frames. J Infect Dis. Mar. 1992;165(3):419-26.

Klein et al. Kinetics of Gag-specific cytotoxic T lymphocyte responses during the clinical course of HIV-1 infection: a longitudinal analysis of rapid progressors and long-term asymptomatics. J Exp Med. Apr. 1, 1995;181(4):1365-72.

Bowen et al. Mucosal delivery of herpes simplex virus vaccine. Res Virol. Jul.-Aug. 1992;143(4):269-78.

Zamarchi et al. In vitro spontaneous production of anti—SIV antibodies is a reliable tool in the follow-up of protection of SIV—vaccinated monkeys. AIDS Res Hum Retroviruses. Nov. 1993;9(11):1139-44.

Fiore et al. Pokeweed mitogen—stimulated peripheral blood mononuclear cells from at—risk seronegative subjects produce in vitro HIV-1-specific antibodies. AIDS. Aug. 1991;5(8):1034-6.

Roman et al. Immunostimulatory DNA sequences function as T helper-1-promoting adjuvants. Nat Med. Aug. 1997;3(8):849-54.

Allen et al. A new strategy for attachment of antibodies to sterically stabilized liposomes resulting in efficient targeting to cancer cells. Biochim Biophys Acta. Jul. 26, 1995;1237(2):99-108. Erratum in: Biochim Biophys Acta Dec. 13, 1995;1240(2):285.

* cited by examiner

*: Percentage of inhibition

HIV-1 TAT COMPOSITIONS

FIELD OF THE INVENTION

The present invention refers to a prophylactic and/or therapeutic vaccine anti-HIV, anti-AIDS and against tumors and syndromes associated with HIV infection, that utilizes as immunogens wild-type or mutated proteins, peptides or DNA of HIV Tat, alone or associated with proteins, peptides or DNA of other viral products (Nef, Rev, Gag) or cytokines potentiating the antiviral immune response.

The invention refers also to the immunization with Tat or its derivatives by using autologous dendritic cells, mucosal immunization, or ex-vivo immunization of peripheral blood cells expanded by co-stimulation with anti-CD3 and anti-CD28 monoclonal antibodies and to the delivery of the above mentioned immunogens using erythrocytes or nanoparticles.

BACKGROUND OF THE INVENTION

AIDS (acquired immunodeficiency syndrome) is caused by HIV (Human Immunodeficency Virus) and is characterized by immunodeficiency, tumors, such as Kaposi's sarcoma (KS) and B-cell lymphomas, opportunistic infections and central nervous system disorders. Since AIDS is spread world-wide and has a high mortality, one of the most important Public Health goal is to develop a prophylactic and/or therapeutic vaccine against HIV or AIDS. Most of the past and current strategies have used the viral envelope or its sub-units as immunogens, but with unsatisfactory results due to the high variability of the viral envelope (ref. 162, 112—throughout this specification, various references are referred to in parenthesis to more fully describe the state of the art to which the present invention pertains. Full bibliographic information for each citation is found at the end of the specification, immediately preceding the claims). Therefore, as an alternative to sterilizing immunity, it is a common opinion that it could be sufficient to block progression of infection and disease onset. Moreover, immuno-protective responses can be obtained utilizing DNA regions of HIV as immunogens (ref. 91, 17). Owing to the published experimental data, the inventor believes that it is necessary to produce a vaccine that utilizes viral products other than env. In particular, the viral proteins to be used as immunogens must be more conserved among HIV isolates, capable of inducing an effective immune response, both humoral and cellular, and must have a vital function for the virus. Such products must be experimented in the model of non human primates (because their immune system is more similar to that of humans as compared to phylogenetically more distant animals) and in which AIDS can develop after virus infection. The HIV-1 Tat protein has all the characteristics to be a good immunogen for vaccine purposes: it is conserved, immunogenic and essential in the early phases of the viral infection. Moreover, Tat has a key role not only in viral replication, transmission and progression of the infection, but also in the onset and progression of AIDS-associated tumors, for instance KS, which is the most frequent AIDS-associated tumor, and of other syndromes and symptoms developing after HIV infection.

Tat is a protein of 86-102 amino acids, depending on the viral strain, coded by two exons. Tat is produced soon after the infection, localizes in the nucleus and transactivates the expression of all viral genes by interacting with the "Tat-responsive element" (TAR) present in the LTR (Ref. 25). Tat has also a role in HIV virulence (Ref. 63, 113, 60, 84). The product of the first exon (amino acids 1-72) is conserved among different viral isolates (Ref. 112) and is sufficient for the transactivation of the HIV-1 products (Ref. 25). It contains 4 domains. The acidic domain (amino acids 1-21) is important for the Tat interaction with cellular proteins; the cysteine rich region (amino acids 22-37) represents the transactivation domain. This region is the most conserved among the primary isolates (Ref. 108) of cysteine 22 with a glycine abolishes the capacity of Tat to transactivate the HIV-LTR (Ref. 166) the core domain (amino acids 38-48) is also conserved and it is important for function. Substitution of lysine 41 with a threonine inactivates the transactivating activity of Tat on the HIV LTR (Ref. 70); the basic domain (amino acids 49-57), rich in arginine and lysine, is necessary for the nuclear localization of Tat and binds specifically its RNA target (TAR) (Ref. 25). Moreover, the basic region is responsible for the binding of extracellular Tat to heparin and to heparansulphate proteoglycans (HSPG) (Ref. 26). Mutations in the basic region abolish such interactions. The carboxy-terminal portion of Tat is not necessary for the LTR transactivation, but contains an arginine-glycine-aspartic acid sequence (RGD), usually present in the extracellular matrix proteins (ECM), that is responsible for the binding of Tat to the integrin receptors $\alpha_5\beta_1$ e $\alpha v\beta_3$. These interactions mediate the Tat effects on AIDS-associated tumors and on the immune, vascular and nervous system (Ref. 11, 42, 170, 25). During the acute infection of T-cells with HIV-1, or after transfection of the tat gene in COS-1 cells, the Tat protein is released in the absence of cellular death in the extracellular environment (Ref. 40, 41, 25). Tat release from infected cells occurs also in vivo since extracellular Tat is present in the serum of infected subjects (Ref. 164) and in AIDS-KS lesions (Ref. 42). After release, part of the protein remains in a soluble form, and part binds to the HSPG of the ECM. Tat bound to the HSPG can be recovered in a soluble form by the addition of heparin. The binding with heparin is due to the Tat basic region; it prevents the effects of extracellular Tat and protects the protein from oxidation. This feature has been used by us to purify Tat with a high biological activity (Ref. 26). Extracellular Tat can be internalized by cells, can migrate into the nucleus and transactivate viral gene expression (Ref. 49, 98, 100, 41). The internalization of Tat occurs by endocytosis mediated by the binding of RGD region of Tat to $\alpha_5\beta_1$ and $\alpha_v\beta_3$ (Ref. 10, 42, Ensoli et al., unpublished data) and/or by the basic region which binds to HSPG.

Tat can activate viral replication and virus transmission also through indirect mechanisms involving the modulation of the expression of cellular genes which play a key role in the control of cell survival, and on the expression of inflammatory cytokines (IC) with an effect on viral replication (Ref. 25).

Beyond its importance in viral replication, Tat plays an important role in AIDS pathogenesis. Tat is able to modulate the survival and proliferation of infected and non-infected cells by causing activation or repression of cytokines, such as IL-2 (Ref. 123, 163, 31), or of genes with a key role in the cell cycle (Ref. 145, 169, 164, 173). The anti- or pro-apoptotic effects of Tat depend on a number of factors such as the cell type, the fact that Tat is expressed by the cell or added to the cell and on its concentration (Ref. 40, 41, 171).

Tat is the factor responsible for the enhanced frequency and aggressiveness of KS in HIV-1 infected subjects (Ref. 43, 33). KS is a tumor of vascular origin and it is the most frequent neoplasia in HIV-infected individuals. Tat induces KS cells and endothelial cells activated by IC to migrate, to express type IV collagenase, to invade the ECM and to proliferate, such mechanisms being necessary for angiogenesis and tumor invasion (Ref. 40, 41, 42, 2, 46). Such effects of Tat are induced by IC, since they stimulate the expression of the Tat receptors, $\alpha_5\beta_1$ and $\alpha_v\beta_3$ (Ref. 10). Tat mimics the effect of ECM proteins, such as fibronectin and vitronectin and both the RGD region and the basic region are necessary for the effects of the extracellular Tat on KS cells, on angiogenesis and on progression of KS. The capability of extracellular Tat of binding in vivo its receptors in the AIDS-KS lesions (Ref. 40) support the idea that Tat is involved in the onset and the maintenance of AIDS-associated KS. Moreover mice transgenic for the tat gene develop KS or other phenotypes depending on the level of expression of the transgene (Ref. 160, 34).

It has been suggested that Tat plays a role in the hyperpro-lipherative phenomena and in the pathogenesis of the B lymphomas, frequently observed in seropositive subjects and in tat-transgenic mice (Ref. 157), through mechanisms involving the enhancement of bcl-2 and cytokines expression (Ref. 122). Other evidence confirms a probable role of Tat in oncogenesis (Ref. 72).

Tat can also activate the expression of viral promoters, such as those of herpesviruses and of other viruses which reactivate in AIDS individuals, promoting the onset and progression of opportunistic infections (Ref. 25).

Tat seems also able to exert neurotoxic effects both direct (through the basic and the RGD regions) and indirect through induction of IC having a toxic effect on the neurons of the central nervous system or on the hematoenchephalic barrier (Ref. 25). Regarding the immune response to Tat, a number a studies suggest that anti-Tat antibodies play a protective role in the control of the evolution of the disease in vivo (Ref. 130, 135, 136, 149, 127). Moreover, in vitro, anti-Tat antibodies not only suppress the internalization, the transcellular activation of Tat and viral infection (Ref. 41, 127), but they also inhibit the proliferation and Tat-induced migration of KS cells and the formation of KS-like lesions in mice (Ref. 40, 41, 42). Finally, our preliminary results demonstrate that anti-Tat antibodies are absent in AIDS-KS subjects, suggesting that such subjects cannot block the activity of extracellular Tat.

The development of an anti-Tat cell-mediated response in the initial phase of infection is important for the control of the infection itself (Ref. 161, 133, 59) and there exists an inverse correlation between the presence of specific anti-Tat CTL and disease progression (Ref. 156). Such results were obtained in studies on macaques inoculated with SIVmac (Ref. 91, 158). Moreover, recent data in mice of different species in which Tat was inoculated either as a plasmid or as protein showed that it is possible to induce both a humoral and cellular response to the protein (Ref. 61). However, it has been observed variability among several mouse species and such results have not been reproduced with the same immunogens in non-human primates (Ref. 124). The lack of reproducibility in non is human primate model of the results from vaccine experiments performed in mice is frequent and possibly due to the different immune system of these two species which can raise different immune responses with the same immunogen, as demonstrated for the HIV Env protein. Thus, candidate vaccines for humans must be tested in non-human primates and not only in inferior species.

The inventor believes that other viral proteins, or parts thereof, could be associated with Tat to enhance a specific immune response against HIV and could be of benefit also in the vaccination against the onset of tumors and of other pathologies and symptoms associated with HIV infection. Such products are the Nef, Rev and Gag proteins of HIV.

Nef is another viral regulatory protein important for the development of disease (Ref. 3, 48, 58). Nef is produced early after infection and it is released in the extracellular environment (Ensoli, unpublished data). In the SIVmac/macaque system the presence of Nef correlates with high viral replication and with progression to AIDS (Ref. 71). Nef is more variable than Tat (Ref. 112). Nef is an immunogenic protein (Ref. 53, 32, 35, 151) and it is capable of inducing CTL (Ref. 16, 36). In particular, it has been identified an immunodominant region of Nef (region 73-144) which is recognized by CTLs in most HIV-infected patients. Rev is a viral regulatory protein produced early during infection (Ref. 51, 119) and released in the extracellular environment (Ensoli et al., unpublished data). Rev is essential for HIV replication and for disease progression, and is coded by two exons, partially overlapping Tat-coding regions. Rev is a nuclear protein (Ref. 44) necessary for the expression of the viral messenger RNAs coding for the late proteins (Ref. 97). Rev is a highly conserved protein among the various viral isolates of HIV-1 (Ref. 111) and it is immunogenic. In fact, it induces the production of specific antibodies directed against the two functional domains of the protein (Ref. 120) during the natural infection in man (Ref. 131) and after inoculation in mice (Ref. 61). Lower levels of anti-Rev antibodies in the sera of infected individuals seem to correlate with the progression to AIDS (Ref. 131). Rev can induce CTL both in man and in monkey (Ref. 156, 158) and it has been reported that a specific anti-Rev CTL response, early during the infection, is is inversely correlated with disease progression (Ref. 156, 158).

Another viral target is the gag gene, which is expressed late during infection and codes for a group of highly immunogenic structural proteins of the capsid (Ref. 18, 147). The anti-Gag antibody titers are high and stable during the asymptomatic phase of infection, and reach very low levels when the infection progresses to full-blown AIDS, in combination with the drop of CD4+ lymphocytes and the presence of the virus in the peripheral blood (Ref. 174, 73). Gag proteins induce CTL activity early during infection, both in man and in primates (Ref. 103, 168), and their presence is significantly related with the control of the initial viremia and with disease progression (Ref. 175, 6, 134, 167, 92). Finally, p17 and p24 proteins contain immunodominant epitopes which are maintained in different HIV-1 and HIV-2 isolates and are recognized by CTL (Ref. 89, 19, 114, 155, 115).

The inventor believes that cytokines or parts thereof, such as IL-12 and IL-15, or other immuno modulant cytokines such as IFNα or IFNβ or other proteins enhancing the immunogenic effect of Tat, can be utilized as adjuvants in the formulation of the anti-Tat vaccine. IL-12 is a strong immunoregulatory cytokine produced by antigen-presenting cells (APC) such as B and dendritic cells (Ref. 154). IL-12 is produced early after HIV infection and has a pro-inflammatory action inducing NK cells and T-lymphocytes to produce IFNγ which activates phagocytes and promotes the induction of Th1 lymphocytes. IL-12 plays a fundamental role in the resistance to a number of infections caused by bacteria, fungi, viruses and shows a high anti-tumor activity. Several evidences suggest that viruses which induce immunosuppression, such as HIV and measles virus, act also through mechanisms which suppress IL-12 production (Ref. 57, 50, 144).

IL-15 is a pleiotropic cytokine expressed by non-lymphoid tissues, by activated monocytes/macrophages and by dendritic cells (DC) (Ref. 125, 66). IL-15 plays an important role in regulating the NK activity, in the proliferation of T lymphocytes and in the CTL activity (Ref. 67, 24). IL-15 induces the expression of CTLs against HIV antigens, in the absence of IL-2 and functional CD4+ T-lymphocytes (Ref. 68, 1). Moreover, similarly to IL-2, IL-15 induces the expansion of lymphocytes with cytotoxic activity ("lymphokine-activated killer", LAK) and stimulates production of IFNγ in PBMCs of seropositive patients (Ref. 93). IL-15 activates monocytes to produce chemokines, playing a role in the onset of inflammatory processes (Ref. 8).

Recent studies have shown that the co-stimulation of CD4+ lymphocytes with paramagnetic beads, coated with anti-CD3 e anti-CD28 monoclonal antibodies determines a logarithmic and polyclonal expansion of lymphocytes from HIV-infected subjects (Ref. 82) without activating virus replication and transmission. Such antiviral activity is a consequence of both the negative modulation of the expression of CCR5, the co-receptor of HIV-1 monocytotropic strains (Ref. 23) and, to a lesser extent, of the high levels of chemokines induced by the co-stimulation with anti-CD3 and anti-CD28 monoclonal antibodies (Ref. 132). The inventor believes that the possibility to expand autologous lymphocytes from HIV infected subjects in the absence of viral replication/transmission, permits to obtain an effective ex vivo immunization, described in the examples, which can be highly helpful in developing an anti-Tat vaccine.

Within the different systems aimed at the generation of effective antiviral and anti-tumor vaccines, the inventor believes that the utilization of dendritic cells could be key in the induction of an immune response to Tat. This is due to the fact that these cells are the most efficient in presenting the antigen and the sole able to stimulate naive lymphocytes, in the absence of adjuvants (Ref. 150). The use of dendritic cells replaces the function of several adjuvants consisting in the induction of a non specific immune response (natural immunity) which, in turns, generates a strong primary specific response in the presence of the antigen.

Since the transmission of HIV infection primarily occurs at the mucosal level (genital and rectal in the adult, oral in the new-born), the inventor believes that the induction of protective immunity at the mucosal level is a primary goal. Many studies have recently shown the possibility to induce mucosal immunization, local and systemic. Particularly, the nasal and oral routes have shown to be the most efficient in inducing an effective mucosal immune response, even at distant sites, such as the genital mucosa (Ref. 138, 118). In particular, the inventor believes that the use of S. Gordonii and Lactobacillus bacteria, modified to express the above mentioned viral antigens, might be a valid strategy to induce or potentiate a specific immune response at the mucosa level in monkeys and in man. These bacteria are, in fact, able to colonize the mouse oral and vaginal mucosa, and to induce a specific, local and systemic, antibody response against heterologous antigens expressed on the surface of recombinant bacteria (Ref. 116, 104, 106, 121, 117, 139, 105, 107). Finally, these bacteria act as live vectors and can induce a prolonged stimulation of the immune system. Moreover, the inventor believes that non-replicating and non-pathogenic recombinant viral vectors, such as herpes simplex type-1 viruses (HSV-1) (Ref. 99), can be used to express viral proteins for systemic (intradermic) and mucosal (oral, vaginal and nasal routes) immunization. In fact, these vectors can accommodate large exogenous sequences (Ref. 52, 64), such as several HIV genes (regulatory, accessory and structural). Moreover, herpes vectors can also be administered via the oral, nasal or vaginal route (Ref. 176, 75).

The inventor believes that Tat (either as protein or DNA), alone or in combination with the other immunogens described above, can be inoculated also by using new delivery systems, such as erythrocytes or nanoparticles. In particular, the inventor believes that it is possible to deliver antigens bound to the membrane of autologous erythrocytes (Ref. 95, 96). Since these erythrocytes are removed from the blood by macrophages, professional antigen presenting cells, only after 120 days, this feature can be used for vaccine purposes. Finally, another delivery strategy is the use of nanoparticles that can carry proteins and DNA (Ref. 27, 172). Nanospheres are polymeric colloidal particles of diverse chemical composition, variable from 10-1000 nm. Different substances (oligonucleotides, drugs, proteins, peptides, DNA) can be loaded on their surface or absorbed in the particle and delivered into the cytoplasm or the nucleus of the cells from where they are slowly released. This allows the utilization of very small amounts of the substance to be delivered.

Based on the results described above, the inventor believes that the immunization with Tat, alone or in combination with other viral products or immuno modulant cytokines, or parts thereof, in the presence or not of adjuvants, could block viral replication in subjects exposed after vaccination and in the infected subjects, maintaining the infection in an abortive phase, which can be more easily controlled by the immune system. Therefore, the inventor believes that a Tat-based vaccine should be able to induce an immune response, both humoral and cellular, sufficient to block or reduce the replication or the transmission of the virus and therefore capable of controlling virus replication and of blocking productive infection, progression to disease and the onset of tumors and other AIDS-associated syndromes and symptoms. It is, therefore, possible to use the anti-Tat vaccine for both preventive and therapeutic purposes. In fact, a humoral response against Tat could neutralize the effects of extracellular Tat reducing and limiting the infection, whereas the cell-induced response against Tat as well as against other viral proteins enclosed in the vaccine formulation, could destroy the virus infected cells leading to the control the infection. This allows the necessary period of time to the immune system for developing a complete response towards all viral components of the infecting virus in the absence of irreversible damages due to viral replication.

It has been described the use of Tat as an immunogen (WO 95/31999). However, it is disclosed the use of a biologically inactive protein; moreover, in the same patent application no evidence is shown of the biological activity of the "native" Tat protein.

In addition, there is a strong technical prejudice against the use of a biologically active Tat protein, in that it is believed to enhance viral replication in infected subjects and/or to give immunosuppression in seronegative or seropositive individuals (A. Tonelli: Aids, un vaccino per sperare. "La Repubblica", pag. 10, 24 Oct. 1998)

As evident from the above, despite the efforts made, an efficaceous anti-HIV to vaccine based on Tat has not been developed yet.

SUMMARY OF THE INVENTION

It is an object of the present invention a Tat protein or peptides of Tat or the Tat DNA for use as a vaccine, being intended that Tat must be in its biologically active form.

Another object of the invention is a protein or a peptide vaccine to be used in humans, prophylactic or therapeutic against AIDS, AIDS-associated tumors and HIV-associated syndromes and symptoms and comprised of recombinant wildtype Tat protein or its mutants (SEQ ID NOS:1, 3, 5, 7 and 9), expressed and purified as described, or wild-type or mutated Tat peptides (Pep. 1-7, SEQ ID NOS:11-17, respectively), administered alone or conjugated with T-helper tetanus toxoid epitope or other T-helper epitopes.

Another object of the invention is a vaccine as described above, in combination with recombinant HIV Nef, Rev and/ or Gag proteins or peptides of Nef, Rev and Gag administered as Tat/Nef, Tat/Rev, Tat/Gag fusion proteins or as parts of these proteins.

Another object of the invention is a vaccine as described above, in combination with recombinant proteins of immuno-modulant cytokines like IL-12, IL-15 or others molecules or part of these, capable of increasing the antiviral immune response, or a vaccine constituted by Tat/IL-12, Tat/IL-15 or Tat/other fusion proteins, or part of these, capable of increasing the antiviral immune response. Another object of the invention is a DNA vaccine, to be administered in humans, prophylactic or therapeutic, against AIDS, AIDS-associated tumors and HIV-related syndromes and symptoms, constituted by vectors coding for wild-type Tat or its mutants (SEQ ID NOS:1, 3, 5, 7 and 9), or part of these, inserted in the expression plasmid vector pCV0 or other vectors.

Another object of the invention is a DNA vaccine, as described in 4, in combination with HIV rev, nef or gag genes, or part of these, inserted in the pCV0 vector, or a DNA vaccine administered as a vector co-expressing tat/rev, tat/nef, tat/gag genes or part of these.

Another object of the invention is a DNA vaccine as described above, in combination with the DNA coding for IL-12 and IL-15 or other genes coding for immuno modulant cytokines or part of these, inserted in pCV0 or other vectors, or a DNA vaccine administered as a vector co-expressing Tat/IL-12, Tat/IL-15 or Tat/other molecules, or part of these, capable of increasing the anti-viral immune response.

Another object of the invention is an anti-Tat vaccine, as a protein, peptide and/or DNA, alone or combined as described above for immunization with autologous dendritic cells by ex vivo treatment.

Another object of the invention is an anti-Tat vaccine as a protein, peptide and/or DNA, alone or combined as described above, for mucosal immunization (nasal, oral, vaginal or rectal).

Another object of the invention is an anti-Tat vaccine as a protein, peptide and/or DNA, alone or combined as described above, for ex vivo immunization of peripheral blood cells from infected subjects expanded through co-stimulation with anti-CD3 and anti-CD28 monoclonal antibodies conjugated to paramagnetic beads and re-infused in the host.

Another object of the invention is an anti-Tat vaccine, as a protein, peptide and/or DNA as described above, combined with inhibitors of viral replication.

Another object of the invention is an anti-Tat vaccine as already described, in combination with adjuvants which increase the immune response.

Another object of the invention is an anti-Tat vaccine, alone or in combination as already described, administered by specific delivery systems, such as nanoparticles, herpes vectors, red blood cells, bacteria or any other delivery system by which the above described vaccine, in all its combinations, can be administered.

Further objects will be evident from the detailed description of the invention.

BRIEF DESCRIPTION OF THE FIGURES

FIG. 1A. Panel A, cells pre-incubated with buffer, incubated with BSA.

FIG. 1A. Panel B, cells pre-incubated with buffer, incubated with Tat.

FIG. 1A. Panel C, cells pre-incubated with monoclonal antibodies CDw49e and CD29, incubated with Tat.

FIG. 1A. Panel D, cells pre-incubated with monoclonal antibodies CD51 and CD61, incubated with Tat.

FIG. 1A. Panel E, cells pre-incubated with anti-human factor VIII antibodies (control antibodies), incubated with Tat.

DETAILED DESCRIPTION OF THE INVENTION

Figure 1A:
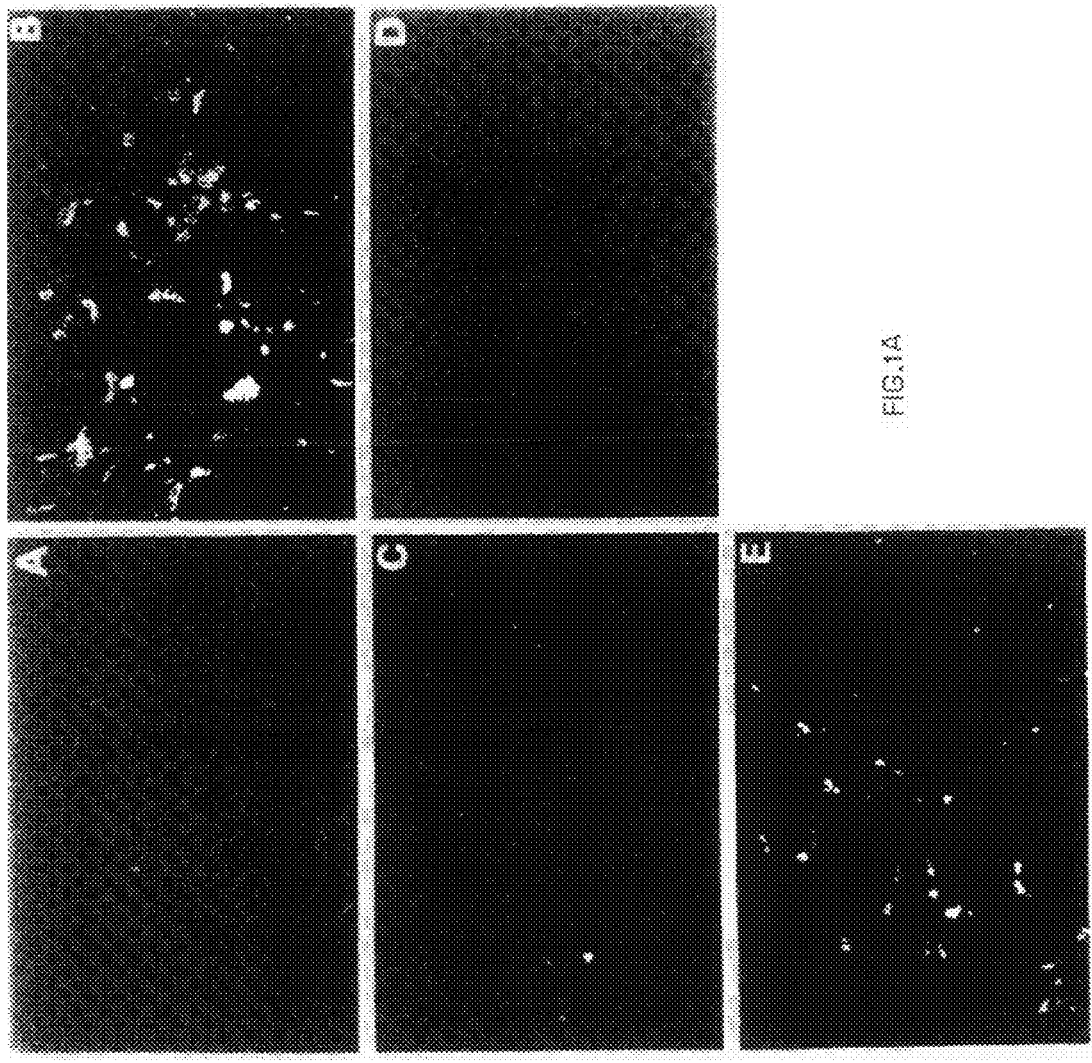
FIG. 1A. Inhibition of uptake of 10 ng/ml rhodaminated Tat protein by pre-incubation of cytokine-activated endothelial cells with anti-integrin antibodies.

The present invention refers to Tat as the active principle for a prophylactic and/or therapeutic vaccine against HIV infection, the progression towards AIDS and the development of tumors and other syndromes and symptoms in subjects infected by HIV. Tat, or wild-type Tat, is in is in its active form or, more correctly, in its biologically active form (as explained herein below) either as recombinant protein or peptide or as DNA. More particularly, the invention refers to a vaccine based on HIV-1 Tat as immunogen, inoculated as DNA and/or recombinant protein or as peptides, alone or in combination with other genes or viral gene products (Nef, Rev, Gag) or parts thereof, or in combination with various immuno modulant cytokines (IL-12, IL-15) or with the gene coding for an immuno modulant cytokine or part thereof. Tat, Nef, Rev, Gag and the immuno modulant cytokines are administrated both as a mixture of recombinant proteins, peptides or fusion proteins (Tat/Nef, Tat/Rev, Tat/Gag, Tat/IL-12, Tat/IL-15) or as plasmid DNA. In the present description "wild-type Tat" and "Tat in its active form" have to be considered synonymous of "biologically active Tat".

According to the present invention, as "biologically active Tat" it is intended the protein that, at picomolar to nanomolar concentrations (from 10 ng/ml or less to 1 μg/ml, preferably 0.1 ng/ml to 100 ng/ml) is capable of:

(i) entering and localizing in the nuclei of activated endothelial cells or dendritic cells, as measured in Example 1A;

(ii) activating the proliferation, migration and invasion of Kaposi's sarcoma (KS) cells and cytokine-activated endothelial cells protein (Ref. 40, 2);

(iii) activating virus replication when added to infected cells as measured a) by the rescue of Tat-defective proviruses in HLM-1 cells after the addition of exogenous protein (Ref: 41); b) by the transactivation of HIV-1 gene expression in cells transfected with a HIV-1 promoter-reporter plasmid protein (Ref. 41);

(iv) inducing in mice the development of KS-like lesions in the presence of angiogenic factors or inflammatory cytokines (Ref. 42).

The inventor considers to be fundamental for biologically active Tat that one of the points (i) or (ii) be verified, preferably both should be verified, more preferably point (i) or point (ii) or both in combination with point (iii) a) and/or (iii) b) should be is verified. The best results will be obtained when all (i) to (iv) points are verified. A Tat protein or fragments of Tat with these characteristics are capable of inducing in vivo a cytotoxic and antiviral immune response. In fact, a biologically active Tat with the characteristics mentioned above is capable of binding specific cell surface receptors and is taken up via these receptors. Tat uptake is essential for inducing a cytotoxic response.

Previous or ongoing studies, related to the development of a vaccine based on Tat, have not utilized a biologically active Tat protein with the characteristics mentioned above.

A method to obtain and to handle a biologically active Tat according to the present invention is described in Example 1.

It is also described an immunization method utilizing autologous dendritic cells treated ex vivo with recombinant Tat protein, or peptides thereof, alone or with a mixture of recombinant proteins or peptides (Tat, Nef, Rev, Gag) or with the Tat protein and one or more immuno modulant cytokines, or parts thereof, or transduced with eukariotic vectors containing the tat gene alone or in combination with viral genes coding for Nef, Gag or Rev, or tat and the gene coding for an immuno modulant cytokine or part thereof.

Strategies to induct an immune response at the mucosal level are also described. Tat or its peptides, alone or in combination with viral proteins and/or cytokines is inoculated at the mucosal level to enhance and induce the local immune response. The HIV-1 Tat protein or sub-units thereof will also be utilized for the ex vivo immunization of CD4+ and CD8+ lymphocytes isolated from the peripheral blood of infected subjects. The Tat antigen specific cells will be then expanded in vitro through co-stimulation with monoclonal antibodies directed against CD3 and CD28 and re-infused. Finally, it is also described the use of Tat mutants, identified to in the examples, to be utilized as immunogens, as an alternative to Tat wild type. The Tat mutants are i) in the cysteine region (cys22) and ii) in the core region (lys41), iii) the mutant deleted in the RGD sequence; iv) the double mutant deleted at lysine 41 and the RGD. Alternatively to the use of Tat mutants or Tat peptides (wild type or mutated as the protein) in case of therapeutic vaccination, inhibitors of viral replication will be utilized along with the immunogen.

In this regard, for "inhibitors of viral replication" it is intended all molecules known at the present, or those which will be discovered later on (nucleoside and non-nucleoside inhibitors of reverse transcriptase, protease inhibitors, antisense RNA and, in general, all molecules able to block HIV gene expression) able to reduce or block the HIV replication. As previously said, different methods of immunization are described, which utilize Tat protein, peptides and Tat DNA in association with other viral genes or proteins, or part thereof, or immuno modulant cytokines or genes coding for immuno modulant cytokines, or part thereof. For "part thereof" it is intended segments of genes or of proteins, above described, whose efficacy of inducing the same immunogenic effects of the entire gene or protein is demonstrated. Moreover, since the efficacy of adjuvants in vaccine strategies is known, the present invention refers to the use of known adjuvants and of those which will be discovered later on, administered together with Tat (protein or DNA) and with combinations of Tat and other genes or viral or cellular proteins. Similarly, it is hypothesized the efficacy of different delivery systems of Tat (protein or DNA) and combinations of Tat and other genes or viral or cellular proteins in inducing both a systemic and local immune response to Tat (mucosal immunization).

Results obtained from the inventor (not published), indicate that only the Tat protein, in its biologically active form, is able to bind specific cellular receptors and enter the cell. This characteristic is at the base of the immune response of accessory cells and of the immune cells more in general and, according to the inventor, it is of a fundamental importance in inducing a much stronger immune response than the inactivated protein is able to elicit. In conclusion, unlike the use of inactivated Tat as immunogen, proposed by some scientists, the inventor intends to utilize HIV-1 Tat, or its mutants, in its biologically active form, in order to induce a very strong immune response against HIV, able to prevent infection or the development of the disease and to permit efficient therapeutic strategies in HIV-1-infected individuals. According to the inventor, the vaccine can be delivered through systemic (intramuscular, i.d., subcute, etc.) or local (mucosal) routes. The last route is preferred when bacteria (see below) are utilized as delivery systems. The vaccine can be produced as follows. Tat can be prepared according to Example 1, it can be lyophilized and stored. At the moment of use, it can be resuspended in a biologically acceptable fluid, such as serum, plasma, or their fractions.

The vaccine can further comprise pharmaceutically acceptable carriers and excipients to maximize the activity of the active principle.

Transformed cells, comprising a Tat-expressing vector, or Tat mutant-expressing vector, or parts thereof, as previously described, and cells which are cultured to express Tat protein, which will be isolated for the use, are all included in the scope of the present patent.

It is intended that all Tat variants (including all types and subtypes of HIV strains), with analogous or greater activity than that above described, are included in this invention.

The present invention will be now described by means of its illustrative and not restrictive specific examples, in which reference will be made to the enclosed figures.

DETAILED DESCRIPTION OF THE FIGURES

FIG. 1A. Inhibition of uptake of 10 ng/ml rhodaminated Tat protein by pre-incubation of cytokine-activated endothelial cells with anti-integrin antibodies. Cytokine-activated human umbilical vein (HUVE) cells, treated as described in the legend to Table 2A, were pre-incubated in serum free medium containing buffer or antibodies and then incubated for 15 minutes at 37° C. with 10 ng/ml rhodaminated Tat or rhodaminated BSA.

Panel A, cells pre-incubated with buffer, incubated with BSA.

Panel B, cells pre-incubated with buffer, incubated with Tat.

Panel C, cells pre-incubated with the monoclonal antibodies CDw49e (anti-≠5) and CD29 (anti-(β1), incubated with Tat.

Panel D, cells pre-incubated with the monoclonal antibodies CD51 (anti-αv) and CD61 (anti-β3), incubated with Tat.

Panel E, cells pre-incubated with anti-human factor VIII antibodies (control antibodies), incubated with Tat.

Figure 1B:
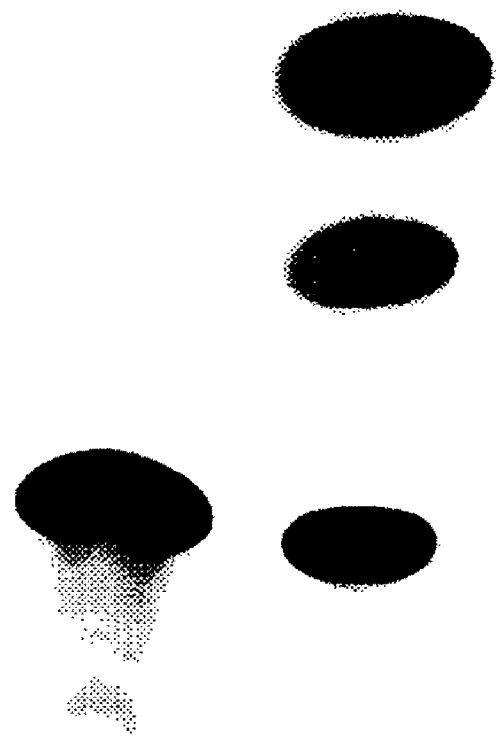
FIG. 1B. Capability of purified Tat-cys22 (Tat22) protein to compete the transactivating activity of wild type Tat protein monitored by cat assays.

FIG. 1B. Shown is the capability of purified Tat-cys22 (Tat22) protein to compete is the transactivating activity of wild type Tat protein monitored by cat assays. H3T1 cells, containing the HIV-1 LTR-CAT reporter gene (Ref. 148), were incubated with wild type Tat protein (100 ng), alone or in the presence of a molar excess of Tat-cys22 protein (100 ng). The HIV-1 LTR transactivating activity of Tat and the capability of the Tat-cys22 protein of competing with wild type Tat have been determined at 48 h after transfection by determining the cat activity in cytoplasmic extracts (corresponding to 200 μg of protein), as described (Ref. 41). The percentages (%) in acetylation of $^{14}C$-chloramphenicol are indicated.

Figure 2:
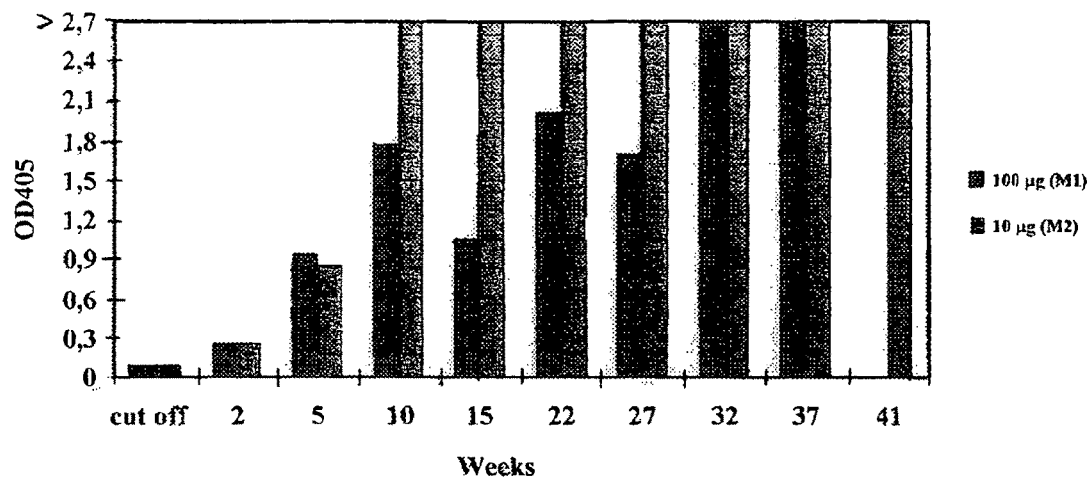
FIG. 2A. Anti-Tat specific IgG production in monkeys vaccinated with the Tat protein, determined by immuno-enzymatic assay (ELISA). Results obtained in two monkeys inoculated sub-cute with 10 or 100 µg of recombinant Tat protein re-suspended in 250 µl of autologous serum and 250 µl of RIBI.
FIG. 2B. Anti-Tat specific IgG production in monkeys vaccinated with the Tat protein, determined by immuno-enzymatic assay (ELISA). Results for the control monkey (M3).
Figure 2B:
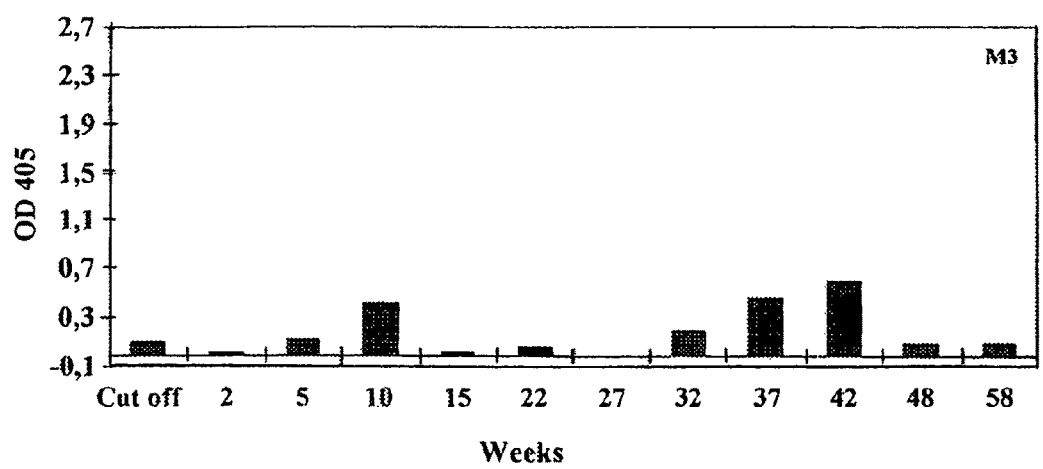

FIG. 2. Anti-Tat specific IgG production in monkeys vaccinated with the Tat protein, determined by immuno-enzymatic assay (ELISA). (A) shows the results obtained in two monkeys inoculated subcute with 10 or 100 μg of recombinant Tat protein re-suspended in 250 μl of autologous serum and 250 μl of RIBI; (B) shows the results for the control monkey (M3). Monkeys were inoculated at time 0 and after 2, 5, 10, 15, 22, 27, 32 and 37 weeks. Anti-Tat antibodies were evaluated also at week 41 in monkey M2, inoculated with 10 μg of Tat protein, and for monkey M3.

The presence of the anti-Tat antibodies in the plasma of the vaccinated animals was evaluated by ELISA prepared and characterized as follows. The Tat protein was adsorbed in PVC-96-well plates (100 ng/well in 200 μl carbonate buffer 0.05 M pH 9.6) for 12 h at 4° C. After 3 washings with PBS 1x without $Ca^{++}$ and $Mg^{++}$ (PBS-A) containing Tween 20 (0.05%), plasma diluted 1:50 in 200 μl carbonate buffer were added (in duplicate) and plates incubated at 37° C. for 90'. Wells were then washed with PBS-A 1x/Tween 0.05%, followed by the addition of 100 μl of the secondary antibody (diluted 1:1000 in PBS-A 1 x/Tween 0.1%/BSA 1%) conjugated with horseradish peroxidase, for 90' at room temperature. After 5 washings of the wells, 100 μl of substrate (ABTS 1 mM, Amersham) were added for 30-45' at room temperature. Reading was performed at the spectrophotometer (405 nm). Each ELISA included an anti-Tat rabbit polyclonal serum (positive control) diluted 1:200 to 1:6400, and the preimmune plasma (negative control) diluted 1:50. The cut-off value was calculated as the mean of the optical densities (O.D.) of negative monkey plasma +3 standard deviations (S.D.), obtained in all is the experiments with the preimmune plasma. The results shown are the average of duplicate wells. >2,7 indicates that optical density values were out of scale.

Figure 3:
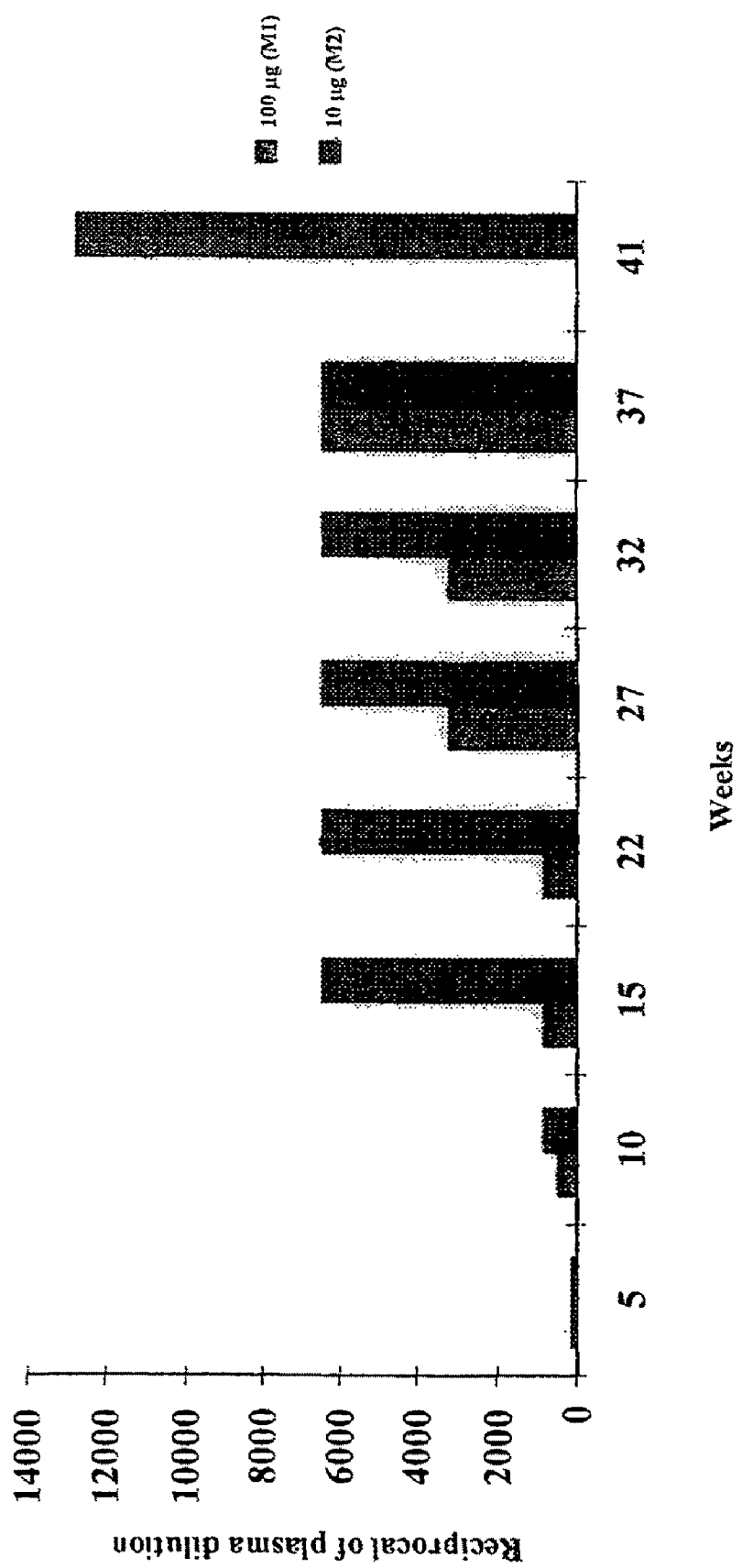
FIG. 3. Titration of anti-Tat antibodies in plasma from monkeys inoculated with 100 (M1) and 10 (M2) µg recombinant Tat protein, described in FIG. 2A and FIG. 2B.

FIG. 3. Titration of anti-Tat antibodies in plasma from monkeys inoculated with 100 (M1) and 10 (M2) μg recombinant Tat protein, described in FIG. 2. Elisa were carried out as described in FIG. 2 and plasma assayed (in duplicate) at scalar dilutions from 1:50 to 1:25.600.

The values in the ordinate represent the inverse of the highest plasma dilution at which the test was still positive. The cut-off value was calculated for each dilution and corresponded to the average O.D. of preimmune plasma from all monkeys in all experiments, +3 S.D.

Figure 4A:
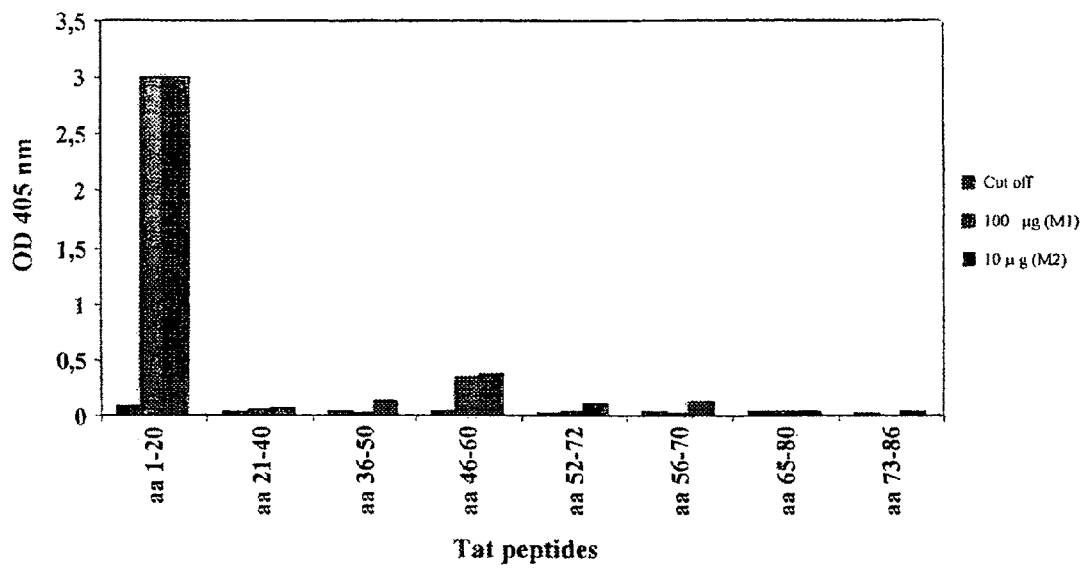
FIG. 4A. Mapping of the Tat epitopes recognized by the anti-Tat IgG from monkeys injected with 100 (M1) and 10 (M2) µg of recombinant Tat protein, described in FIG. 2A and FIG. 2B. The average results of plasma diluted 1:50 for each peptide tested in duplicate are shown.
Figure 4B:
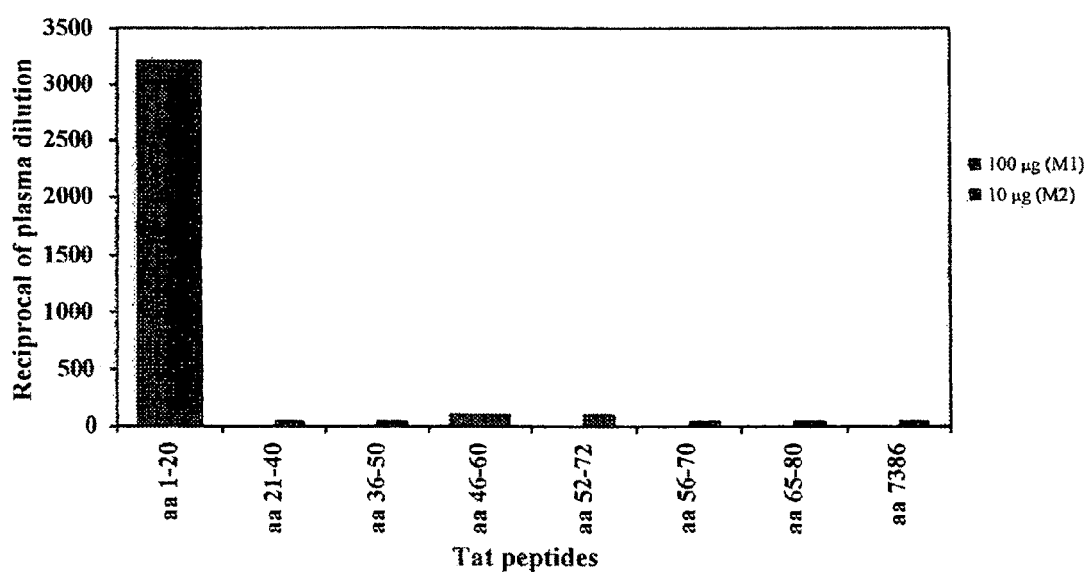
FIG. 4B. Mapping according to FIG. 4A. The antibody titers in plasma are shown, expressed as the reciprocal of the highest dilution at which the test was still positive.

FIG. 4. Mapping of the Tat epitopes recognized by the anti-Tat IgG from monkeys injected with 100 (M1) and 10 (M2) μg of recombinant Tat protein, described in FIG. 2. For epitope mapping Elisa were carried out using 8 synthetic peptides corresponding to Tat amino acids (aa) 1-20, 21-40, 36-50, 46-60, 52-72, 56-70, 65-80, 73-86. One hundred microliters of each peptide (10 μg/ml in PBS-A/0.1% BSA) were absorbed onto a PVC 96-well plate for 12 hours at 4° C. Plates were then washed and incubated with 100 μl of PBS-A/3% BSA for 2 hours at 37° C. After incubation, plates were washed with PBS-A/0.05% Tween 20 and then 50 μl of plasma, diluted in PBS-A and 3% BSA, were added to each well. Elisa were then continued as described in FIG. 2. Plasma were obtained at week 37 after the primary immunization. Cut-off values, calculated for each peptide and for each plasma dilution, correspond to the average O.D. of the preimmune plasma in all experiments +3 S.D. (A) shows the average results of plasma diluted 1:50 for each peptide tested in duplicate; (B) shows the antibody titers of plasma shown in (A), expressed as the reciprocal of the highest dilution, at which the test was still positive.

Figure 5:
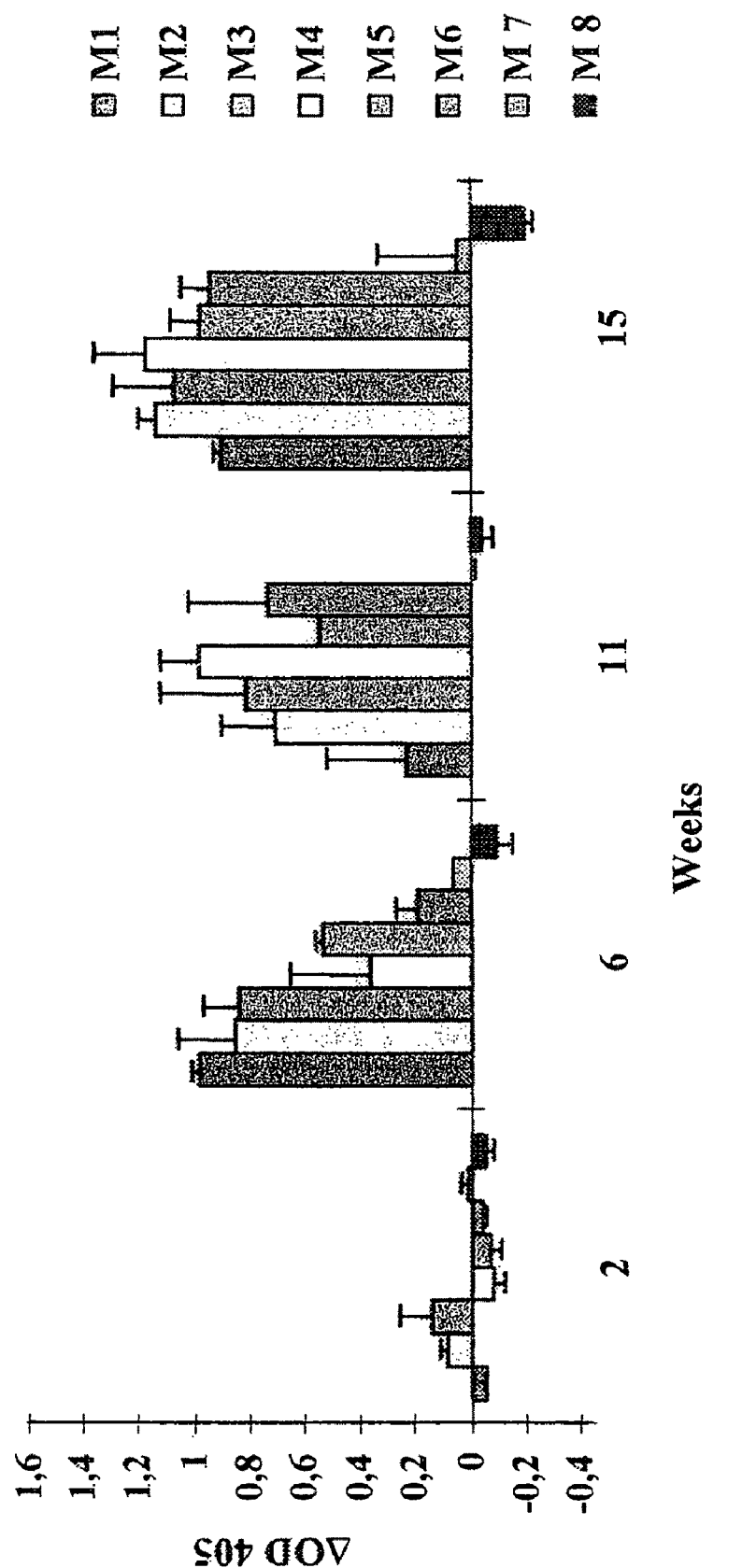
FIG. 5. Analysis of the specific anti-Tat humoral IgM response in monkeys inoculated with Tat protein determined by ELISA.

FIG. 5. Analysis of the specific anti-Tat IgM response in monkeys inoculated with Tat and determined by ELISA. Three monkeys (M1-3) were inoculated subcute with 10 μg of recombinant Tat protein re-suspended in 250 μl autologous serum and 250 μl RIBI; 3 monkeys (M4-6) were inoculated subcute with 10 μg of recombinant Tat protein re-suspended in 250 μl autologous serum and 250 μl is Alum; 2 control monkeys were inoculated subcute with RIBI (250 μl and 250 μl of autologous serum) (M7) or with Alum (250 μl and 250 μl of autologous serum) (M8). The monkeys were inoculated at time 0 and after 2, 6, 11 and 15 weeks. The presence of antibodies was investigated at 2, 6, 11 and 15 weeks. The ELISA method is described in FIG. 2. In this case the plasma of the animals were tested (in duplicate) at 1:100 dilution and an IgM goat anti-monkey serum (diluted at 1:1000) conjugated with horseradish peroxidase was used as the secondary antibody.

The cut-off value was calculated as the average (+2 S.D.) of the O.D. values of the preimmune plasma. Results are the average of the O.D. values (at 405 nm) of two wells subtracted of the cut-off value (ΔO.D. 405).

Figure 6:
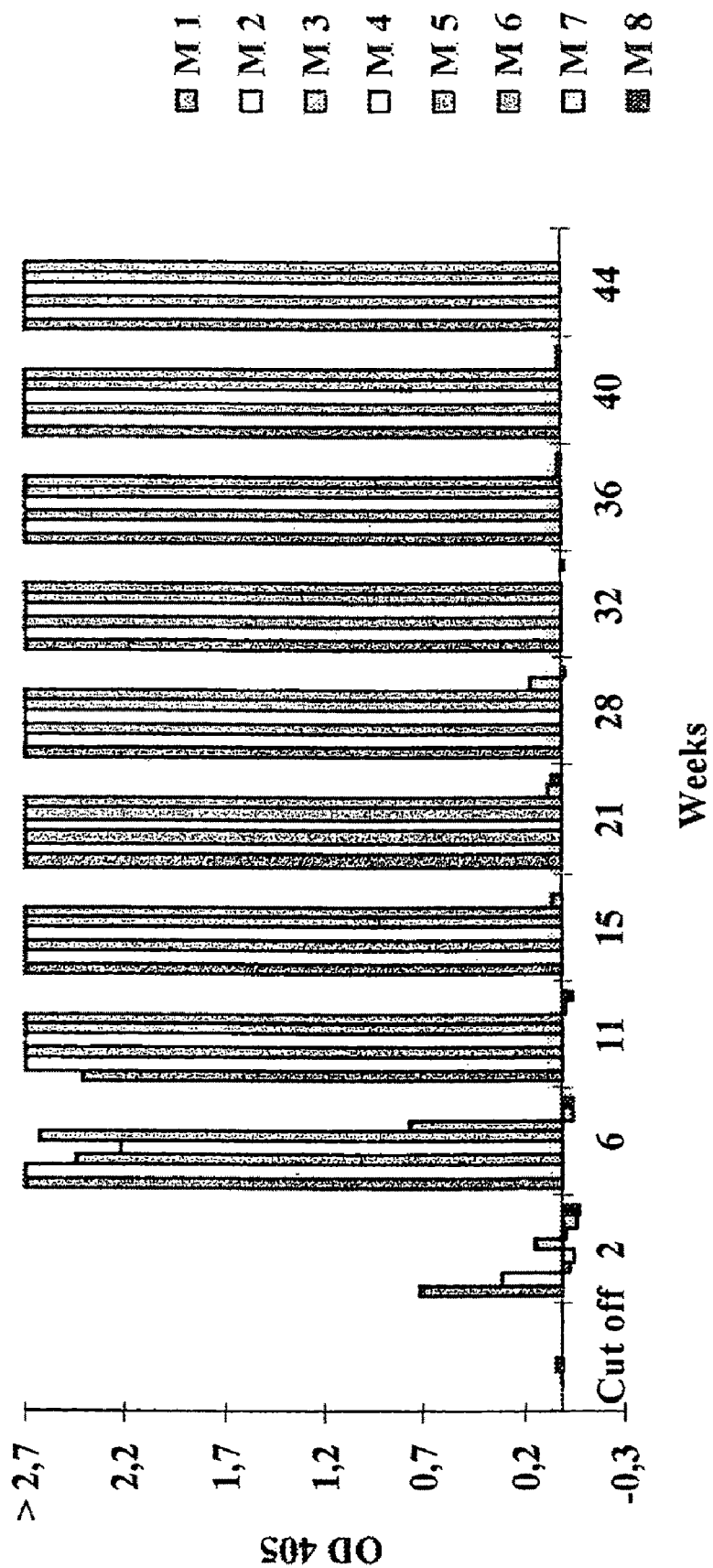
FIG. 6. Analysis of specific anti-Tat IgG production in monkeys inoculated with Tat protein, tested by ELISA.

FIG. 6. Analysis of specific anti-Tat IgG production in monkeys inoculated with Tat, tested by ELISA. Three monkeys (M1-3) were inoculated with 10 μg of recombinant Tat protein re-suspended in 250 μl of autologous serum and 250 μl RIBI; 3 monkeys (M4-6) were inoculated with 10 μg of recombinant Tat protein resuspended in 250 μl autologous serum and 250 μl Alum; two control monkeys were inoculated with RIBI (250 μl and 250 μl of autologous serum) (M7) or with Alum (250 μl and 250 μl of autologous serum) (M8). The monkeys were inoculated at time 0 and after 2, 6, 11, 15, 21, 28 and 32 weeks. At week 36, monkeys M1 to M6 were inoculated with 16 μg of Tat protein resuspended in 200 μl of ISCOMs and 300 μl of PBS. Antibodies were evaluated also at week 40 and 44. The ELISA method and the cut-off value determination are described in FIG. 2. The results shown refer to samples diluted 1:50. >2,7 indicates that the O.D. value was out of scale.

Figure 7:
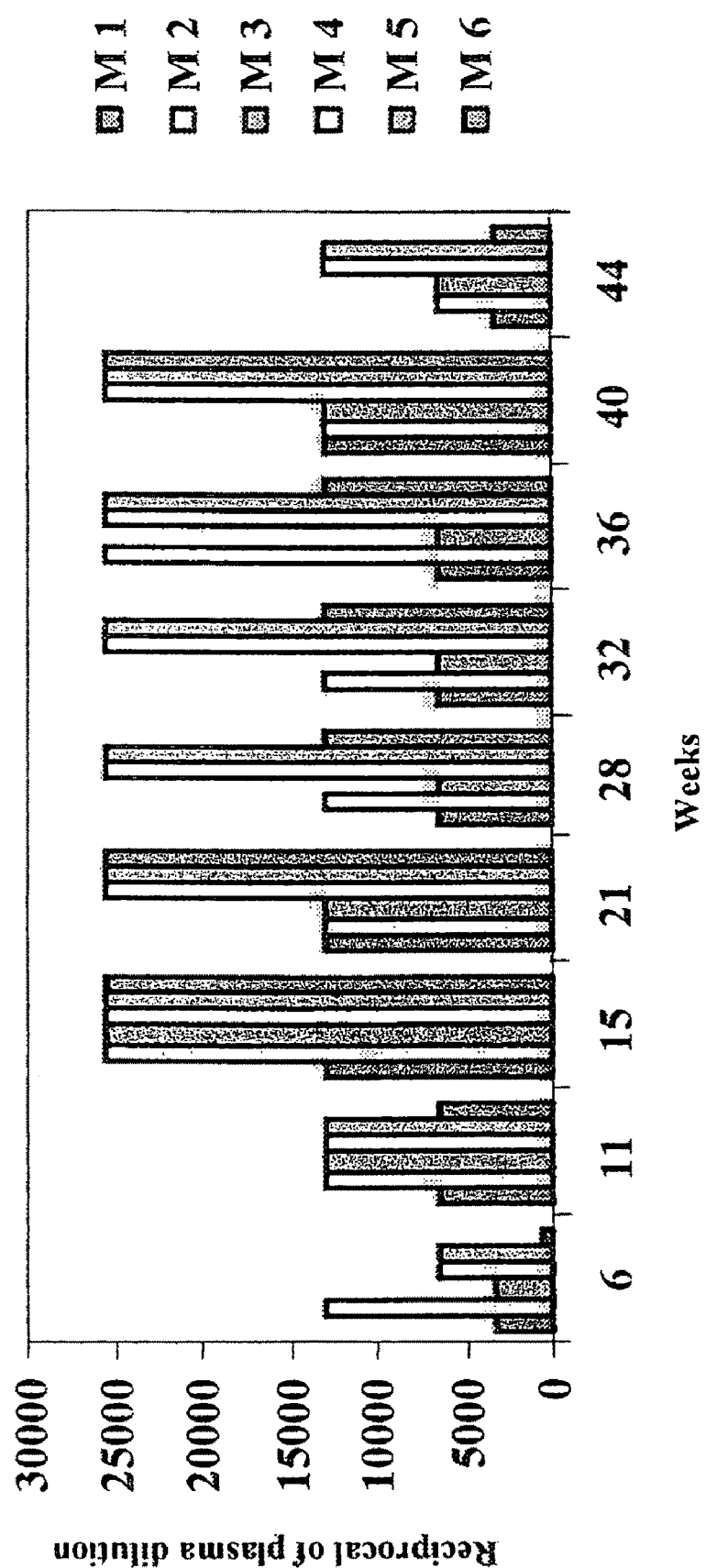
FIG. 7. Titration of anti-Tat antibodies in plasma from the monkeys inoculated with recombinant Tat (10 µg) in the presence of RIBI (M1-3) or Alum (M4-6) described in FIG. 6.

FIG. 7. Titration of anti-Tat antibodies in plasma from the monkeys inoculated with recombinant Tat (10 μg) in the presence of RIBI (M1-3) or Alum (M4-6) described in FIG. 6. The results are shown for each plasma as the inverse of the highest serum dilution at which the test was still positive.

Figure 8A:
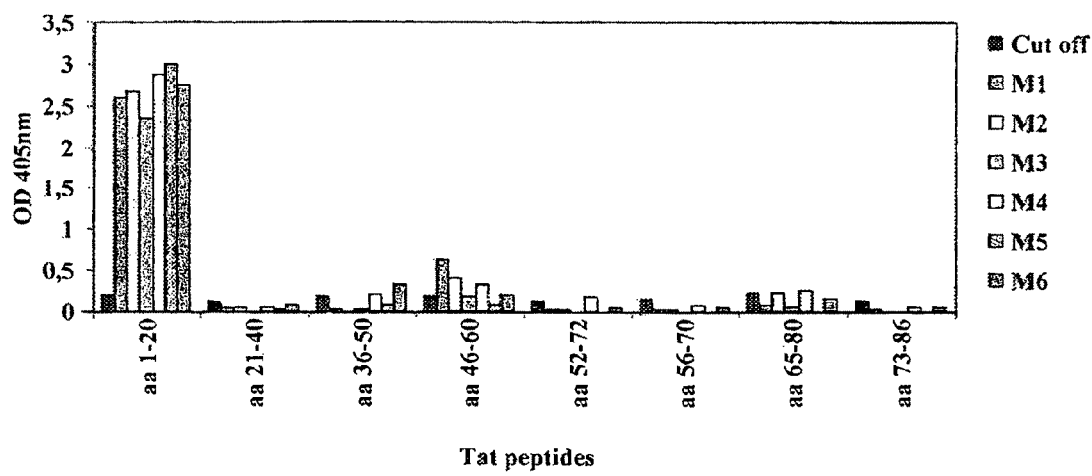
FIG. 8A. Epitopes of Tat recognized by anti-Tat IgG from monkeys inoculated as described in FIG. 6. The results refer to samples diluted 1:50 and are the average from duplicate wells.
Figure 8B:
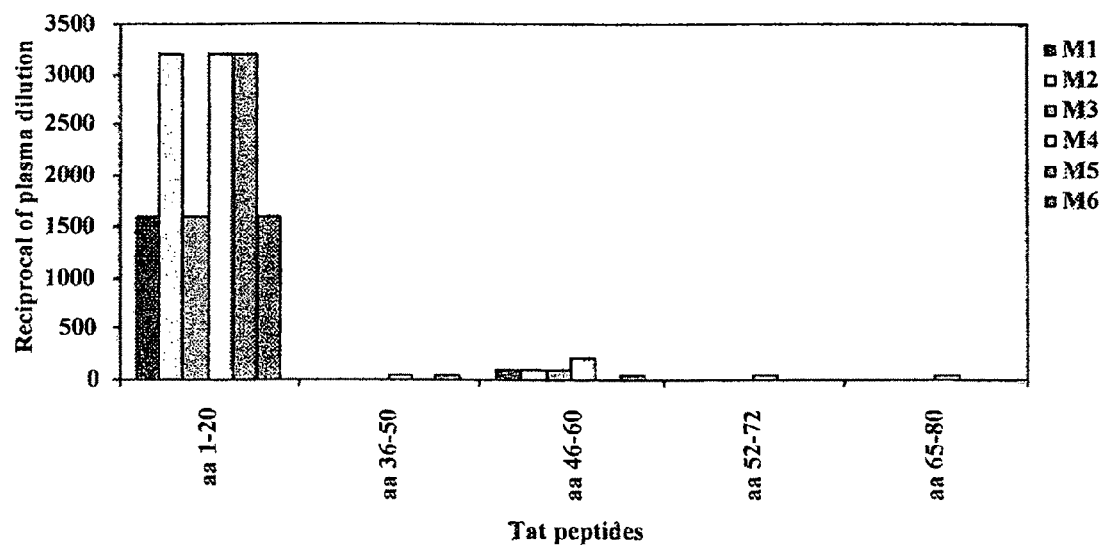
FIG. 8B. Epitopes of Tat according to FIG. 8A. The results refer to the titration of plasma shown in FIG. 8A and are expressed as the highest reciprocal dilution of plasma at which the test was still positive.

FIG. 8. Epitopes of Tat recognized by anti-Tat IgG from monkeys inoculated with recombinant Tat protein (10 μg) in the presence of RIBI (M1 to M3) or Alum (M4 to M6), described in FIG. 6. Plasma were obtained at week 21 after the primary is immunization. The Elisa method and the cut-off determination are described in FIG. 4. Results in (A) refer to samples diluted 1:50 and are the average from duplicate wells. Results in (B) refer to the titration of plasma shown in (A) and are expressed as the highest reciprocal dilution of plasma at which the test was still positive.

Figure 9:
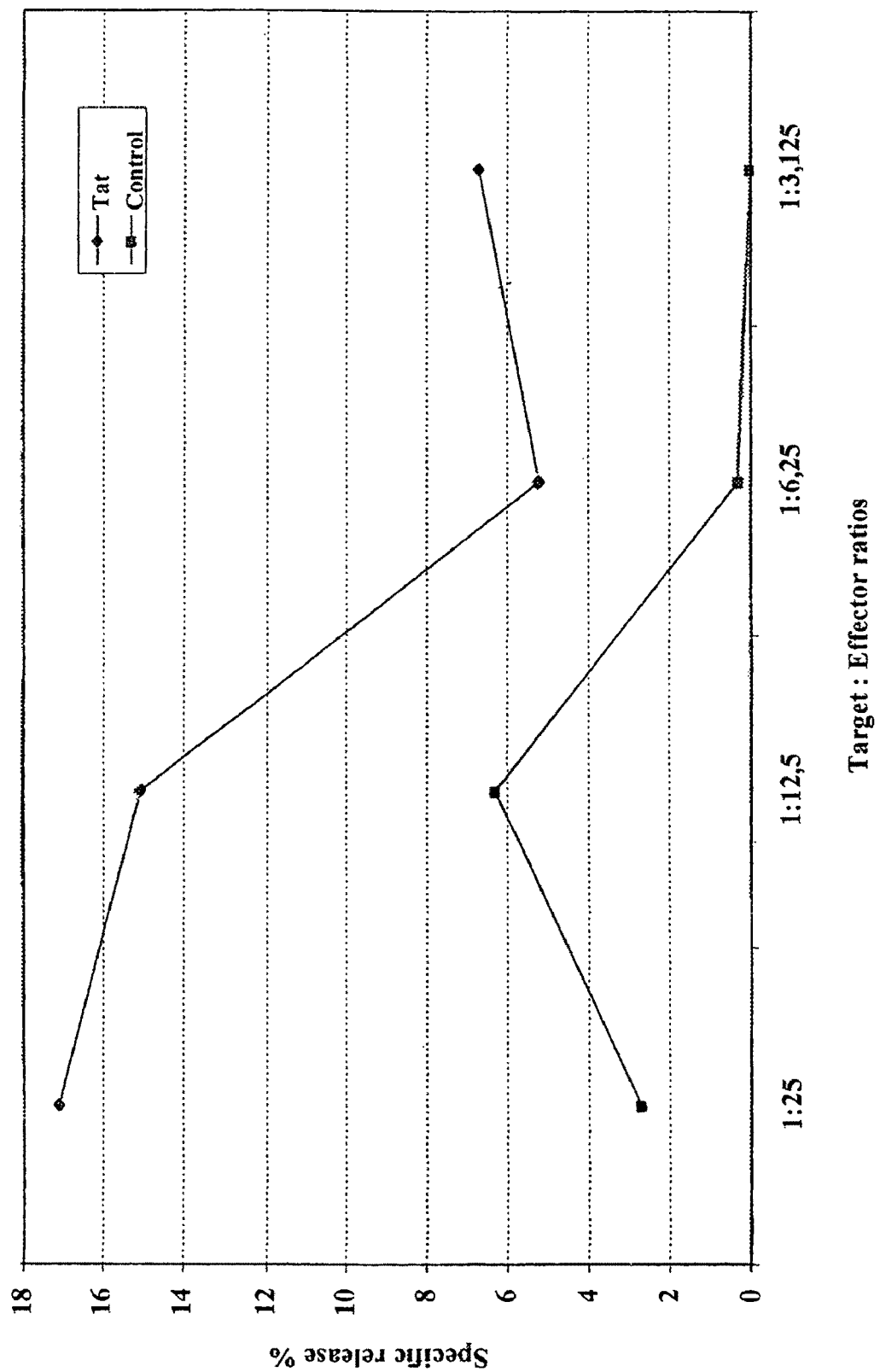
FIG. 9. Analysis of Tat specific CTL.

FIG. 9. Analysis of Tat specific CTL. The assay was carried out as described in Table 5. Shown is an example at the 36$^{th}$ week for monkey M1, injected subcute with 10 μg of Tat and RIBI as described in FIG. 6. Squares (control) correspond to the cells incubated with unpulsed BLCL target cells; rhombs correspond to the cells incubated with the BLCL target cells pulsed with Tat (1 μg/250,000 cells).

Figure 10:
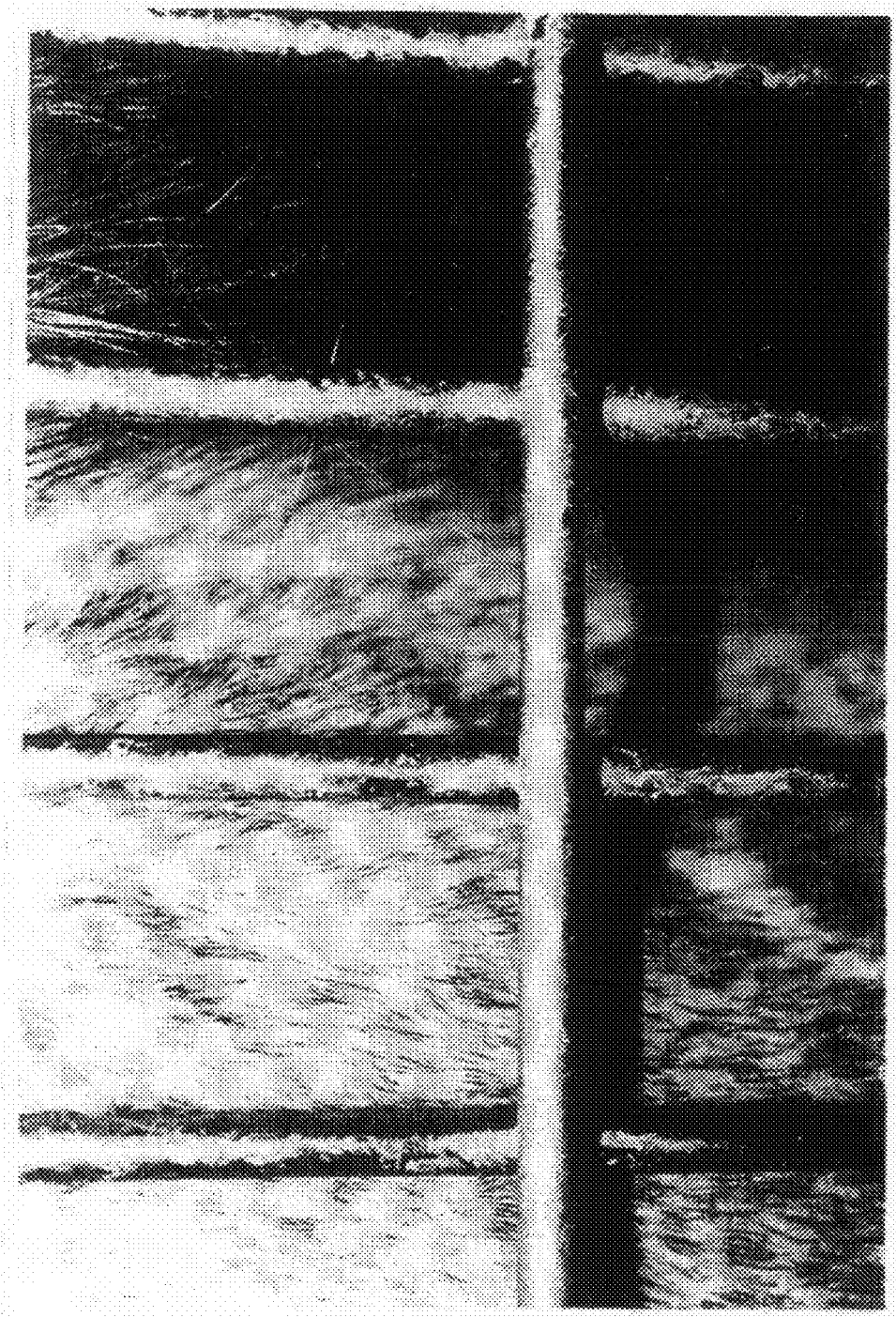
FIG. 10. Analysis of the response of delayed hypersensitivity to Tat by skin test.

FIG. 10. Analysis of the response of delayed hypersensitivity to Tat by skin test. Tat protein (5, 1 and 0.2 μg), resuspended in 150 μl PBS containing 0.1% BSA or the buffer in which Tat was resuspended were inoculated intradermally (i.d.) in a shaved area on the animal back. The area was photographed at time 0 and after 24, 48 and 72 hours. The control monkeys were inoculated only with buffer. Shown is an example of monkey M2 (week 15), inoculated with 10 μg of Tat and RIBI, described in FIG. 6. The positive reaction to Tat was evident at 48 hours after the skin test.

Figure 11A:
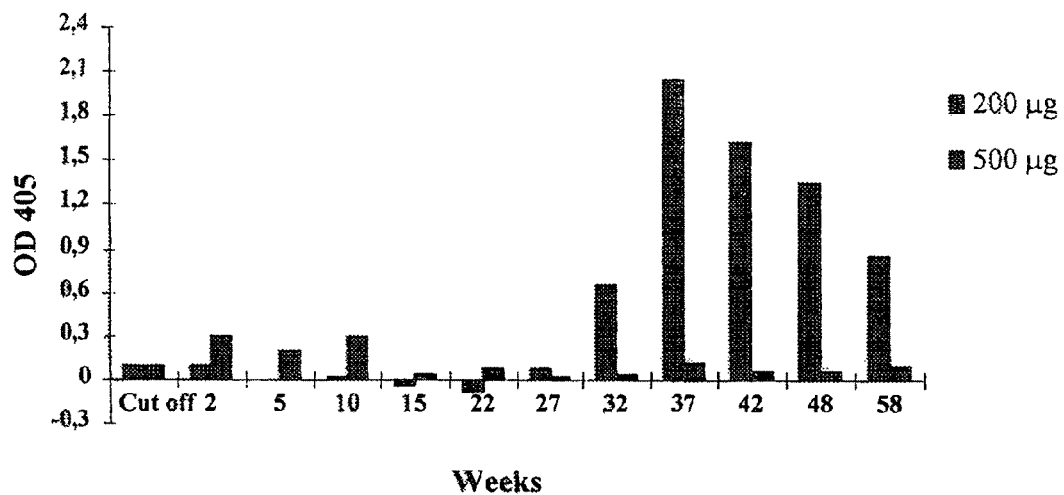
FIG. 11A. Humoral IgG response to Tat in monkeys vaccinated with Tat DNA. There are shown the results obtained from two monkeys vaccinated with 200 (M1) and 500 (M2) µg of pCV-Tat plasmid.
Figure 11B:
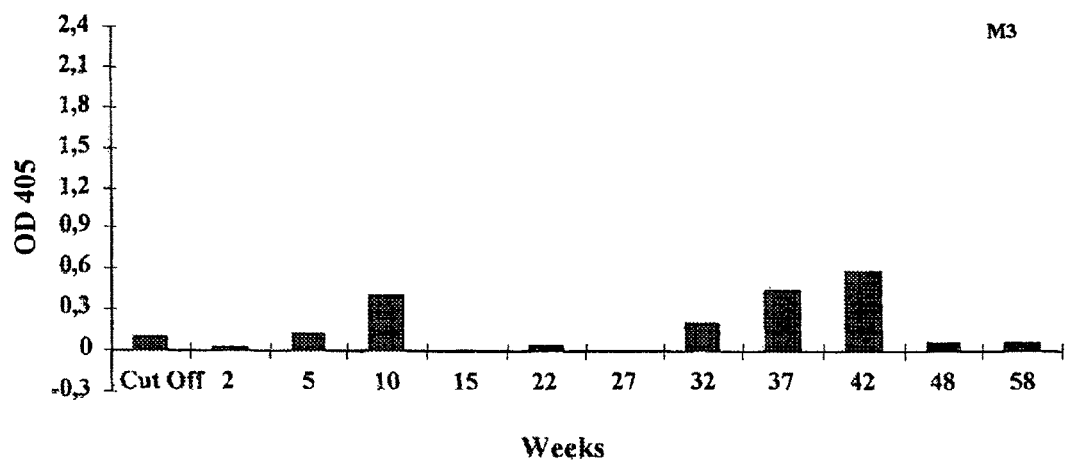
FIG. 11B. Humoral IgG response to Tat in monkeys vaccinated with Tat DNA. Results for the control monkey (M3).

FIG. 11. Humoral IgG response to Tat in one monkey (M1) inoculated i.d. with 200 μg of the pCV-Tat plasmid resuspended in 150 μl of PBS-A, in two sites close to the axillary lymph-nodes; one monkey (M2) was injected with 500 μg of pCV-Tat, resuspended in 250 μl of PBS-A, intramuscular in two sites of the back; the control monkey (M3) was not inoculated with Tat DNA but received, as a control of specificity, repeated skin tests with Tat. Monkeys were injected with pCV-Tat at time 0 and after 5, 10, 15, 22, 27, 32 and 37 weeks. Finally, after 42 weeks, monkeys were boosted with recombinant Tat protein (16 μg) resuspended in 200 μl of ISCOMs and 300 μl of PBS. Antibodies were evaluated at weeks 2, 5, 10, 15, 22, 27, 32, 37, 42, 48 and 58. Anti-Tat antibody response in plasma (diluted 1:50) was analyzed by Elisa as described in FIG. 2. Results are the average ODs of duplicate wells. (A) shows the results obtained from the two monkeys vaccinated with 200 (M1) and 500 (M2) μg of pCV-Tat plasmid. (B) shows the results of the control monkey (M3).

Figure 12:
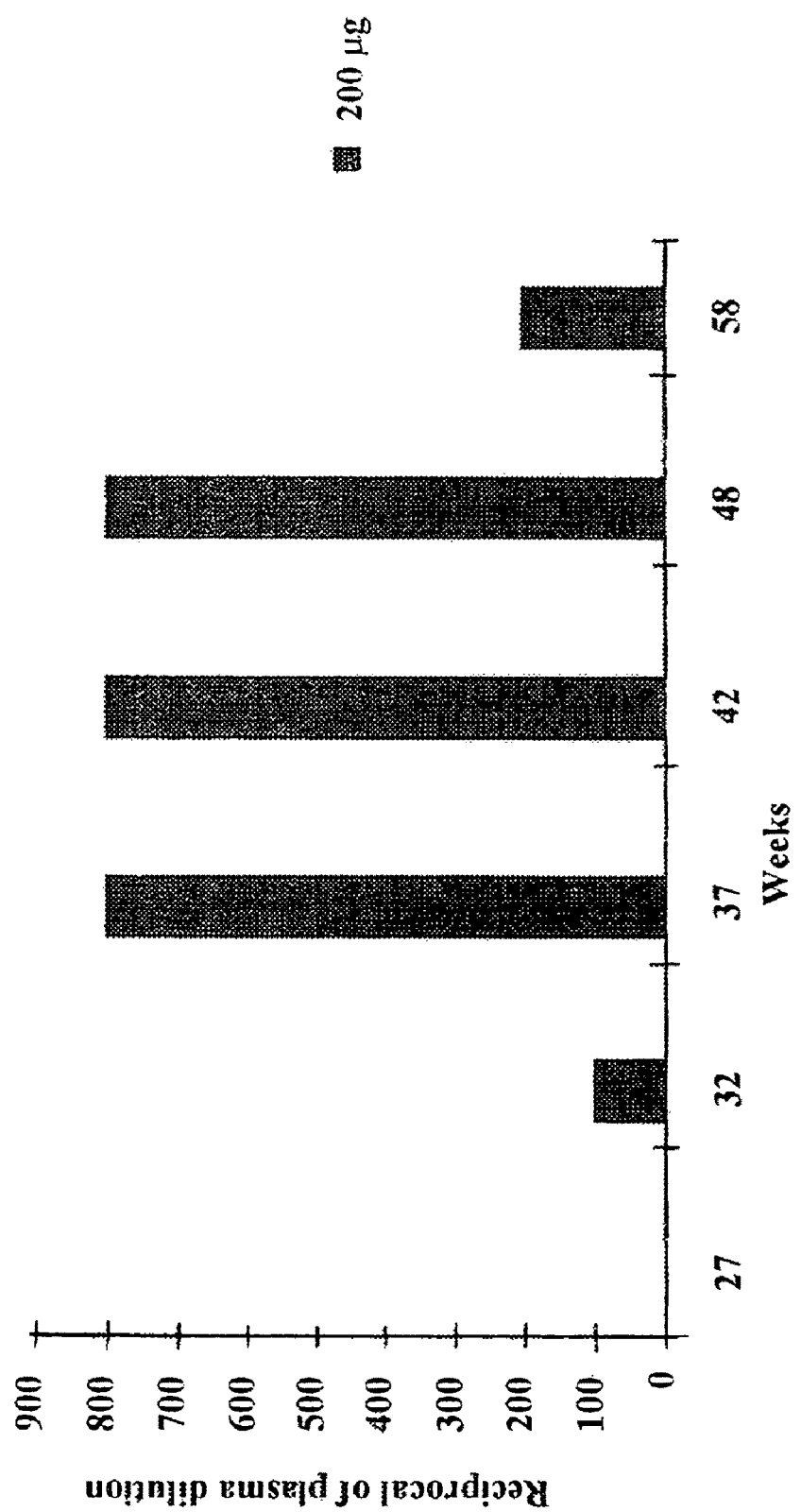
FIG. 12. Titration of anti-Tat antibodies in plasma from monkey M2 inoculated i.d. with 200 µg of pCV-Tat.

FIG. 12. Titration of anti-Tat antibodies in plasma from monkey M2 inoculated i.d. with 200 μg of pCV-Tat. The Elisa is described in FIG. 2. Results in ordinate are expressed as the reciprocal of the highest dilution at which the test was still positive.

Figure 13:
FIG. 13. Analysis of anti-Tat IgG production in three monkeys (M9 to M11) inoculated with 1 mg of pCV-Tat and in one control monkey (M12), inoculated with 1 mg of control vector pCV-0.

FIG. 13. Analysis of anti-Tat IgG production in three monkeys (M9 to M11) inoculated with 1 mg of pCV-Tat and in one control monkey (M12), inoculated with 1 mg of control vector pCV-0. DNA was resuspended in 1 ml of PBS-A and injected intramuscularly in two sites of the back. Monkeys were inoculated at time 0 and after 6, 11, 15, 21, 28 and 32 weeks. At the 36$^{th}$ week monkeys M9 to M11 received a boost with 16 μg of recombinant Tat protein resuspended in 200 μl of ISCOMs and 300 μl of PBS. The presence of anti-Tat antibodies was evaluated at weeks 2, 6, 11, 15, 21, 28, 32, 36, 40 and 44. Elisa and cut-off determination are described in FIG. 2.

Figure 14:
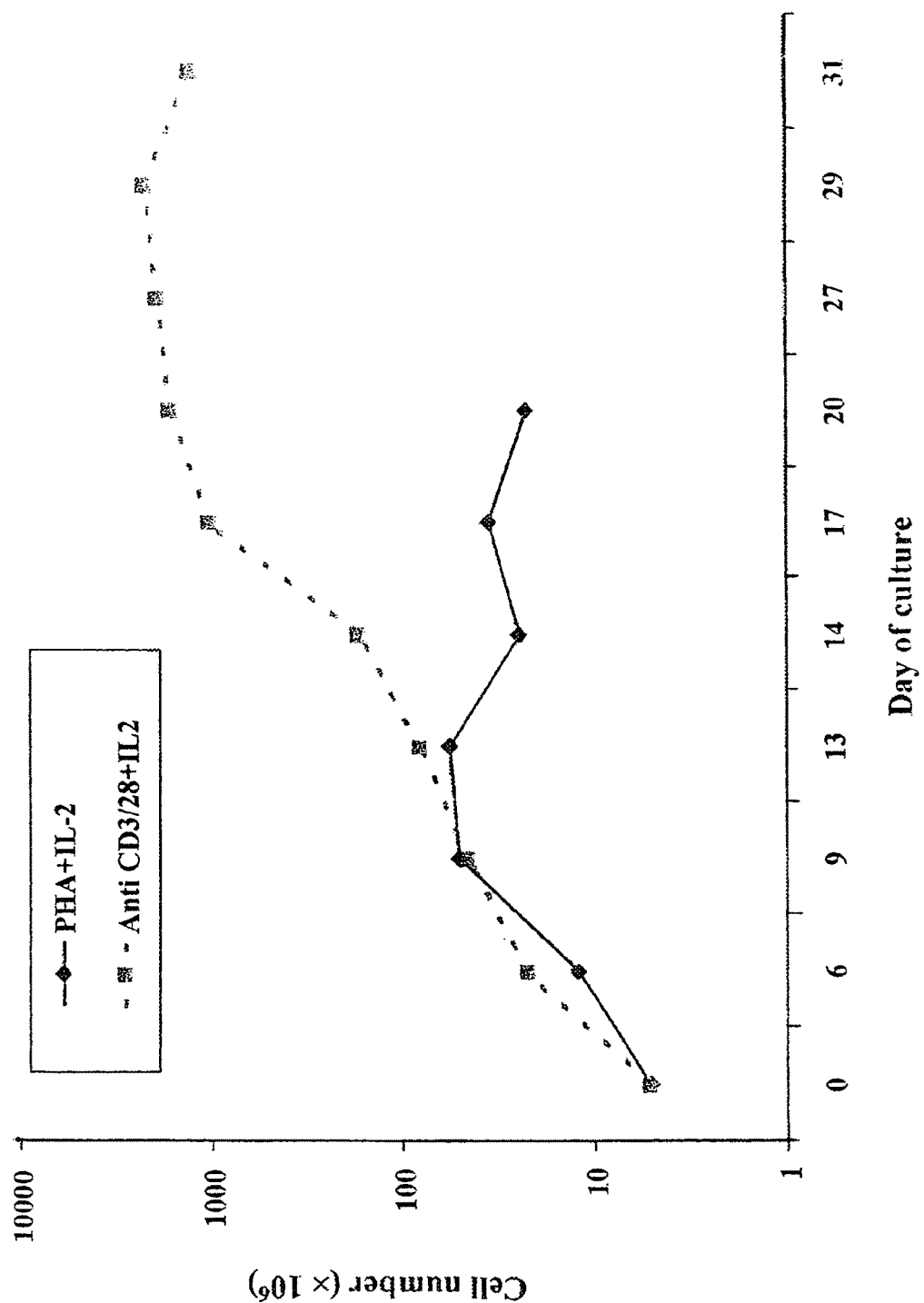
FIG. 14. Kinetics of the proliferative response of PBMC from *Macaca fascicularis* to the co-stimulation with anti-CD3 and anti-CD28 monoclonal antibodies on paramagnetic beads (anti-CD3/28 beads).
Figure 15A:
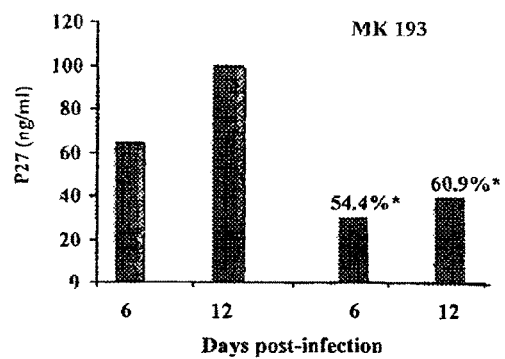
FIG. 15A. Antiviral effect of the co-stimulation with anti-CD3/28 beads on PBMC of *Macaca fascicularis*. Monkey MK 193.
Figure 15B:
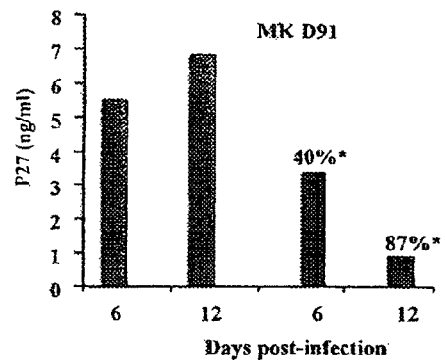
FIG. 15B. Antiviral effect of the co-stimulation with anti-CD3/28 beads on PBMC of *Macaca fascicularis*. Monkey MK D91.
Figure 15C:
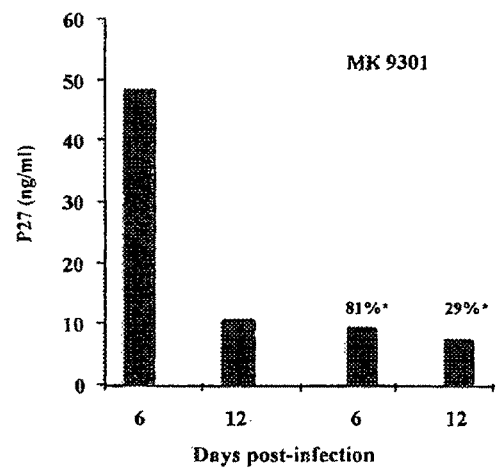
FIG. 15C. Antiviral effect of the co-stimulation with anti-CD3/28 beads on PBMC of *Macaca fascicularis*. Monkey MK 9301.
Figure 15D:
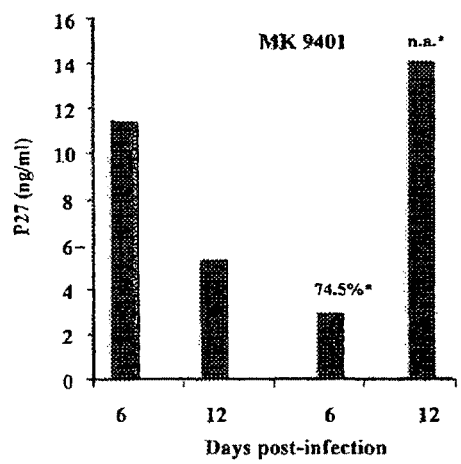
FIG. 15D. Antiviral effect of the co-stimulation with anti-CD3/28 beads on PBMC of *Macaca fascicularis*. Monkey MK 9401.

FIG. 14. Kinetics of the proliferative response of PBMC from *Macaca fascicularis* to the co-stimulation with anti-CD3 and anti-CD28 monoclonal antibodies on paramagnetic beads (anti-CD3/28 beads). The PBMC were depleted of the CD8-positive sub-population by immuno-magnetic methods. Afterwards, half of anti-CD8-depleted lymphocytes was stimulated with PHA and IL-2 (40 U/ml) starting from day 3; the remaining part was left to adhere on the anti-CD3/28-coated beads antibodies, thus obtaining a CD8-depleted and CD3/28 positive lymphocyte population. IL-2 (40 U/ml) was added to this cell fraction starting from day 10 of culture. The cells were counted and their viability was determined each 2-3 days. The beads:cells ratio was maintained constant. The number of cells at different time-points is reported.

FIG. 15. Antiviral effect of the co-stimulation with anti-CD3/28 beads on PBMC of *Macaca fascicularis*. The CD8-depleted and CD8-depleted CD3+/CD28+lymphocytes, obtained from 4 monkeys (FIGS. 15A to 15B) by the methods described in FIG. 14, were stimulated as described in example 7. The two fractions were infected in vitro at the day 0 with 0.1 M.O.I. of SIVmac251/63M. The stimulation was performed with PHA and IL-2, added since day 3, and with is the anti-CD3/28 beads without the addition of exogenous IL-2. Viral production was evaluated by determining the p27 levels (ng/ml) in the cell supernatants at days 6 and 12 after infection as described in example 7. (In light gray PHA$^+$IL$^{-2}$, in dark grey Anti-CD3/28 beads on PBMC CD8$^-$/CD3$^+$/CD28$^+$).

FIG. 16. Functional characterization of dendritic cells (DC) obtained from monkey's peripheral blood. (A) $^3$H-Thymidine incorporation at day 4 of allogeneic mixed leukocyte culture (AMLR) to compare the antigen-presenting-function (APC, determined as the induction of proliferation of allogeneic T cells) of DC and macrophages (Mø) obtained from PBMC of *Macaca fascicularis* after separation on Percoll gradient and adherence on plastic. Non-adherent cells were removed and adherent cells were induced to mature into DC by adding GMCSF (200 ng/ml) and IL-4 (200 units/ml) every 3 days. Half of the culture medium (RPMI, 10% FCS) was removed and substituted with fresh medium every 3 days. After 6-7 days a morphological change of cytokine-induced cells was observed, which acquired a typical DC phenotype (loss of adherence, clustering, fingers), also verified by determining typical membrane markers (data not shown). Monocytes were not cytokine-induced and were cultured in the same medium, that was replaced every 3 days. The cells maintained the monocyte-macrophage characteristics, such as the adherence. At day 7 both cell populations were challenged with T-lymphocytes from a human blood donor, purified by Ficoll and Percoll gradient and by adherence and then frozen. Cell proliferation assays were carried out in a 48-well plate. Five hundred thousand T lymphocytes were stimulated with 5000 DC or Mø (T:APC ratio=100:1). The culture was maintained for 4 days and fixed aliquots of the cell suspension were transferred in 96-well plates, in triplicate. 1 µCi of $^3$H-Thymidine was then added for 16 hours, and the counts per minute (cpm) of the incorporated precursor were determined with a 13-counter.

Figure 16A:
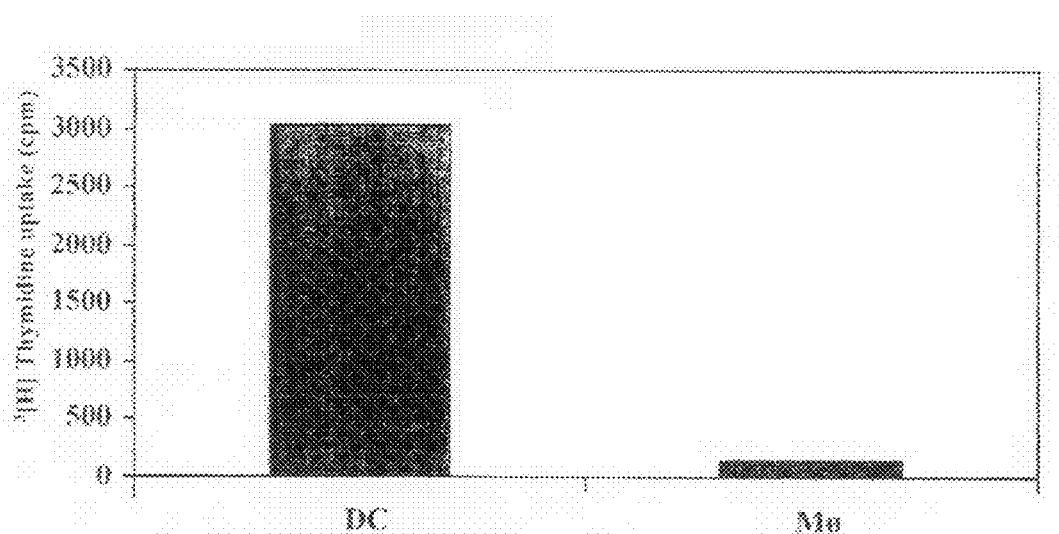
FIG. 16A. Functional characterization of dendritic cells (DC) obtained from monkey's peripheral blood. $^3$H-Thymidine incorporation at day 4 of allogenic mixed leukocyte culture (AMLR).

(B) APCs, such as DC and Mø, obtained as reported in FIG. 16A, were challenged with T lymphocytes from another monkey, obtained as reported above for the human donor. The greater ability to present the antigen is a typical characteristic of the DC as compared to Mø. APCs were added at scalar concentrations to T lymphocytes in order to evaluate the proliferative responses is obtained at different T:APCs (DC or Mø ratios.

The following examples should be considered illustrative and not limitative of the scope of the invention.

Example 1

Expression, Purification and Characterization of the Wild Type Tat Protein (IIIB Isolate), Mutated Tat Proteins and Wild Type Tat Peptides Many difficulties have been encountered in the past to purify and maintain the biological activity of the Tat protein owing to the easiness to oxidate, aggregate and lose activity. This is due to the high amounts of cysteine residues which can form intra- and inter-molecular bonds, thus modifying the conformation of the native protein (Ref. 159, 41). The cDNA or the tat gene (SEQ ID NO:1, example 2), which has been cloned in the pL-syn vector, provided by Dr. J. F. DeLamarter and B. Allet (Glaxo Institute for Molecular Biology S. A., Ginevra, Svizzera), has been used for the expression of the protein in *E. Coli*.

In order to achieve an efficient immunization with Tat for vaccine purposes, the inventor considers fundamental to obtain a biologically active Tat protein as described in the section "Detailed description of the invention". Therefore, the methods of production and purification of Tat, described in this example and in the next examples 1B, 2 and 3, describe necessary procedures and controls to obtain a biologically active Tat protein, which is an effective immunogen to protect from HIV infection, AIDS or from the development of HIV-related diseases.

A first method which we used to obtain an active protein, was based on successive steps of high pressure liquid chromatography and liquid and ion-exchange chromatography (Ref: 15, 41). The protein obtained by these methods is more than 95% pure and it is active (Ref. 41, 42).

However a good reproducibility was not obtained from batch to batch, owing to the protein oxidation, which is the main problem in the commercial Tat preparations. Owing to our observations that the basic region of Tat protein has a strong affinity for heparin and that heparin prevents its oxidation, we used the heparin affinity chromatography and defined a new Tat purification protocol, as described by Chang et al., (Ref. 26). Cells (10 gr. in weight) of *E. coli* expressing Tat were sonicated in 40 ml of lysis buffer (disodium phosphate 20 mM, pH 7.8; glycerol at 2.5%; PMSF 0.2 mM; DTT 5 mM; mannitol 50 mM; ascorbic acid 10 mM; NaCl-500 mM) by using an Ultrasonic Liquid Processor (Model XL2020, Heat System Inc) with three discharges, each one of 20 sec. The lysate was centrifuged at 12,000 g for 30 min. and the supernatant was incubated for one hour at room temperature with 2 ml of heparin sepharose resin, pre-washed with the lysis buffer. The resin was loaded on a glass column and washed with the lysis buffer until the protein was undetectable in the washing medium. The bound material was eluted with lysis buffer containing 2M NaCl and the eluate was collected in fractions of 1 ml. The homogeneity of the eluted protein was analyzed by gel electrophoresis (SDS-PAGE). The purified protein was stored lyophilized at −70° C. and resuspended in a degassed buffer before use.

The biological activity of purified Tat protein, according to the above protocol, was evaluated by a "rescue" assay of viral infection in HLM-1 cells, derived from HeLa-CD4+ cells, containing proviruses defective in the tat gene, obtained and described by Sadaie et al. (Ref. 140). The "rescue" assay of viral infection, described by Ensoli et al. (Ref. 41), consisted in complementing the lack of Tat expression in HLM-1 cells (2×10$^5$) with the addition of exogenous Tat protein (2 µg/ml) and by evaluating viral replication by the determination of the p24 antigen released in the culture medium 48 hours after the addition of the exogenous Tat protein by commercial kits. The results of the "rescue" experiments, described by Chang et al. (Ref. 26), demonstrate that the Tat protein, purified with this method, is active and that this purification method is better, easier and less expensive for both the purity and the biological activity of Tat when compared to the previously described methods (Ref. 40, 41, 42).

Different preparations of recombinant Tat, purified as described above, were inoculated in the presence of Freund's adjuvant in mice and rabbits, according to standard protocols (Ref. 4). The results of the antibody response induced by the immunization are shown in Table 1.

TABLE 1

Analysis of the anti-Tat specific antibody response in sera from mice and rabbits immunized with the recombinant Tat protein.

| anti-Tat Antibody | OD-ELISA/Tat | | | Western Blot |
|---|---|---|---|---|
| | 1:50 | 1:100 | 1:200 | |
| Rabbit | 0.65 | 0.400 | 0.175 | + |
| Mouse | 0.50 | 0.240 | 0.150 | + |

The recombinant Tat protein produced in E. coli was utilized to immunize mice and rabbits according to standard immunization protocols (Ref. 4). The sera of the immunized animals were analyzed by ELISA for the presence of anti-Tat antibodies by using three serum dilutions (1:500 to 1:2000). The results are the mean of the readings at 405 nm of two rabbits and three mice. Moreover, the sera were tested by Western blot with the recombinant Tat protein (100 ng). The results of Table 1 demonstrate that the recombinant Tat, prepared by us, was able to induce an antibody response in both animal species, as tested with ELISA and Western blot which utilizes the recombinant Tat protein. Such antibodies were able to inhibit the internalization and the biological activities of Tat (Ref. 40. 41. 42). The pL-syn vector and the purification protocol of Tat protein are used to express and purify the mutants of Tat described in Example 2. The biological activity of the mutated and purified Tat proteins is measured by "rescue" assays of viral infection in HLM-1 cells, assays of proliferation of KS cells and in vivo in mice, as described above for the wild-type Tat protein. Moreover, the mutated Tat proteins are tested in the presence of wild-type Tat (at serial concentrations) to verify the negative transdominant effect on viral replication. The pL-syn vector and the purification protocol are used to express and purify fusion proteins of this type: Tat (wild type or mutants thereof)/IL-12 or Tat (wild type or mutants thereof)/IL-15 or parts of the same or Tat (wild type or mutants thereof)/other molecules (or parts thereof) able to enhance the immune response to Tat alone or associated with other viral products. Fusion recombinant molecules are made by utilizing the sequences and the primers described in examples 2 and 3. As an alternative, synthetic peptides, corresponding to regions of Tat or of other viral products or of cytokines to be used in combination with Tat are utilized as immunogens. The peptide sequences of Tat are:

Pep. 1. MEPVDPRLEPWKHPGSQPKT SEQ. ID. NO. 11

Pep. 2. ACTNCYCKKCCFHCQVCFIT SEQ. ID. NO. 12

Pep. 3. QVCFITKALGISYGRK SEQ. ID. NO. 13

Pep. 4. SYGRKKRRQRRRPPQ SEQ. ID. NO. 14

Pep. 5. RPPQGSQTHQVSLSKQ SEQ. ID. NO. 15

Pep. 6. HQVSLSKQPTSQSRGD SEQ. ID. NO. 16

Pep. 7. PTSQSRGDPTGPKE SEQ. ID. NO. 17

The Tat mutant peptides will contain the same amino acid substitutions of the mutated Tat proteins, described in the Example 2. The peptides will be utilized in combination with the peptide representing the universal T-helper epitope of the tetanous toxoid or with other peptides representing T-helper epitopes (Ref. 77).

Example 1A

Uptake of Picomolar Concentrations (10 to 100 ng/ml) of Biologically Active Tat by Activated Endothelial Cells is Mediated by Integrin Receptors When normal endothelial cells are activated in vitro with inflammatory cytokines, they become responsive to the effects of extracellular Tat and this is due to the induction of the $\alpha_5\beta_1$ and $\alpha_v\beta_3$ integrins (Ref. 9, 10). Similarly, inflammatory cytokines (IC) or bFGF increase integrin expression on endothelial cells in vivo and this leads to a synergistic KS-promoting effect when a biologically-active Tat is inoculated in mice simultaneously or after bFGF (Ref. 42). In addition, IC-activated endothelial cells acquire APC function.

In this example it is shown that endothelial cells activated with IC take up rhodaminated biologically-active Tat protein more efficiently and that this is mediated by the integrin receptors.

Because of the difficulty in observing the internalization of very low concentrations of cold Tat, the protein was labeled with rhodamin (Ref. 98). The rhodaminated Tat still showed activation of KS cell proliferation in the same concentration range as unlabelled Tat, indicating that the labeling procedure did not compromise its biological function. Tat uptake experiments were performed as follows: human umbilical vein (HUVE) cells were grown and treated for 5 days with IC as described (Ref. 9, 46). The cells were then trypsinized, plated on 8 well slides (Nunc Inc., Naperville, Ill.) at $0.5 \times 10^5$ cells per well and incubated for 18 hours in medium containing 15% fetal bovine serum (FBS), in the presence of IC. Serum free (SF, RPMI, 1% BSA, 0.1% antibiotics, fungizon) media were added and slides were pre-incubated for 2 h at 4° C. Fresh medium, containing serial dilution of rhodaminated Tat, was added to the cells and the cells were incubated at 37° C. for the time indicated. Negative controls were rhodaminated BSA in the same buffer as Tat. Cells were fixed in ice-cold acetone-methanol (1:1) and uptake and localization of Tat visualized and photographed using fluorescence microscopy. Results were evaluated by comparing the fluorescence of samples with the negative control and scored from 0 to ++++ on the amount of uptake without prior knowledge of sample code.

To investigate the pathways by which Tat is taken up by activated endothelial cells, experiments were carried out using activated HUVE cells with a wide range of concentrations of exogenous Tat, such as those previously used to induce HUVE or KS cell growth (10-50 ng/ml), or HIV-1 transactivation by adding the protein to cells carrying the HIV-1 promoter or the provirus (0.5 to 1 ug/ml). In these experiments, for consistency with uptake inhibition experiments (see below), cells were pre-incubated at 4° C. for 2 hours with medium lacking fetal calf serum. This pre-incubation does not affect the subsequent uptake of rhodaminated Tat.

With rhodaminated Tat, the uptake and translocation of the protein to the nucleus or nucleoli of activated HUVE cells began to be evident within 15 minute incubation with as low as 10 ng/ml rhodaminated Tat. The density of uptaken Tat in the cells was increased in a dose-dependent and time-dependent manner. Rhodaminated BSA or buffer showed no signals and were used routinely as negative controls.

To determine whether uptake of Tat by activated HUVE cells was mediated by the same integrins found expressed on KS cells, inhibition experiments were performed by pre-incubating IC-activated endothelial cells with cold Tat (competitor), the physiological ligands for these receptors such as fibronectin (FN) or vitronectin (VN), or by pre-incubating the cells with monoclonal antibodies directed against the RGD binding regions of the $\alpha_5\beta_1$ and $\alpha v\beta_3$ receptors. The experimental procedure is briefly reported. After plating on 8 well slides, HUVE cells were incubated with medium containing 15% FBS for 18 h and then incubated with SF medium containing unlabelled Tat (cold competitor) (Table 1A), FN, VN (Table 1B), or monoclonal antibodies directed against the RGD binding sequence of the FN or VN receptors ($\alpha_5\beta_1$ and $\alpha_v\beta_3$, respectively), or monoclonal antibodies directed against human factor VIII (control antibodies) (FIG. 1A) for 2 h at 4° C. The cells were then incubated with rhodaminated Tat for the periods of time indicated. The control consisted of cells treated with SF medium alone for 2 h at 4° C. and incubated with rhodaminated BSA. The cells were fixed, visualized, photographed and results scored as indicated above.

TABLE 1A

Inhibition of uptake of 100 ng/ml and 1 µg/ml rhodaminated Tat by cytokine-activated HUVE by pre-incubation of the cells with 1 µg/ml of unlabelled Tat.[a]

| Pre-incubation | Rhodaminated Tat | Uptake of Tat |
|---|---|---|
| Serum Free Medium | 100 ng/ml | +++ |
| 1 µg/ml Unlabelled Tat | 100 ng/ml | +/− |
| Serum Free Medium | 1 µg/ml | ++++ |
| 1 µg/ml Unlabelled Tat | 1 µg/ml | +/− |

[a]HUVE cells were cultured as previously described (Ref. 40). IC were obtained from human T-lymphotrophic virus-type-II (HTLV-II) transformed CD4[+] T cells or phytohemagglutinin-stimulated T cells and the supernatants used (1:8) to activate HUVE cells (passage 8-14) for 5 days as previously described (Ref. 9, 46). This supernatant contains interleukin-1α (IL-1α) and -β (IL-1β), tumor necrosis factor-α (TNF-α) and -β (TNF-β), and interferon-γ (IFN-γ), (Ref 9).

Tat protein was rhodaminated at lysine residues essentially as described (Ref. 98). Briefly, 50 µg recombinant Tat (2 mg/ml), was brought to pH 9.0 by the addition of 2.5 µl of 1M $Na_2CO_3$. Two point five µl of 1 mg/ml TRITC in dimethylsulfoxide (DMSO) was added and the reaction allowed to proceed for 8 hr at 4° C. Unreacted TRITC was quenched by the addition of 2.5 µl of 0.5M $NH_4Cl$, the pH was lowered to 7.0, using 1M HCl, and the rhodaminated Tat was dialyzed against two changes of 50 mM Tris-HCl, pH 7.0, 1 mM dithiothreitol (DTT) to remove the quenched TRITC. BSA or PBS, rhodaminated in the same way, were used as negative controls. Rhodaminated Tat was tested for AIDS-KS cells growth activity as described to insure that biological activity was maintained (Ref. 40). HUVE cells were pre-incubated for 2 hours with serum free medium or 1 µg/ml unlabelled Tat in serum free medium, incubated with 100 ng/ml or 1 µg/ml rhodaminated Tat for 60 minutes and Tat uptake visualized by fluorescence microscopy. Negative controls (+/−uptake) were preincubation with serum free medium, followed by incubation with rhodaminated BSA.

TABLE 1B

Inhibition of the uptake of 10 ng/ml rhodaminated Tat by cytokine-activated HUVE by pre-incubation of the cells with an excess of FN or VN[a].

| Pre-incubation | Uptake of Rhodaminated Tat |
|---|---|
| Serum Free Medium | ++++ |
| 100 ng/ml FN | +/− |
| 100 ng/ml VN | +/− |

[a]HUVE cells were pre-incubated for 2 hours with serum free medium or FN or VN in serum free medium, incubated with 10 ng/ml rhodaminated Tat for 60 minutes and Tat uptake visualized by fluorescence microscopy. Negative controls (+/− uptake) were pre-incubation with serum-free medium, followed by incubation with rhodaminated BSA.

Uptake of Tat was inhibited by cold Tat (Table 1A), by FN or VN (Table 1B) or by prior treatment of the cells with monoclonal antibodies directed against the RGD binding regions of both the FN receptor, $α_5β_1$, and the VN receptor, $α_vβ_3$ (FIG. 1A). The intensity of fluorescence in cells was reduced to levels seen with the negative control and no inhibition was observed by prior incubation of the cells with monoclonal antibodies directed against human factor VIII, used as negative control, indicating that inhibition was specific (FIG. 1A).

Uptake and nuclear localization of 100 ng/ml Tat was inhibited by pre-incubation of the cells with the monoclonal antibodies directed against the RGD binding region of the $α_5β_1$ receptor and the $α_vβ_3$ receptor. However, in both instances inhibition was not complete. These results indicate that uptake of picomolar concentrations of Tat is mediated by the same integrins involved in cell adhesion to Tat (Ref. 10). However, at higher concentration of extracellular Tat (such as ≧100 ng/ml), a non-integrin mediated pathway is responsible for the uptake of some of the protein.

In contrast with these results, the uptake of iodinated Tat with lymphocyte and epithelial cell lines was shown to be linear and in function of the concentration of Tat in the medium and was not or poorly competed by an excess of cold Tat, indicative of the lack of receptor involvement (Ref. 98). However, the concentration range of Tat in the medium in that study was approximately 1-100 µg/ml (Ref. 98), much higher than those needed to observe uptake of Tat by cells responsive to its biological activity, such as activated primary endothelial cells. In addition, iodination of Tat may hamper its structure and its uptake by the cells and no results of biological activity of iodinated Tat were shown by those authors.

These results, that are unpublished, demonstrate that the uptake of Tat occurs by at least two pathways depending upon the concentration of the protein. At low (10-100 ng/ml) Tat concentrations, uptake of Tat is mediated by the $α_5β_1$ and $α_vβ_3$ receptors through the interaction with the RGD sequence of the protein, whereas at higher concentration of extracellular Tat an integrin-independent pathway is more important. The integrin-mediated uptake of picomolar concentrations of Tat by IC-activated endothelial cells indicates a fully active protein capable of entering antigen presenting cells, such as activated endothelial cells and dendritic cells, that initiate the immune response.

Example 2

Construction and Characterization of Mutated Tat Genes

We produced 19 mutants in different Tat regions by means of site specific mutagenesis or by deletion. The sequence of each mutated DNA was controlled by sequencing. The cDNAs of the tat mutated genes were cloned in the PstI site of the pCV0 vector, described in the Example 3. Each mutant was co-transfected, as described by Ensoli et al. (Ref. 41) in COS-1 cells or in the Jurkat T-cell line with the HIV-1 LTR-CAT plasmid, in which the CAT reporter gene is driven by the HIV-1 LTR. The results of these experiments, not published, are reported in Table 2.

TABLE 2

Effect of Tat mutants on the HIV-1 LTR-CAT transactivation and blocking effect (negative transdominant) on the Tat wild-type activity

| | Transactivating activity[a] | | Transdominant activity[b] (% inhibition) |
|---|---|---|---|
| MUTANTS | Mean (fold) | (min-max values) | Mean |
| CYS 22 | 0.09 | (0.021-0.22) | 21 |
| THR 23 | 0.36 | (0.16-1  ) | |
| THR 23A | 0.30 | (0.16-0.78) | |
| ASN 24 | 0.34 | (0.34-0.82) | |
| ASN 24A | 0.42 | (0.45-0.95) | |
| TYR 26 | 0.14 | (0.08-0.19) | |
| LYS 28/29 | 0.52 | (0.19-1.04) | |
| CYS 30 | 0.30 | (0.045-0.65) | |
| CYS 31 | 0.60 | (0.27-1.09) | |
| PHE 32 | 0.31 | (0.077-0.097) | |
| LYS 33 | 0.04 | (0.0027-0.068) | 46 |
| GLU 35 | 0.31 | (0.19-0.43) | |

TABLE 2-continued

Effect of Tat mutants on the HIV-1 LTR-CAT transactivation and blocking effect (negative transdominant) on the Tat wild-type activity

| MUTANTS | Transactivating activity[a] | | Trans-dominant activity[b] (% inhibition) |
|---|---|---|---|
| | Mean (fold) | (min-max values) | Mean |
| PHE 38 | 0.05 | (0.043-.057) | 98 |
| LYS 41 | 0.04 | (0.025-0.061) | 97 |
| TYR 47 | 0.58 | (0.31-0.8) | |
| 57 A | 0.35 | (0.26-0.44) | |
| TAT-RGD | 0.94 | (0.73-1.15) | |
| TAT-KGE | 1.11 | (0.67-1.49) | |
| TAT wild-type | 1 | | 1 |

[a]The results are given as the increment of activation of CAT activity values induced by the wild-type Tat (Fold = 1).
[b]The results are expressed as percent (%) inhibition of the wild-type Tat activity.

From the results presented in Table 2 it is evident that for the majority of the mutants the transactivating effect of the HIV-1 LTR was reduced or absent, with the exception of the RGD mutant, which had an activity similar to wild-type Tat. We selected the 4 mutants (cys22, lys33, phe38, lys41) having the lowest (almost zero) transactivating activity and determined the negative transdominating effect on the transactivating activity of wild-type Tat. To this end, COS-1 cells were co-transfected with each vector containing a Tat mutant and the pCV-Tat vector (in a molar ratio of 10:1) in the presence of the HIV-1 LTR-CAT vector. As shown in Table 2, the lys41 and tyr47 mutants inhibited almost completely Tat activity, while the lys33 and cys22 mutants partially inhibited the Tat activity. However, the cys22 recombinant protein (described in following Example 3) competed the wild-type Tat protein in transactivating the HIV-1 LTR-CAT (FIG. 1B). A mutant in the cysteine region (cys22), one in the core region (lys41), one deleted of the RGD sequence (RGDΔ) and a double mutant containing the mutation in lys41 and the deletion of the RGD sequence (lys41-RGDΔ) were selected.

The sequence of the tat insert and of the mutants selected for the vaccination is reported hereinafter. A series of tat mutants is described prepared by 1) substitution of a base to obtain an amino acid substitution and 2) deletion of a base to obtain a deletion of the correspondent amino acids. The substitutions and deletions were obtained by site direct mutagenesis. The sequences of the wildtype tat gene and of the tat gene mutants, hereinafter reported, were inserted in the pCV0 plasmid vector as described above.

With SEQ ID NO:1 it is intended the HIV-1 tat gene sequence, from BH-10 clone and its derived protein (SEQ ID NO:2). With SEQ ID NO:3 it is intended the cys22 mutant sequence (and its derived protein, SEQ ID NO:4), represented by a substitution of Thymine (T) nucleotide in position 64 starting from the 5' end with the Guanine (G) nucleotide. This substitution originates, in the derived amino acid sequence, a substitution of a Cysteine (C in one letter code) in position 22 at the amino-terminal end, with a Glycine (G in one letter code). With SEQ ID NO:5 it is intended the lys41 mutant sequence (and its derived protein, SEQ ID NO:6), represented by a substitution of the Adenine (A) nucleotide in position 122 from the 5' end with the Cytosine (C) nucleotide. This substitution originates, in the derived amino acid sequence, a substitution of a Lysine (K in one letter code) in position 41 from the amino-terminal end, with a Threonine (T in one letter code). With SEQ ID NO:7 it is intended a sequence of the RGD mutant (and its derived protein, SEQ ID NO:8), represented by the deletion of the nucleotide sequence CGAGGGGAC, from nucleotide 232 to nucleotide 240, starting from the 5' end of the wild-type gene. This gives a deletion of the amino acids Arginine-Glycine-Aspartic acid (RGD in one letter code) in the positions 78-80 from the amino-terminal end. With SEQ ID NO:9 it is intended a sequence of the double lys41-RGDΔ mutant (and its derived protein, SEQ ID NO:10), originated by the combination of the above described mutants.

Wild-type tat Nucleotide Sequence SEQ. ID. NO. 1

5'ATGGAGCCAGTAGATCCTAGACTAGAGC-
CCTGGAAGCATCCAGGAAGTCA    GCCTAAAACT-
GCTTGTACCAATTGCTATTGTAAAAAGT-
GTTGCTTTCATTGCCA
AGTTTGTTTCATAACAAAAGCCTTAG-
GCATCTCCTATGGCAGGAAGAAGCGG    AGACAGC-
GACGAAGACCTCCTCAAGGCAGTCA-
GACTCATCAAGTTTCTCTAT
CAAAGCAGCCCACCTCCCAATC-
CCGAGGGGACCCGACAGGCCCGAAGGAATAG 3'

Amino Acid Sequence SEQ. ID. NO. 2

NH2-MEPVDPRLEPWKHPGSQPKTACTNCYCK-
KCCFHCQVCFITKALG    ISYGRKKRRQRRRPPQG-
SQTHQVSLSKQPTSQSRGDPTGPKE-COOH

Cys22 Mutant Nucleotide Sequence SEQ. ID. NO. 3

5'ATGGAGCCAGTAGATCCTAGACTAGAGC-
CCTGGAAGCATCCAGGAAGTCA  GCCTAAAACTGC
TGGTACCAATTGCTATTGTAAAAAGTGTTGCTTTCATTGCCA
AGTTTGTTTCATAACAAAAGCCTTAG-
GCATCTCCTATGGCAGGAAGAAGCGG    AGACAGC-
GACGAAGACCTCCTCAAGGCAGTCA-
GACTCATCAAGTTTCTCTAT
CAAAGCAGCCCACCTCCCAATC-
CCGAGGGGACCCGACAGGCCCGAAGGAATAG 3'

Amino Acid Sequence SEQ. ID. NO.4

NH2-MEPVDPRLEPWKHPGSQPKTAGTNCYCK-
KCCFHCQVCFITKA    LGISYGRKKRRQRRRPPQG-
SQTHQVSLSKQPTSQSRGDPTGPKE-COOH

Lys41 Nucleotide Sequence SEQ. ID. NO. 5

5'ATGGAGCCAGTAGATCCTAGACTAGAGC-
CCTGGAAGCATCCAGGAAGTCA    GCCTAAAACT-
GCTTGTACCAATTGCTATTGTAAAAAGT-
GTTGCTTTCATTGCCA    AGTTTGTTTCATAACAA
CAGCCTTAGGCATCTCCTATGGCAGGAAGAAGCGG
AGACAGCGACGAAGACCTCCTCAAG-
GCAGTCAGACTCATCAAGTTTCTCTAT    CAAAG-
CAGCCCACCTCCCAATCCCGAGGGGAC-
CCGACAGGCCCGAAGGAATAG 3'

Amino Acid Sequence SEQ. ID. NO. 6

NH2-MEPVDPRLEPWKHPGSQPKTACTNCYCK-
KCCFHCQVCFIXALG    ISYGRKKRRQRRRPPQG-
SQTHQVSLSKQPTSQSRGDPTGPKE-COOH

RGDΔ Mutant Nucleotide Sequence SEQ. ID. NO. 5

5'ATGGAGCCAGTAGATCCTAGACTAGAGC-
CCTGGAAGCATCCAGGAAGTCA    GCCTAAAACT-
GCTTGTACCAATTGCTATTGTAAAAAGT-
GTTGCTTTCATTGCCA
AGTTTGTTTCATAACAAAAGCCTTAG-
GCATCTCCTATGGCAGGAAGAAGCGG    AGACAGC-
GACGAAGACCTCCTCAAGGCAGTCA-
GACTCATCAAGTTTCTCTAT

CAAAGCAGCCCACCTCCCAATCCCCGA-
CAGGCCCGAAGGAATAG 3'

Amino Acid Sequence SEQ. ID. NO. 8

NH2-MEPVDPRLEPWKHPGSQPKTACTNCYCK-
KCCFHCQVCFITKALG ISYGRKKRRQRRRPPQG-
SQTHQVSLSKQPTSQSPTGPKE-COOH pCV0-Tat vector (Ref. 5) was obtained by cloning the cDNA in the pCV0 PstI site, driven by the AdMLP. The choice of this vector is based on that the AdMLP induced a higher expression and release of Tat, with respect to other eukariotic promoters, such as, for instance, the immediate early region promoter of the cytomegalovirus (CMV) as demonstrated by Ensoli et al. (Ref. 41), and reported in Table 3.

TABLE 3

Expression, subcellular localization, release and activity of Tat in COS-1 cells transfected with pCV-Tat and CMV-Tat[a].

| Vectors | Tat expression | | | Tat[b] content | | | Tat activity | |
|---|---|---|---|---|---|---|---|---|
| Positive Cells | Nucleus[c] (%) | Cytoplasm | | Total | Intracell. (%) | Extracell. (%) | Intracell.[d] (fold) | Extracell.[e] (cpm) |
| PCV-Tat | 5-10 | ++ | ++ | 25 | 63.5 | 36.5 | 50 | 2.478 |
| CMV-Tat | 3-5 | ++ | + | 14.6 | 92.2 | 7.8 | 72 | 2.254 |
| Control | 0 | – | – | 0 | 0 | 0 | 1 | 1.400 |

[a]COS-1 cells ($5 \times 10^6$) were transfected by electroporation with 30 µg of pCV-Tat, CMV-Tat or a control DNA. 48 hours after transfection, Tat expression was evaluated by immunoistochemistry with anti-Tat monoclonal antibodies (given values are the mean of the percentage values of positive cells) and by localization of nuclear and cytoplasmic Tat. The presence of intra- and extra-cellular Tat was analyzed by radioimmunoprecipitation on the cellular extracts (500 µl) and in the culture media (4 ml) and subsequent densitometric reading (Gelscan XL; Pharmacia) of the precipitated Tat bands. The activity of intracellular Tat was measured on cellular extracts of COS-1 cells co-transfected with Tat expressing vectors, or the control vector, and the LTR-CAT HIV-1 plasmid; the extracellular Tat activity on the AIDS-KS cells proliferation (determined by $^3$H-timidine incorporation assay) was measured in the culture medium (diluted 1:2 and 1:4) of the cells transfected with plasmids expressing Tat or the control plasmid. The results are the average of five independent experiments.
[b]Densitometric analysis of the immunoprecipitated Tat protein band. Values are expressed in an arbitrary scale, the total detected minimum value (intra- and extra cellular Tat) being 10.
[c]–, negative; +, 50% of Tat-positive cells; ++, 50-100% of Tat-positive cells.
[d]CAT activity after 20 minutes incubation with respect to the control vector, the activation value of which being considered 1.
[e]AIDS-KS cell growth was measured by a $^3$[H]-thymidine incorporation assay (standard deviation, SD: 12%). The supernatants of the cells transfected with the control DNA had a $^3$[H]-thymidine incorporation of 1,400 cpm (SD: 11.5%). The culture medium derived from activated T lymphocytes (positive control) had a $^3$[H]-thymidine incorporation of 2,400 cpm (SD: 10%).

Lys41-RGDΔ Mutant Nucleotide Sequence SEQ. ID. NO. 9

5'ATGGAGCCAGTAGATCCTAGACTAGAGC-
CCTGGAAGCATCCAGGAAGTCA GCCTAAAACT-
GCTTGTACCAATTGCTATTGTAAAAAGT-
GTTGCTTTCATTGCCA AGTTTGTTTCATAACAA
CAGCCTTAGGCATCTCCTATGGCAGGAAGAAGCGG
AGACAGCGACGAAGACCTCCTCAAG-
GCAGTCAGACTCATCAAGTCTCTAT CAAAGCAGC-
CCACCTCCCAATCCCCGACAGGCCCGAAGGAATAG
3'

Amino Acidic Acid Sequence SEQ. ID. NO. 10

NH2-MEPVDPRLEPWKHPGSQPKTACTNCYCK-
KCCFHCQVCFITTALG ISYGRKKRRQRRRPPQG-
SQTHQVSLSKQPTSQSPTGPKE-COOH

Example 3

Construction and Characterization of the DNA Immunogens

The DNA molecules for the inoculation of animals are inserted in the 6.4 kb pCV0 plasmid vector (Ref. 5). This plasmid comprises two SV40 replication origins, the major late promoter of the adenovirus (AdMLP) and the splicing sequences of the adenovirus and of the mice immunoglobulin genes, the cDNA of mice dihydrofolate-reductase gene (dhfr) and the SV40 polyadenilation signal. The site for the PstI restriction enzyme is located at the 3' of the AdMLP, and represents the site in which the exogenous gene of interest is cloned. The tat gene cDNA (261 base pairs) (SEQ ID NO:1, example 2) of HIV-1 was derived from the HIV-1 BH10 clone (Ref 126) and coded for a 86 amino acid-long protein. The Table 3 shows that in the pCV-Tat transfected cells, compared with the CMV-Tat transfected cells, the percentage of Tat-positive cells and the total Tat content are higher, the amount of released Tat is much higher and is related to the total and cytoplasmatic content of Tat, and the biological activity of the extracellular Tat on AIDS-KS cell growth is therefore higher. Such results show that the pCV-Tat vector codes for a biologically active protein, induces high expression levels of the tat gene and can release from the cells much higher Tat amounts than the CMV-Tat vector.

The pCV0 vector is utilized also for the expression of HIV-1 nef, rev and gag genes and of the genes coding for IL-12 and IL-15 cytokines. The cDNAs of nef (618 base pairs, NL43 strain) (Ref. 112), rev (348 base pairs, strain NL43) (Ref. 95) and the gag genes (1500 base pairs, strain NL43) (Ref. 95), or the cDNAs of IL-12 (Ref. 165) or IL-15 genes (Ref 56) are amplified by polymerase chain reaction technique (PCR) by using specific primers complementary to the first 15 nucleotides of 5' region (primer forward) (SEQ ID NO:18, 20, 22, 24, or 26) or to the last 15 nucleotides of 3' region of the gene (primer reverse) (SEQ ID NO:19, 21, 23, 25, or 27). Moreover, each primer, both forward and reverse, comprises the sequence for the restriction PstI enzyme to consent the cloning of the amplified product into the pCV0 vector. After cloning, the sequence of the inserted genes is controlled by DNA sequencing. The pCV0 vector is used also for the Tat co-expression with other viral genes of HIV-1 (rev, nef or gag) or with the IL-12 or IL-15 cytokine-coding genes. To this end the cDNA of the HIV-1 tat gene of 261 base pairs (SEQ ID NO:1, example 2) is amplified by PCR with a primer forward including the sequence for the PstI restriction enzyme (SEQ ID NO:28) and a primer reverse complementary to the last 15 nucleotides of the tat gene (SEQ ID NO:29).

The viral genes (rev, nef or gag) or the genes coding for the IL-12 or IL-15 cytokines are amplified by a primer forward which includes also a sequence of 15 bases complementary to the tat 3' region, permitting the gene being in frame with the tat gene (SEQ ID NO:30, 31, 32, 33, or 34), and a primer reverse including the sequence for the PstI restriction enzyme (SEQ ID NO:19, 21, 23, 25, or 27). Afterwards, a third PCR reaction is performed in which the DNA template is represented by the amplified products of the tat gene and of the gene of interest. The primer forward is represented by the primer utilized to amplify tat (SEQ ID NO:28) and the primer reverse by the one utilized in amplifying the gene of interest (SEQ ID NO:19, 21, 23, 25, or 27). The amplified tat/gene of interest is purified with agarose gel, digested with PstI and cloned in pCV0. After cloning, the sequence of the inserted genes is controlled by DNA sequencing, while the protein expression is determined by means of transfection as described above (Ref. 41).

The sequences of the above mentioned primers are:

Primer forward Rev: 5'ATGGCAGGAAGAAGC3' SEQ. ID. NO. 18
Primer reverse Rev: 5'CTATTCTTTAGTTCC3' SEQ. ID. NO. 19
Primer forward Nef: 5'ATGGGTGGCAAGTGG3' SEQ. ID. NO. 20
Primer reverse Nef: 5'TCAGCAGTCCTTGTA3' SEQ. ID. NO. 21
Primer forward Gag: 5'ATGGGTGCGAGAGCG3' SEQ. ID. NO. 22
Primer reverse Gag: 5'TTATTGTGACGAGGG3' SEQ. ID. NO. 23
Primer forward IL-12: 5'ATGTGGCCCCCTGGG3' SEQ. ID. NO. 24
Primer reverse IL-12: 5'TTAGGAAGCATTCAG3' SEQ. ID. NO. 25
Primer forward IL-15: 5'ATGAGAATTTCGAAA3' SEQ. ID. NO. 26
Primer reverse IL-15: 5'TCAAGAAGTGTTGAT3' SEQ. ID. NO. 27
Primer forward Tat: 5'ATGGAGCCAGTAGAT3' SEQ. ID. NO. 28
Primer reverse Tat: 5'CTATTCCTTCGGGCC3' SEQ. ID. NO. 29
Primer forward Tat/Rev: 5'GGCCCGAAGGAAATGGCA GGAAGAAGC3' SEQ. ID. NO. 30
Primer forward Tat/Nef: 5'GGCCCGAAGGAAATGGGT GGCAAGTGG3' SEQ. ID. NO. 31
Primer forward Tat/Gag: 5'GGCCCGAAG-GAAATGGGTGCG AGAGCG3' SEQ. ID. NO. 32
Primer forward Tat/IL-12: 5'GCCCGAAGGAAAT-GTGGC CCCTGGG3' SEQ. ID. NO. 33
Primer forward Tat/IL-15: 5'GGCCCGAAGGAAAT-GAGAAT TCGAAA3' SEQ. ID. NO. 34

Example 4

Inoculation in Healthy *Macaca fascicularis* of an Anti-Tat Protein Vaccine: Evaluation of Safety, Tolerability, Specific Immune Response and Protective Efficacy Against Virus Challenge The tolerability, safety and the ability to elicit a specific immune response (humoral and cellular) and protection against virus challenge of the recombinant Tat protein vaccine, produced by the described method and purified through heparin-affinity columns, was assessed in the experimental model of cynomolgus monkey is (*Macaca fascicularis*). In order to induce a broad immune response we used aluminum phosphate (Alum) that has been tested in numerous models and it is the sole approved for human use. Among particulate adjuvants we used RIBI (belonging to the group of emulsifiers or composed by monophosphorylic lipid A, dimycolic trehasole and skeleton of the bacterial wall of Calmette-Guerin *bacillus*) (Ref. 7, 109).

In the first pilot experiment we evaluated the tolerability, the safety and the ability to elicit a specific immune response (humoral and cellular). Thus, 3 monkeys were inoculated according to the following schedule: monkey 1 (M1) was inoculated with the recombinant Tat protein (100 μg), resuspended in 250 μl of autologous serum and 250 μl of RIBI, by the subcute route in one site; monkey 2 (M2) was inoculated with the recombinant Tat protein (10 μg), resuspended in 250 μl of autologous serum and 250 μl of RIBI, by the subcute route in one site; and monkey 3 (M3) was the control monkey not inoculated. Ten ml of blood were withdrawn from all monkeys at days −42 and −35 preceding the first vaccine inoculation in order to determine the basal parameters. Serum and plasma samples were frozen at −20° C. or −80° C. and used later to resuspend the protein inoculum. Monkeys 1 and 2 were inoculated at time 0 and after 2, 5, 10, 15, 22, 27, 32 and 37 weeks. The immunization schedule was interrupted at week 37 for monkey M1 and at week 41 for monkey M2. Animals were sacrificed to study the immunological parameters in several organs and tissues (spleen and lymph nodes), such as the evaluation of the presence of a proliferative response to Tat, and of CAF and CTL activities against Tat. CAF activity is the antiviral activity mediated by CD8+ lymphocytes, neither MHC-restricted nor cytolytic. In the same days of the inoculation of the immunogen, 10 ml of blood were withdrawn from each animal to perform laboratory tests (chemo-physic analyses, electrolytes, leukocytes, platelet counts and haemoglobin quantitation), the evaluation of the immunological parameters, such as the presence of specific immunoglobulins (IgM, IgG, IgA), the levels of Th1 type-(IL-2, IFNγ) and Th2 type-cytokines (IL-4, IL-10), the production of chemokines (RANTES, MIP-1α and MIP-1β), the lymphocytic phenotype (CD4, CD8, CD3, CD14, CD20, CD25, CD56, HLA-DR, CD45RA), the proliferative response to Tat, the presence of specific cytotoxic activity (CTL), the presence of antiviral activity (CAF), and the presence of total antiviral activity (TAA) mediated by PBMC and by autologous serum. Moreover, to evaluate the in vivo presence of a cell-mediated immune response, all vaccinated and control monkeys were subjected to a skin-test to Tat.

The results of this experiment are as follows. No alterations of the chemo-physic, haematologic and behavioristic parameters were observed. In vaccinated and control monkeys, signs of inflammation and neo-vascularization were not detected at the sites of inoculation. These results indicate that the Tat protein was well tolerated by the animals and that was non-toxic at the administered doses and at the given inoculation route. In monkeys M1 and M2 the presence of antibodies of the IgG type specific to Tat were detected at week 5 after the first inoculation. At week 37, anti-Tat IgG were detectable up to 1:6400 plasma dilution in both monkeys, and, at week 41, up to 1:12.800 plasma dilution in monkey M2. The results are shown in FIGS. 2 and 3. In the control monkey M3, anti-Tat antibodies with low titers were detected, likely elicited by the repeated inoculations of low amount of Tat that was injected in this monkey to control the specificity of the skin test reactions. In monkeys M1 and M2, anti-Tat antibodies were mainly directed against the amino-terminal region (aa 1-20) of Tat, with a titer of 1:3200 (FIG. 4). In monkey M2, vaccinated with 10 μg of Tat, antibodies directed against aa 36-50 and 46-60 of Tat were also detected, with titers of 1:50 and 1:100, respectively (FIG. 4). The ability of monkeys' serum to neutralize Tat was determined by means of in vitro assays that measured the inhibition of the rescue of HIV-1 replication in HLM-1 cells after the addition of exogenous Tat protein, as previously described (Ref. 41). These assays demonstrated that plasma from monkeys M1 and M2, at week 27 after the first inoculation, blocked virus to replication induced by exogenous Tat, as determined by quantification of p24 antigen in the culture supernatants. Conversely, preimmune plasma from the same monkeys did not block Tat activity (Table 4).

TABLE 4

Neutralizing activity of monkeys' plasma on the rescue of virus replication induced by extracellular Tat[a]

| Samples | Inhibition (%) |
| --- | --- |
| Tat (30 ng/ml) + Preimmune M1 | 0 |
| Tat (30 ng/ml) + Preimmune M2 | 0 |
| Tat (39/ng/ml) + Immune Ml | 79.12 |
| Tat (30 ng/ml) + Immune M2 | 100 |

[a]The neutralizing activity of plasma was determined in HLM-1 cells (HeLa-CD4+ cells containing an integrated copy of an HIV-1 provirus defective in the tat gene). HLM-1 cells were seeded at $6 \times 10^5$ cells/well in 24-well plates and incubated at 37° C. for 16 hours. Cells were washed twice with PBS, containing 0.1% of bovine serum albumin (BSA), and cultured for 48 hours with fresh medium (0.3 ml) in the presence of recombinant Tat protein and an equal volume of theanimal plasma, withdrawn at time 0 (preimmune plasma) or at week 27 (immune plasma). Negative controls were represented by cells treated only with the preimmune plasma pooled together, with the immune plasma pooled together or with PBS containing 0.1% BSA (PBS + 0.1% BSA), without Tat. In all control samples no effects were observed on the rescue of virus replication. Each plasma was tested in duplicate. The presence of virus released by the cells was assayed by quantitation of p24 Gag antigen,using a commercial p24 antigen capture ELISA kit (NEN-Dupont). The results are expressed as the percentage of inhibition of virus rescue [measured for each plasma as the average value of p24 (pg/ml) in two wells] by the immune plasma as compared to the preimmune plasma (0% inhibition). Monkeys M1 and M2 were vaccinated with the recombinant Tat protein (100 μg and 10 μg, respectively) resuspended in 250 μl of autologous serum and 250 μl of RIBI, and injected by the subcute route in onesite.

The results indicate the presence of a proliferative response to Tat at week 22 (Table 5) in monkeys vaccinated with the recombinant Tat protein, being higher in to monkey M2 that received 10 μg of recombinant Tat protein at each boost.

TABLE 5

Proliferative response to Tat[a]

| Monkey | Stimulus | Weeks from the primary immunization | | | | |
| --- | --- | --- | --- | --- | --- | --- |
| | | 15 | 22 | 27 | 32 | 37 |
| M1 | PHA | 15.3 | 13.9 | 19.9 | 40.6 | 3.2 |
| | TT | 1.2 | 4.7 | 2.1 | 3.8 | 2 |
| | Tat | 0.8 | 2.4 | 1.1 | 1.3 | 0.6 |
| M2 | PHA | 8.1 | 11.6 | 17.1 | 16.8 | 1.7 |
| | TT | 2 | 3.8 | 1.7 | 1 | 0.6 |
| | Tat | 0.9 | 3 | 1.4 | 1.2 | 0.6 |
| M3 | PHA | 5.1 | 19.9 | 18.2 | 6.6 | 8.1 |
| | TT | 7.2 | 6.2 | 5.5 | 2.8 | 5.6 |
| | Tat | 2.1 | 1.4 | 1.3 | 0.7 | 0.9 |

[a]PBMCs isolated by Ficoll density gradient were plated at a concentration of $2 \times 10^5$ cells/well in triplicates in a flat bottomed 96-well plate, cultured in RPMI-1640 supplemented with 10% fetal calf serum (FCS) and stimulated with Tat (1 or 5 μg/ml), PHA (4 μg/ml) or Tetanus Toxoid (TT) to which monkeys were vaccinated. Unstimulated controls were incubated in RPMI, 10% FCS medium. The increase of cellular proliferation was measured at day 5 by $^3$[H]-thymidine incorporation as previously described (Ref. 39, 22). Results are expressed as stimulation index and were calculated as follows: average of the test sample (cpm)/average of control (cpm). Values greater than 2.5 were considered positive. Monkeys M1 and M2 were immunized subcute with 100 μg or 10 μg of recombinant Tat resuspended in 250 μl of autologous serum and 250 μl of RIBI. M3 represents a control monkey.

As shown in Table 6 no cytotoxic activity to Tat was detected in monkeys M1 and M2 immunized with recombinant Tat.

TABLE 6

Analysis of cytotoxic activity to Tat (CTL)[a]

| Monkey | Week | Target:Effector ratio | | | | | | CTL activity |
| --- | --- | --- | --- | --- | --- | --- | --- | --- |
| | | 1:50 | 1:25 | 1:12.5 | 1:6.25 | 1:3.125 | Media | |
| M1 | 41 | ND | ND | ND | ND | ND | ND | ND |
| M2 | 41* | 0 | 0 | 0 | 0 | 0 | 0 | — |
| M3 | 41 | 0 | 0 | 0 | 0 | 0 | 0 | — |

[a]PBMCs isolated by Ficoll density centrifugation were resuspended at a concentration of $1 \times 10^7$ cells/ml in RPMI 1640 supplemented with 10% heat inactivated FCS and seeded in a 24-well plate (500 μl per well) for 12 hours at 37° C. in the presence of 1 μg of Tat. One day later, the cells incubated without Tat were centrifuged at 1500 rpm and resuspended in 50 μl of RPMI 1640 supplemented with 10% FCS, incubated for 3 hours at 37° C. with 1 μg of Tat, washed, resuspended in 500 μl of fresh medium and added to the well containing the PBMCs previously stimulated. On day 2 the cells were diluted with 1 ml of medium containing IL-2 (2 IU/ml) and cultured for 14 days. Autologous B lymphocytes isolated from each monkey before the vaccine protocol were used as target cells (BLCL). To this aim, PBMCs isolated by Ficoll density centrifugation at day 35 were seeded at a concentration of $3 \times 10^5$ cells/well in a 96-well plate and cultured for 2 or 3 weeks in the presence of 50% of a medium collected from a cell line that produces Papiovirus as previously described (Ref. 28). Ten B cell lines obtained for each animal were expanded and frozen. To test the toxicity, the Delfia Cytotoxic Test (Wallac, Turku, Finland) based on the time resolved fluorescence was used (Ref. 12, 13, 14). To this aim, BLCL were cultured at a concentration of $1 \times 10^6$ cells/200 μl of RPMI 1640 supplemented with 10% FCS containing 4 μg of Tat for 12 hours at 37° C. As the control, another aliquot of autologous BLCL was incubated with the same medium without Tat. BLCL were washed and resuspended in 1 ml of RPMI 1640 supplemented with 10% FCS containing 5 μl of fluorescence enhancing ligand and incubated for 15 min at 37° C. according to the manufacturer's instruction. After 5 washings, BLCL were resuspended at a concentration of $5 \times 10^4$ cells/ml and promptly centrifuged in order to harvest the supernatant that was used to measure the background level. PBMCs (Effectors) were seeded in duplicate at a concentration of $2.5 \times 10^4$ cells/100 μl in medium containing IL-2 and properly diluted in a 96-well plate. $5 \times 10^3$ of target cells/100 μl (cultured with or without Tat) were added to each well. Target:Effector ratios were 1:50, 1:25, 1:12.5, 1:6.25, 1:3.125. PBMCs and target cells (Tat-pulsed or unpulsed) were incubated for 2 hours at 37° C. with i) 20 μl of 5% Triton to measure the maximum release, ii) 100 μl of growth medium to detect the spontaneous release, iii) 200 μl of supernatant from target cells to detect the background level. At the end of the incubation period the plates were centrifuged, 20 μl of each supernatant were transferred into a new plate and incubated in the presence of 200 μl of an Europium solution included in the kit. The fluorescence was measured after 20 min incubation with a time resolved fluorescence reader (Victor, Wallac, Turku, Finland). Specific CTL activity was measured as following: % specific release = [(average of sample detection – background) – (spontaneous release – background)]/[(Maximum release – background) – (spontaneous release – background)] × 100. The test was considered positive when the Tat specific-release was higher than 4% at most of the Effector:Target ratios tested. 4% is an arbitrary value established on the basis of previous control experiments. ND, not determined. Monkey M2 was immunized subcute with 10 μg of recombinat Tat resuspended in 250 μl of autologous serum and 250 μl of RIBI. M3 represents a control monkey.

ND: not done.

*PBMCs were isolated from peripheral lynph nodes when M2 had been sacrificed. Moreover, the results demonstrate, at weeks 22, 27 and 37, the presence of soluble antiviral activity mediated by CD8+ T lymphocytes (CAF), measured as the ability of cell supernatants from monkeys CD8+ T lymphocytes to inhibit acute infection of the chimeric virus SHIV 89.6P in CEM x 174 cells, or to control reactivation of HIV-1 chronic infection in OM-10-1 cells (Table 7). CAF activity was generally observed in vaccinated monkeys as compared to control animals.

TABLE 7

Analysis of the presence of soluble antiviral activity mediated by CD8+ T lymphocytes (CAF)[a]

| Monkey ID | Week after the primary immunization | % inhibition of viral replication | |
| --- | --- | --- | --- |
| | | Acute infection | Chronic infection |
| M1 | 22 | 89.5 | ND |
| | 27 | 62 | 61.7 |
| | 37 | ND | ND |
| M2 | 22 | 44 | ND |
| | 27 | 54 | 27 |
| | 37 | 48 | 53 |

TABLE 7-continued

Analysis of the presence of soluble antiviral activity mediated by CD8+ T lymphocytes (CAF)[a]

| | | | |
|---|---|---|---|
| M3 | 22 | 24 | ND |
| | 27 | 37 | 22 |
| | 37 | 75 | 23 |

[a]PBMC from monkeys vaccinated with 100 μg (M1) and 10 μg (M2) of recombinant Tat protein and from a control monkey (M3), that was not vaccinated, but had repeated skin tests with Tat were isolated by Ficoll density gradient. CD8+ T lymphocytes enriched cultures were isolated from PBMC by anti-CD8 magnetic beads (Dynabeads, Dynal, Norway) according to manufacturer's instructions. The purity of the cultures was controlled by FACS analysis using a series of antibodies directed againstspecific cellular markers (CD3, CD4, CD8). CD8+ enriched cultures were seeded (in duplicate) at $5 \times 10^5$ cells/500 μl per well in 48-well plates, previously coated with an anti-CD3 monoclonal antibody (2.5 μg/ml, Bio-Source International, Camarillo, CA) for 12 hours at 4° C., and grown in RPMI 1640, containing 10% fetal bovine serum and IL-2 (20 U/ml). 250 μl of medium were collected every three days, for two weeks, and substituted with an equal volume of fresh medium. Cellsupernatants were centrifuged, filtered (0.45 μm) and stored at –80° C. Cell supernatants derived from all time points, with the exception of the first one, were pooled and the presence of antiviral activity was tested as their ability to inhibit viral replication in two systems, represented by acute and chronic infection, respectively. For the acute infection system, the CEM x 174 cell line was used, which derives from the human B cell line 721.174 fused with the human T cell line CEM(Ref. 143). Cells ($2 \times 10^5$) were incubated in polypropilene tubes with or without 200 μl of CD8+ supernatants, prepared as described above, for 2 hours at 37° C. Cells were washed 3 times with fresh medium, seeded at $2 \times 10^4$ cells per well, in 96-well plates, and incubated in 200 μl with (treated cells) or without (untreated cells) of different volumes (50 μl, 5 μl and 0.5 μl) of culture supernatants derived from CD8+ T lymphocytes of monkeysinjected with the vaccine or the control monkey. After infection, aliquots of culture supernatants were collected every three days and substituted with an equal volume of complete medium previously added with the CD8+ culture supernatant from vaccinated and control monkeys. The results shown in the Table correspond to day 7 after infection and are expressed as percentage (%) of inhibition of viral replication of cells treated with CD8+ culture supernatants derived from vaccinated monkeys ascompared to untreated cells. Viral replication was determined by measuring the RT values, as described (Ref. 54), or the p27 Gag values by ELISA, in the cell supernatants collected at each time point. For the chronic infection system OM-10-1 cell line was used (Ref, 20, 21), which represents a human T lymphocytic line chronically infected by HIV-1. Cells were seeded (in duplicate) at $5 \times 10^4$ cells/200 μl per well, in 96-well plates, in the presence of anti-TNFβ antibodies (40 μg/ml), with or without different volumes (50 μl, 5 μl, 0.5 μl) of cell supernatant from CD8+ T lymphocytes derived from vaccinated or control monkeys. Cells were activated to proliferate by PMA ($10^{-7}$ M). After 24 hours, aliquots of culture medium were collected to determine viral replication by measuring RT or p24 Gag levels by ELISA. The results are represented as % of inhibition of reactivation of infection in treated cells as compared to untreated cells. The results of acuteacute and chronic infection shown in the Table refer to cells treated with 5 μl of supernatant derived from CD8+ cell cultures.
ND: not done.

Analysis of the delayed hypersensitivity (DTH) by means of a skin test showed that both the vaccinated (M1 and M2) and control (M3) monkeys were negative (Table 8).

TABLE 8

Skin-test to Tat[a]

| Weeks after the primary immunization | Monkeys | | |
|---|---|---|---|
| | M1 | M2 | M3 |
| 10 | — | — | — |
| 15 | — | — | — |
| 22 | — | — | — |
| 27 | — | — | — |
| 32 | — | — | — |
| 37 | — | — | — |

[a]Tat (1 and 5 μg) in 150 μl of PBS-0.1% BSA or the buffer alone were inoculated by the intradermal route in a dorsal area previously shaved of the vaccinated and control (control of specificity of the response) monkeys, at weeks 10, 15, 22, 27, 32 and 37 following the first immunization. Monkeys M1 and M2 were vaccinated with recombinant Tat protein (100 ug and 10 μg, respectively) in 250 μl of autologous serum and 250 μl of RIBI, injected by the subcute route in one site. MonkeyM3 is a control monkey that has not been vaccinated. The appearance of a nodular erythema after 48-72 hours was suggestive of a delayed hypersensitivity reaction (DTH): ++, $\phi \geq 5$ mm; +, $\phi \geq 1$-4 mm, +/–, erythema without hardening; –, $\phi < 1$ m.

The results of this pilot experiment indicate that Tat recombinant protein, produced and purified according to a protocol described by us, was not toxic at the doses of 100 and 10 μg administered by the subcute route. In addition, Tat protein elicited a specific and broad immune response with antiviral activities, both humoral and cell-mediated. A stronger and specific anti-Tat immune response was observed in monkey M2, vaccinated with 10 μg of recombinant protein. Moreover, the RIBI adjuvant did not show any apparent sign of toxicity in the vaccinated monkeys. Based on these results, a second pilot experiment was designed in order to determine the effects of immunization with 10 μg of Tat combined with RIBI or Alum adjuvants. Monkeys were injected by the subcute route in one site according to the following schedule. Monkey M1-3: 10 μg of recombinant Tat protein in 250 of autologous serum and 250 μl of RIBI. Monkeys M4-6: 10 μg of recombinant Tat protein in 250 μl of autologous serum and 250 μl of Alum. Monkey M7: RIBI 250 μl and 250 μl of autologous serum (control monkey). Monkey M8: Alum 250 μl and 250 μl of autologous serum (control monkey). Ten ml of blood were withdrawn from each monkey at day –9 preceding the first immunization in order to carry out the exams described in the previous pilot experiment and to determine the basal parameters of each animal. Monkeys were inoculated at time 0 and after 2, 6, 11, 15, 21, 28 and 32 weeks. At week 36 monkeys M1-6 received the last boost with recombinant Tat protein (16 μg) in 200 μl of ISCOM (immune stimulating complex) and 300 μl of PBS. ISCOM is an adjuvant consisting of quil A saponin, cholesterol and phospholipids which increases humoral and cell-mediated immune response (Ref. 109, 90). Monkeys M7 and M8 were injected at the same time points only with adjuvants. At each vaccination point and at weeks 40, 44 and 50, 10 ml of blood were withdrawn from the animals to analyze the clinical and immunological parameters described in the previous pilot experiment. Moreover, urine samples and vaginal swabs were collected to analyze the presence of Tat specific secretory IgA. In order to evaluate the protective effect of Tat immunization against the infection, vaccinated and control monkeys were challenged with the chimeric "simian/human immunodeficiency virus" (SHIV), strain 89.6P, containing the HIV-1 tat gene, previously grown and titered in *Macaca fascicularis* (Ref. 128, 129, 69). After challenge, animals were monitored (every two weeks for the first month, every four weeks for the next three months and every 8 weeks up to 6-12 months) for virological parameters, such as plasma p27 antigenemia and plasma and cellular viral load. To confirm that infection had occurred, anti-SIV antibodies were also searched by means of a commercial kit used for the detection of anti-HIV-2 antibodies which recognizes also anti-SIV antibodies (Elavia Ac-Ab-Ak II kit, Diagnostic Pasteur, Paris, France).

At present, the results of the second pilot experiments are as follows. No alterations of the chemo-physical, haematological and behavioristic parameters were observed. Monkeys did not show any inflammatory or neovascularization sign at the site of inoculation. A specific antibody response (IgM, IgG) was observed. At week 15 anti-Tat antibody (IgG) titers reached high levels, ranging from 1:6400 to 1:25600 (FIGS. 5-7). The antibodies essentially reacted with the amino-terminal region (aa 1-20) of Tat, with titers ranging from 1:1600 to 1:3200 (FIG. 8) as shown at week 22. Moreover, antibodies directed against aa 46-60 of Tat, with titers ranging from 1:100 to 1:200, were also detected (FIG. 8). The ability of the monkeys' plasma to neutralize Tat activity was tested by assaying the inhibition of viral rescue in HLM-1 cells incubated with serial amounts of exogenous Tat, as previously described in the first pilot experiment. The results of these experiments have shown that immune plasma (diluted 1:2) from monkeys M1-6 at week 15 blocked viral replication induced by 30 ng/ml of exogenous Tat, as determined by the measurement of p24 antigen released into the culture medium. Conversely, the preimmune plasma of monkeys M1-6 or plasma from control monkeys (M7, M8) did not block Tat activity (Table 9). Moreover, immune plasma (diluted 1:2) of monkeys M1-6, withdrawn at week 21, blocked virus replication induced by 60 ng/ml, 120 ng/ml, 240 ng/ml and 500 ng/ml of exogenous Tat. In particular, these plasma determined a 10-fold reduction of virus replication induced by very high doses of extracellular Tat (240 ng/ml and 500 ng/ml) (Table 9).

TABLE 9

Neutralizing activity of immune plasma on the rescue of virus replication induced by extracellular Tat[a]

| Samples | Inhibition (%) |
|---|---|
| Tat (30 ng/ml) + Preimmune M1 | 0 |
| Tat (30 nglml) + Preimmune M2 | 0 |
| Tat (30 ng/ml) + Preimmune M3 | 0 |
| Tat (30 ng/ml) + Preimmune M4 | 0 |
| Tat (30 ng/ml) + Preimmune M5 | 0 |
| Tat (30 ng/ml) + Preimmune M6 | 0 |
| Tat (30 ng/ml) + Immune M1 (week 15) | 89.8 |
| Tat (30 ng/ml) + Immune M2 (week 15) | 78.7 |
| Tat (30 ng/ml) + Immune M3 (week 15) | 100 |
| Tat (30 ng/ml) + Immune M4 (week 15) | 100 |
| Tat (30 ng/ml) + Immune M5 (week 15) | 70.8 |
| Tat (30 ng/ml) + Immune M6 (week 15) | 94.2 |
| Tat (60 ng/ml) + Preimmune M1 | 0 |
| Tat (60 ng/ml) + Preimmune M2 | 0 |
| Tat (60 ng/ml) + Preimmune M3 | 0 |
| Tat (60 ng/ml) + Preimmune M4 | 0 |
| Tat (60 ng/ml) + Preimmune M5 | 0 |
| Tat (60 ng/ml) + Preimmune M6 | 0 |
| Tat (60 ng/ml) + Immune M1 (week 21) | 96.3 |
| Tat (60 ng/ml) + Immune M2 (week 21) | 100 |
| Tat (60 ng/ml) + Immune M3 (week 21) | 100 |
| Tat (60 ng/ml) + Immune M4 (week 21) | 98.7 |
| Tat (60 ng/ml) + Immune M5 (week 21) | 99 |
| Tat (60 ng/ml) + Immune M6 (week 21) | 98.8 |
| Tat (120 ng/ml) + Pool preimmune M1-6 | 0 |
| Tat (120 ng/ml) + Immune M1 (week 21) | 59.2 |
| Tat (120 ng/ml) + Immune M2 (week 21) | 90.4 |
| Tat (120 ng/ml) + Immune M3 (week 21) | 96.8 |
| Tat (120 ng/ml) + Immune M4 (week 21) | 98.3 |
| Tat (120 ng/ml) + Immune M5 (week 21) | 100 |
| Tat (120 ng/ml) + Immune M6 (week 21) | 97.8 |
| Tat (240 ng/ml) + Pool preimmune M1-6 | 0 |
| Tat (240 ng/ml) + Immune M1 (week 21) | 26.1 |
| Tat (240 ng/ml) + Immune M2 (week 21) | 49.4 |
| Tat (240 ng/ml) + Immune M3 (week 21) | 70.3 |
| Tat (240 ng/ml) + Immune M4 (week 21) | 91.2 |
| Tat (240 ng/ml) + Immune M5 (week 21) | 94.5 |
| Tat (240 ng/ml) + Immune M6 (week 21) | 86 |
| Tat (500 ng/ml) + Pool preimmune M1-6 | 0 |
| Tat (500 ng/ml) + Immune M1 (week 21) | 32.7 |
| Tat (500 ng/m/) + Immune M2 (week 21) | 38.9 |
| Tat (500 ng/ml) + Immune M3 (week 21) | 57.5 |
| Tat (500 ng/ml) + Immune M4 (week 21) | 89.4 |
| Tat (500 ng/ml) + Immune M5 (week 21) | 72 |
| Tat (500 ng/ml) + Immune M6 (week 21) | 71.8 |

[a]The ability of anti-Tat plasma to neutralize Tat activity was determined in HLM-1 cells, as described in legend to Table 4. Recombinant Tat protein (30 ng/ml, 60 ng/ml, 120 ng/ml, 240 ng/ml and 500 ng/ml) was added alone or together with an equal volume of monkey preimmune plasma or at week 15 or 21 (immune plasma). Monkeys M1-3 were vaccinated with 10 μg of Tat in 250 μl of autologous serum and 250 μl of RIBI; monkeys M4-6 were vaccinated with 10 μg of Tat in 250 μl of autologous serum and 250 μl of Alum; two control monkeys were injected with RIBI (250 μl and 250 μl of autologous serum) (M7) or with Alum (250 μl and 250 μl of autologous serum) (M8). The results are represented as described in legend to Table 4.

The ability of monkey plasma to neutralize the activity of extracellular Tat released by the cells during acute infection was tested in CEM x 174 cells infected with the chimeric virus SHIV 89.6P. At day 7 after infection virus replication was observed in 50% of control cells infected with SHIV and cultivated with the preimmune plasma of monkeys M1-6. Conversely, virus replication was not detected in infected cells that were grown in the presence of the immune plasma from monkeys M1-6 withdrawn at week 44 (Table 10).

TABLE 10

Neutralizing activity of immune plasma on transmission of virus infection[a]

| Sample | p27 (pg/ml) |
|---|---|
| SHIV + Preimmune M1 | Neg |
| SHIV + Preimmune M2 | Neg |
| SHIV + Preimmune M3 | 1.080 |
| SHIV + Preimmune M4 | 0.602 |
| SHIV + Preimmune M5 | 1.169 |
| SHIV + Preimmune M6 | Neg |
| SHIV + Immune M1 | Neg |
| SHIV + Immune M2 | Neg |
| SHIV + Immune M3 | Neg |
| SHIV + Immune M4 | Neg |
| SHIV + Immune M5 | Neg |
| SHIV + Immune M6 | Neg |

[a]CEM x 174 cells (3 x $10^4$ cells/150 μl) in 96-well plates were infected with the chimeric SHIV 89.6P virus (5 x $10^{-5}$ $TCID_{50}$/cell) for 2 hours at 37°C. in RPMI 1640 containing 10% FCS. Cells were washed twice with RPMI 1640 and resuspended in 150 μl of complete medium added with 5% of the monkey preimmune plasma or immune plasma (week 44) from animals vaccinated with recombinant Tat (10 μg) and RIBI (M1-3) or Alum (M4-6). Animal plasma were previously heated at 56° for 30 min. and analyzed by ELISA to control anti-Tat antibody titers. Each serum was tested in duplicate. At days 3, 5 and 7 after infection 120 μl of culture medium were collected and substituted with an equal volume of fresh medium containing 5% of preimmune or immune plasma from monkeys M1-6. The ability of the plasma to neutralize extracellular Tat, released during acute infection, and to control the transmission of infection in vitro was determined by detecting the viral Gag p27 in the culture medium by ELISA (Coulter International, Miami, FL). The results, represented as p27 values (pg/ml), correspond to the mean value of two wells for each serum at day 7 after infection.

Moreover, a proliferative response to Tat was observed since week 11 (Table 11).

TABLE 11

Proliferative response to Tat[a]

| | | Weeks from primary immunization | | | | | | | | |
|---|---|---|---|---|---|---|---|---|---|---|
| Monkey | Stimulus | 0 | 11 | 15 | 21 | 28 | 32 | 36 | 40 | 44 | 50 |
| M1 | PHA | 16.96 | 10.50 | 15.27 | 33.8 | 7.2 | 51.5 | 64.3 | 36.05 | 24 | 65.7 |
| | TT | 11.69 | 1.96 | 3.01 | 1.2 | 1.2 | 1.3 | 0.93 | 1.4 | 10.05 | 7.2 |
| | Tat | 1.12 | 1.55 | 0.52 | 1.7 | 0.8 | 0.8 | 0.6 | 0.7 | 9.27 | 4.7 |
| M2 | PHA | 31.27 | 25.75 | 21.28 | 87.1 | 25.7 | 56 | 38.2 | 40.3 | 29.03 | 26 |
| | TT | 1.12 | 1.8 | 0.57 | 1.7 | 1.15 | 1.6 | 4.95 | 1.2 | 1.51 | 2.9 |
| | Tat | 1.08 | 3.65 | 6.22 | 14.14 | 3.5 | 1.8 | 4.1 | 1.9 | 7.67 | 13.2 |

TABLE 11-continued

Proliferative response to Tat[a]

| Monkey | Stimulus | Weeks from primary immunization | | | | | | | | | |
|---|---|---|---|---|---|---|---|---|---|---|---|
| | | 0 | 11 | 15 | 21 | 28 | 32 | 36 | 40 | 44 | 50 |
| M3 | PHA | 22.42 | 7.89 | 16.88 | 36.3 | 148.5 | 42 | 78.9 | 27 | 53.71 | ND |
| | TT | 11.43 | 0.95 | 1.71 | 1.25 | 1.2 | 1.1 | 1 | 1 | 1.81 | ND |
| | Tat | 1.65 | 2.69 | 18.82 | 23.51 | 12.03 | 0.9 | 1.3 | 0.5 | 23.85 | ND |
| M4 | PHA | 3.88 | 20.77 | 15.22 | 83.7 | 18.6 | 35 | 38.2 | 45.2 | 57.47 | 15.8 |
| | TT | 2.85 | 4.49 | 9.07 | 6.9 | 15.8 | 3.7 | 3.8 | 5 | 19.77 | 6.6 |
| | Tat | 1.29 | 3.01 | 3.24 | 7.9 | 10.1 | 2.6 | 1.5 | 3.9 | 33.61 | 4.7 |
| M5 | PHA | 6.25 | 5.74 | 16.74 | 72.2 | 7.45 | 41 | 56.5 | 32.9 | 33.85 | 12 |
| | TT | 2.31 | 1.07 | 4.84 | 3.9 | 0.9 | 0.83 | 1.4 | 1.24 | 10.22 | 1.95 |
| | Tat | 1.80 | 0.66 | 1.76 | 3.6 | 2.22 | 0.8 | 1.14 | 1.3 | 1.33 | 1.4 |
| M6 | PHA | 11.96 | 17.94 | 2.77 | 29.4 | 7.3 | 25 | 8.3 | 6.85 | 18.01 | 5.2 |
| | TT | 4.14 | 1.71 | 0.13 | 1.7 | 10.34 | 1.3 | 1.8 | 1.1 | 2.49 | 0.9 |
| | Tat | 1.37 | 1.06 | 0.11 | 2.95 | 9.3 | 1.13 | 1.3 | 1 | 5.8 | 0.3 |
| M7 | PHA | 21.65 | 20.30 | 37.93 | 17.6 | 17.9 | 75 | 12.9 | 34.8 | 41.81 | 27.5 |
| | TT | 0.97 | 0.80 | 0.88 | 1 | 0.6 | 1.04 | 0.6 | 0.4 | 1.11 | 1.1 |
| | Tat | 1.78 | 0.68 | 0.73 | 1 | 0.42 | 0.9 | 0.5 | 0.8 | 1.07 | 0.4 |
| M8 | PHA | 26.51 | 67.09 | 16.38 | 14.9 | 17.2 | 28.2 | 18.95 | 20.6 | 28.61 | 13.6 |
| | TT | 1.20 | 10.78 | 0.20 | 1.6 | 0.62 | 0.8 | 1.2 | 0.9 | 1.11 | 2.1 |
| | Tat | 1.12 | 0.00 | 0.21 | 1.03 | 0.57 | 0.6 | 0.5 | 0.9 | 1.04 | 1 |

[a]Peripheral blood lymphocytes were isolated, activated with PHA (4 µg/ml), the tetanus toxoid (TT) (10 µg/ml) and Tat (5 µg/ml) and assayed as described in legend to Table 5. Monkeys M1-3 were inoculated with 10 µg of recombinant Tat protein in 250 µl of autologous serum and 250 µl of RIBI; monkeys M4-6 were inoculated with 10 µg of recombinant Tat in 250 µl of autologous serum and 250 µl of Alum; two control monkeys were inoculated with RIBI (250 µl and 250 µl of autologous serum) (M7) and with Alum (250 µl and 250 µl of autologous serum) (M8).
ND, not done.

A strong cytotoxic T cell response (CTL) was detected in one monkey vaccinated with the Tat protein and RIBI (M1) and in two monkeys vaccinated with the Tat protein and Alum (M4 and M5), whereas a weaker CTL response was observed in monkey M6 immunized with Tat and Alum (FIG. 9 and Table 12).

TABLE 12

Analysis of CTL response

| Monkey | Week | Target:Effector ratio | | | | | | CTL activity |
|---|---|---|---|---|---|---|---|---|
| | | 1:50 | 1:25 | 1:12.5 | 1:6.25 | 1:3.125 | Average | |
| M1 | 28 | 5.9 | 4.7 | 4.1 | 7.9 | 5.3 | 5.5 | + |
| | 36 | ND | 14.4 | 8.8 | 4.9 | 6.7 | 8.7 | + |
| M2 | 28 | ND | ND | ND | ND | ND | ND | ND |
| | 36 | ND | ND | ND | ND | ND | ND | ND |
| M3 | 28 | 0 | 0 | 0 | 0 | 0 | 0 | − |
| | 36 | ND | 0 | 0.6 | 0.5 | 2.0 | 0.7 | − |
| M4 | 28 | 0 | 0 | 1.1 | 1.1 | 2.6 | 0.9 | − |
| | 36 | ND | 2.7 | 8.3 | 15 | 1.9 | 6.9 | + |
| M5 | 28 | 4.9 | 3.9 | 4.7 | 5.5 | 1.7 | 4.1 | + |
| | 36 | 0 | 1 | 0 | 0 | 0 | 0.2 | − |
| M6 | 28 | 0 | 2.6 | 1.1 | 7.2 | 7.2 | 3.6 | +/− |
| | 36 | ND | 0 | 0 | 0 | 0 | 0 | − |
| M7 | 36 | 0 | 0 | 0 | 0 | 0 | 0 | − |
| M8 | 36 | 0 | 0 | 0 | 0 | 0 | 0 | − |

[a]The assay was performed as described in Table 6. Monkeys M1-3 were immunized with 10 µg of recombinant Tat in 250 µl of autologous serum and 250 µl of RIBI; monkeys M4-6 were inoculated with 10 µg of recombinant Tat in 250 µl of autologous serum and 250 µl of Alum; two control monkeys were inoculated with RIBI (250 µl and 250 µl of autologous serum) (M7) and Alum (250 µl and 250 µl of autologous serum) (M8).
ND, not done.

At week 44, the presence of total antiviral activity (TAA) was determined. TAA was measured as the ability of PBMC from monkeys vaccinated with recombinant Tat protein, cultured in the presence of autologous serum, to be resistant to SHIV 89.6P infection (Table 13).

TABLE 13

Analysis of the presence of total antiviral activity (TAA)[a]

| | Days after infection | |
|---|---|---|
| | 7 | 17 |
| Monkey ID | Minimum infectious dose ($TCID_{50}$/cell) | Minimum infectious dose ($TCID_{50}$/cell) |
| M1 | $10^{-2}$ | $10^{-2}$ |
| M2 | $10^{-4}$ | $10^{-4}$ |
| M3 | $10^{-3}$ | $10^{-3}$ |
| M4 | $10^{-2}$ | $10^{-2}$ |
| M5 | $10^{-2}$ | $10^{-2}$ |
| M6 | $10^{-3}$ | $10^{-3}$ |
| M7 | $10^{-3}$ | $10^{-3}$ |
| M8 | $10^{-4}$ | $10^{-3}$ |

[a]PBMC were collected at week 44 from monkeys vaccinated with the recombinant Tat protein (10 µg) and RIBI (M1-3) or Alum (M4-6) and from control monkeys inoculated with RIBI (M7) or Alum (M8). PBMC, purified by Ficoll gradient and seeded in triplicate at $5 \times 10^5$/200 µl per well in 48-well plates, were grown in RPMI 1640 containing 10% FCS and 5% of autologous plasma previously heated at 56° C. for 30 min., in the presence of an anti-CD3 monoclonal antibody (5 ng/ml) and and IL-2 (2 U/ml), for 48-72 hours at 37° C. Cells were infected with serial dilutions of the chimeric virus SHIV 89.6P ($10^{-2}$, $10^{-3}$, $10^{-4}$, $10^{-5}$ TCID50/cell) for 2 hours at 37° C., washed 3 times with PBS-A and resuspended in 50% of conditioned medium and 50% of fresh medium at $5 \times 10^5$ cells/ml/well. At days 3, 7, 10, 14 and 17 after infection, aliquots of culture medium were collected and substituted with equal volumes of fresh medium. Virusreplication was determined in cell supernatants by p27 Gag ELISA (Coulter International, Miami, FL). The results are shown as the minimum infectious dose of SHIV (TCID50/cell) at days 7 and 17 after infection able to infect monkey lymphocytes.

The results demonstrate the presence of soluble antiviral activity mediated by CD8+ T lymphocytes (CAF) (Table 14). An overall increase of CAF activity was observed in vaccinated monkeys as compared to control animals.

TABLE 14

Analysis of the presence of soluble antiviral activity mediated by CD8+ T lymphocytes (CAF)[a]

| Monkey ID | Weeks after the primary immunization | % inhibition of viral replication | |
|---|---|---|---|
| | | Acute infection | Chronic infection |
| M1 | 0 | 8 | 30 |
| | 32 | 53 | 53 |
| M2 | 0 | 36 | 0 |
| | 32 | 60 | 27 |
| M3 | 0 | 0 | 37 |
| | 32 | 55 | 29 |
| M4 | 0 | 45 | 0 |
| | 32 | 85 | 66 |
| M5 | 0 | 41 | 0 |
| | 32 | ND | ND |
| M6 | 0 | 49 | 18 |
| | 32 | 34 | 41.4 |
| M7 | 0 | 39 | 39 |
| | 32 | 71 | 44 |
| M8 | 0 | 37 | 0 |
| | 32 | 76 | 26.8 |

[a]Analysis of the presence of soluble antiviral activity mediated by CD8+ T lymphocytes (CAF) from monkeys vaccinated with recombinant Tat protein (10 μg) and RIBI (M1-3) or Alum (M4-6), and from control monkeys inoculated with RIBI (M7) or Alum (M8). Acute infection was tested on CEM x 174 cells infected with SHIV 89.6P. The assay was performed as described in Table 7 and the results refer to day 7 after infection. The presence of CAF on the chronic infection system was tested in the U1 cell line (Ref. 47), which is a promonocytic human cell line chronically infected by HIV-1. UI cells, seeded at $1 \times 10^4$ cells/200 μl per well in 96-well plates, were incubated with PMA ($10^{-8}$ M) to induce reactivation of HIV-1 infection, with or without different volumes (50 μl, 5 μl, 0.5 μl) of culture supernatants from CD8+ T lymphocytes derived from vaccinated and control monkeys. Three days after PMA treatment, the presence of HIV-1 in the culture medium was determined by RT assay or p24 Gag ELISA. The results are shown as % of inhibition of HIV-1 replication in cells treated with CD8+ T cells supernatants compared to untreated cells. The results of inhibition of acute and chronic infection refer to cells treated with 5 μl of CD8+ supernatants.

The production of cytokines (γIFN, IL-4, TNFα) and of the RANTES chemokine from PBMC of monkeys vaccinated with Tat and RIBI (M1-3) or Tat and Alum (M4-6) and control monkeys M7 and M8 was also determined (Table 15).

TABLE 15

Analysis of cytokine and chemokine production

| | Control | | | | PHA | | | | TT | | | |
|---|---|---|---|---|---|---|---|---|---|---|---|---|
| Monkey | γIFN | IL-4 | TNFα | RANTES | γIFN | IL-4 | TNFα | RANTES | γIFN | IL-4 | TNFα | RANTES |
| M1 | —/— | —/— | —/— | —/— | 988/1096 | —/— | 948/— | 1788/2564 | —/— | —/3.8 | —/— | Nd/Nd |
| M2 | —/— | —/— | 126/— | —/— | 325/280 | —/— | 244/172 | 292/284 | 86/66 | —/— | —/— | Nd/Nd |
| M3 | Nd/Nd | Nd/Nd | Nd/Nd | Nd/Nd | Nd/Nd | Nd/Nd | Nd/Nd | Nd/Nd | Nd/Nd | Nd/Nd | Nd/Nd | Nd/Nd |
| M4 | —/— | —/— | —/— | —/— | 426/66 | —/— | 98/— | —/284 | —/— | —/— | —/224 | Nd/Nd |
| M5 | —/— | —/— | 48/— | —/— | 279/303 | —/— | 416/— | 536/608 | —/— | —/— | —/— | Nd/Nd |
| M6 | —/— | —/— | —/— | 246/— | 255/137 | —/— | —/— | 1124/268 | —/— | —/— | —/266 | Nd/Nd |
| M7 | —/— | —/— | —/— | —/— | 150/169 | —/— | 40/— | 1228/976 | —/— | —/4 | —/nd | Nd/Nd |
| M8 | —/— | —/— | —/— | —/— | 0/0 | 20/32 | 60/— | 2160/1588 | —/— | —/— | —/nd | Nd/Nd |

| | Tat (1 μg) | | | | Tat (5 μg) | | | |
|---|---|---|---|---|---|---|---|---|
| Monkey | γIFN | IL-4 | TNFα | RANTES | γIFN | IL-4 | TNFα | RANTES |
| M1 | —/— | —/— | —/— | —/— | —/— | —/— | 16/— | —/— |
| M2 | —/— | —/— | —/— | —/— | —/— | —/— | —/— | —/— |
| M3 | Nd/Nd | Nd/Nd | Nd/Nd | Nd/Nd | Nd/Nd | Nd/Nd | Nd/Nd | Nd/Nd |
| M4 | —/— | —/— | 378/430 | —/— | —/— | —/— | 344/352 | —/— |
| M5 | —/— | —/— | —/— | —/— | —/— | —/— | —/— | —/— |
| M6 | —/— | —/5 | —/— | —/— | —/78 | —/— | 150/— | —/— |
| M7 | —/40 | —/3.3 | 84/— | —/— | —/— | —/3.2 | —/— | —/— |
| M8 | —/— | —/4.8 | —/— | —/— | —/— | —/10 | —/— | 726/528 |

[a]Analysis of the production of cytokines and chemokines after 48 and 96 hours of culture (48/96) from PBMC of monkeys vaccinated with 10 μg of Tat and RIBI (M1-3) or Alum (M4-6). Control monkeys (M7 and M8) were inoculated with RIBI or Alum adjuvants, respectively. PBMC, withdrawn at week 44 and purified by Ficoll gradient, were seeded at $1 \times 10^6$ cells/ml per well in 24-well plates and grown in RPMI 1640 containing 10% FCS. PBMC were unstimulated (control), to evaluate the spontaneous release of cytokines and chemokines, or stimulated with PHA (2 μg/ml), the tetanus toxoid (TT, 5 μg/ml) or Tat (1 or 5 μg/ml). Aliquots of culture supernatants were collected 48 and 96 hours following stimulation to determine the presence of cytokines and chemokines, by means of commercial ELISA kits from BioSource International (Camarillo, CA, USA) to assay cytokines production, and from R&D Systems (Abgidon, Oxon, UK) to evaluate RANTES production. The results are shown as pg/ml at 48 and 96 hours of culture (48/96), respectively. Cut-off values were (pg/ml): γIFN, 31.2; IL-4, 3.12; TNFα, 15.6; RANTES, 6.25.

(—), values were lower than corresponding cut-off values.

Nd: not done.

Moreover, at week 15 five monkeys vaccinated with the recombinant protein (M2-6), showed a positive reaction to the skin test to Tat, with a strong delayed hypersensitivity reaction (Table 16 and FIG. 19). In monkeys 4 and 5 the skin test reaction was even stronger in the following weeks (Table 16).

TABLE 16

Skin-test to Tat[a]

Weeks from the primary immunization

| Monkey | 11 | 15 | 21 | 28 | 32 | 36 | 44 |
|---|---|---|---|---|---|---|---|
| M1 | − | − | − | − | − | − | − |
| M2 | − | + | + | +/− | +/− | + | +/− |
| M3 | +/− | + | +/− | +/− | − | − | − |
| M4 | − | + | ++ | ++ | ++ | ++ | ++ |
| M5 | +/− | + | ++ | + | ++ | ++ | + |
| M6 | − | + | +/− | +/− | − | − | − |
| M7 | ND | ND | ND | ND | ND | ND | ND |
| M8 | ND | ND | ND | ND | ND | ND | ND |

[a]Tat (1 and 5 µg) in 150 µl of PBS-0.1% BSA or the buffer alone were inoculated by the intradermal route in a shaved area of the back of vaccinated monkeys. Control animals were not inoculated (ND, not done) at weeks 11, 15, 21, 28, 32, 36 and 44 after the first immunization. Monkeys M1-3 were vaccinated with 10 µg of recombinant Tat protein in 250 µl of autologous and 250 µl of RIBI; monkeys M4-6 were vaccinated with 10 µg of recombinant Tat protein in 250 µl of autologous serum and 250 µl of Alum; two control monkeys were inoculated with RIBI (250 µl and 250 µl of autologous serum) (M7) or Alum (250 µl and 250 µl of autologous serum) (M8). The presence of an erythematous nodule after 48-72 hours was suggestive of a delayed hypersensitivity reaction (DTH). ++, ⌀ ≧ 5 mm; +, ⌀ ≧ 1-4 mm; +/+, erythema without hardening; −, ⌀ < 1 mm.

The post-challenge results indicate that 4/6 (67%) vaccinated monkeys were protected against infection with 10 $MID_{50}$ of SHIV 89.6P, as shown by the results of the virological assays (Table 17). Particularly, p27 Gag antigen was not detected in plasma of monkeys M1, M2, M4 and M6, proviral DNA was not found by PCR in lymphocytes from these monkeys and cytoviremia was negative. Monkeys M3 and M5 were infected as shown by the presence of p27 Gag antigen in the plasma, by detection of proviral DNA in the cells and by a positive cytoviremia (Table 17). Both controls (M7 and M8) resulted infected, based on the same virological assays. To further control the infectivity of the viral dose used for the challenge, another naive monkey (M13) was added to the control animals and infected with 2.85 $MID_{50}$ of SHIV 89.6P (corresponding to a dose of virus 3.5-fold lower than the dose used for the challenge of the animals in the protocol). Monkey M13 resulted to be infected based on all the virological assays. To confirm that the animals were exposed to the virus, the presence of antibodies against SIV antigens, encoded by the chimeric SHIV 89.6P virus (Gag, Pol, RT, Nef), was analyzed as already described in this Example. The presence of anti-SIV antibodies in the monkeys that were negative for the virological parameters (M1, M2, M4 and M6) confirm that these animals were exposed to the virus and indicates that an abortive infection of SHIV had occurred in these monkeys. Monkeys that showed low anti-SIV antibody titers were studied for in vitro production of specific antiviral IgG (IVAP) (Ref. 177, 178) according to the following method. PBMC ($2\times10^6$/well) were seeded in 24-well plates and stimulated with PWM (2 µg/ml, Sigma, St. Louis, USA). Following 7 days incubation (at 37° C. in the presence of 5% $CO_2$ and 95% humidity) culture supernatants were collected to assay for anti-HIV antibody production by an Elisa commercial kit for the detection of HIV-1 and HIV-2 antibodies (Abbott, HIV-1/HIV-2 EIA Third Generation Plus). All challenged monkeys resulted positive for the production of anti-HIV Env antibodies, since HIV-1 Env is present in the SHIV 89.6P.

TABLE 17

Analysis of virological parameters

| | Days after challenge with SHIV89.6P | | | | | | | | | | | |
|---|---|---|---|---|---|---|---|---|---|---|---|---|
| | 15 | | | | 30 | | | | 60 | | | |
| Monkey | p27[a] (pg/ml) | DNA PCR (copies/µg)[b] | Cyto-viremia[c] | anti-SIV IgG[d] | p27 (pg/ml) | DNA PCR (copies/pg) | Cyto-viremia | anti-SIV IgG | p27 (pg/ml) | DNA PCR (copies/pg) | cyto-viremia | anti-SIV IgG |
| M1 | <20 | <1 | Neg | 1:2 | <20 | <1 | Neg | 1:2 | <20 | <1 | Neg | 1:2 |
| M2 | <20 | <1 | Neg | 1:2 | <20 | <1 | Neg | 1:2 | <20 | <1 | Neg | 1:2 |
| M3 | 73.3 | 855 | 707.3 | Neg | 26.22 | 959 | 74.95 | Neg | <20 | 71 | <1 | 1:10 |
| M4 | <20 | <1 | Neg | 1:2 | <10 | <1 | Neg | 1:2 | <20 | <1 | Neg | 1:2 |
| M5 | 964 | 1147 | >2818.3 | Neg | 20.8 | >$10^6$ | 78 | 1:2 | <20 | 65 | 44.6 | 1:10 |
| M6 | <20 | <1 | Neg | 1:8 | <20 | <1 | Neg | 1:8 | <20 | <1 | Neg | 1:6 |
| M7 | 287.8 | 838 | 707.9 | >1:50 | 65.2 | 858 | 354.8 | >1:50 | <20 | 439 | 11.2 | 1:6400 |
| M8 | 106.7 | 376 | 707.9 | 1:2 | <20 | 311 | 44.6 | 1:5 | <20 | 56 | 2.8 | 1:6400 |
| M13 | 1876 | +[f] | +[e] | ND | <20 | +[f] | ND | 1:1600 | <20 | 43 | ND | 1:3200 |

Analysis of the virological parameters after challenge of monkeys vaccinated with 10 µg of recombinant Tat protein and RIBI (M1-3) or Alum (M4-6). Control monkeys (M7 and M8) were inoculated with RIBI or Alum, respectively. Monkey M13 was a naive animal infected with 2.85 $MID_{50}$ of SHIV 89.6P.
[a]The plasma antigenemia was evaluated by p27 Gag ELISA (Innogenetics, Belgium) and it is expressed as p27 values (pg/ml). Neg, the value was lower than the corresponding cut-off value (18 pg/ml).
[b]DNA was purified by whole blood using the QIAamp blood kit (Angiogen Gmbh and Qiagen Inc., Hilden, Geramny). The quality of the DNA was controlled by PCR amplification of the β-globin gene, as previously described (Ref. 141). The presence of proviral DNA was analyzed by semiquantitative PCR amplification of SIV gag. PCR was performed on 1 µg of cellular DNA using primers SG1096Ngag (corresponding at nucleotides 1096-1119 on SIVmac251 genome: SEQ. ID. NO. 35 5'TTAGGCTACGACCCGGCGGAAAGA3') and SG1592CgagD (mapping at nucleotides 1569-1592 of SIVmac251 genome: SEQ. ID. NO. 36 5'ATAGGGGGTGCAGCCTTCTGACAG3') which amplify a 496 base pair fragment of the SHIV gag gene, as described (Ref. 153). To quantify the number of copies of proviral DNA, in each experiment a standard curve was prepared using the plasmid pCMRII-Agag (containing a 100 base pair deletion in the gag gene of SIVmac251) as a template DNA and the primers described above that amplify a 396 base pair DNA fragment. PCR products were analyzed by electrophoresis and quantified by densitometric analysis (Ultrascan LX Enhancer Laser, LKB, Bromma, Sweden). The relationship between the OD values and the number of molecules of the Agag plasmid was correlated by means of linear regression analysis (Statgraphics, Manugistics, Inc. Cambridge, MA). The OD values were linear up to 1000 molecules (coefficient of correlation = 0.954 ± 0.026). The number of copies of SHIV proviral DNA/µg of cellular DNA was determined interpolating the OD values of each sample to the standard curve. The sensitivity of the assay was 1 copy of provirus/µg of DNA.
[c]Cytoviremia was determined in co-coltivation assays. To this aim $1 \times 10^4$ CEM x 174 cells were cultivated in the presence of serial dilutions of CD-8 depleted PBMC under study (a total of 12 dilutions, from $1 \times 10^6$ to $3.9 \times 10^3$ cells per well) in 96-well plates. At days 3, 7 and 10 after infection, 150 µl were removed to assay the presence of p27 Gag by ELISA (Innogenetics, Belgium) and substituted with an equal volume of fresh medium. The results were analyzed by means of the Reed and Muench formula to determine the number of productively infected PBMC per milion of total cells.
[d]The presence of antibodies against SHIV was determined on serial dilutions of animal plasma tested in duplicate using the Elavia Ac-Ab-Ak II kit (Diagnostic Pasteur, Paris, France), according to the manufacturer's instructions. The highest dilution at which plasma values were higher than the cut-off value is shown.
[e]Virus isolation was performed, instead of cytoviremia, for monkey M13. To this aim PBMC ($3 \times 10^6$) from monkeys infected with different doses of SHIV 89.6P, purified by Ficoll, were cultivated with CEM x 174 cells ($1 \times 10^6$) in 1 ml of medium containing 10% FCS. After 24 hours, cells were diluted at $1 \times 10^6$/ml and cultivated for three days. Two ml of medium were then collected and cells were re-seeded at $3 \times 10^5$/ml in 7 ml. The excess of cells was discarded. This procedure was repeated twice a week for 4 weeks. The presence of virus was determined by p27 Gag ELISA (Innogenetics, Belgium) and then by RT assay. Virus isolation was considered positive (+) when both assays (p27 and RT) were positive in 3 sequential samples. Conversely, virus isolation was considered negative (−).
[f]A qualitative DNA-PCR was performed for monkey M13.

The virological data overlap the absolute number of CD4 lymphocytes that resulted dramatically reduced in infected monkeys (M3, M5, M7, M8) and high and stable in the virus-negative animals (M1, M2, M4, M6) as shown in Table 18.

istered to animals are amplified in *E. Coli* (strain DH5) according to standard procedures (Ref. 110) and to protocols established by the "European Agency for the evaluation of medical products; Human Medicine Evaluation Unit" (Technical Report Series No. 17 Jan. 1997), purified by two CsCl

TABLE 18

FACS analysis of CD4+ and CD8+ lymphocytes[a]

| | Days post challenge with SHIV89.6P | | | | | | | | | | | |
|---|---|---|---|---|---|---|---|---|---|---|---|---|
| | 0 % (cells/µl) | | | 15 % (cells/µl) | | | 30 % (cells/µl) | | | 60 % (cells/µl) | | |
| Monkey | CD4+ | CD8+ | CD4+/CD8+ | CD4+ | CD8+ | CD4+/CD8+ | CD4+ | CD8+ | CD4+/CD8+ | CD4+ | CD8+ | CD4+/CD8+ |
| M1 | 32.1 (1490) | 53 (2460) | 0.6 | ND | ND | ND | 30.8 (2420) | 57.3 (4500) | 0.54 | 30.6 (2460) | 57.9 (4670) | 0.53 |
| M2 | 27.7 (1550) | 45.3 (2530) | 0.6 | ND | ND | ND | 35.5 (2120) | 43.7 (2610) | 0.81 | 29.6 (2000) | 42.4 (2870) | 0.7 |
| M3 | 33 (1120) | 39.3 (1340) | 0.84 | ND | ND | ND | 3.1 (190) | 75.6 (4660) | 0.04 | 6.2 (240) | 70 (2750) | 0.09 |
| M4 | 16.6 (670) | 68.3 (2740) | 0.24 | ND | ND | ND | 17.25 (2050) | 68.7 (8180) | 0.25 | 15.5 (1520) | 75 (7350) | 0.21 |
| M5 | 36.3 (2770) | 43.9 (3350) | 0.83 | ND | ND | ND | 1.1 (90) | 82.3 (1300) | 0.01 | 4.1 (480) | 75.5 (8730) | 0.05 |
| M6 | 35.3 (1210) | 43.4 (1490) | 0.81 | ND | ND | ND | 35.9 (1240) | 45.5 (1570) | 0.79 | 37.8 (3700) | 43.7 (4280) | 0.86 |
| M7 | 36.1 (1610) | 31.3 (1400) | 1.15 | ND | ND | ND | 7.4 (480) | 66.1 (4260) | 0.11 | 13.7 (860) | 56.7 (3550) | 0.24 |
| M8 | 25.7 (850) | 51.3 (1710) | 0.5 | ND | ND | ND | 3.3 (210) | 76.2 (4840) | 0.04 | 8.1 (590) | 64.9 (4670) | 0.13 |
| M13 | 40.5 (2590) | 39.7 (2544) | 1.01 | 38.4 (434) | 33.6 (380) | 1.14 | 35.1 (1721) | 32.2 (1479) | 1.16 | 3.1 (111) | 62.3 (2225) | 0.05 |

[a]FACS analysis of CD4+ and CD8+ lymphocytes from monkeys vaccinated with 10 µg of recombinant Tat protein and RIBI (M1-3) or Alum (M4-6). Control monkeys (M7 and M8) were inoculated only with RIBI or Alum adjuvants, respectively. Monkey M13 was a naive animal infected with 2.85 MID$_{50}$ of SHIV 89.6P. Analysis was performed by fluorescence-activated-cell-sorter (FACS) as described (Ref. 137), using labeled-monoclonal antibodies (anti-CD4-FITC, BioSource; anti-CD8-PerCp, Becton-Dickinson).
ND, not done.

The results before the challenge indicate that Tat as the immunogen, as well as RIBI and Alum as the adjuvants (or ISCOM that was used as adjuvant in the last boost), were well tolerated by the animals and were non-toxic, confirming the results of safety and tolerability of the immunization with Tat obtained in the first pilot experiment. Moreover, these data confirm the observations of the first pilot experiment, supporting additional evidence to the fact that the recombinant Tat protein elicits a strong humoral and cellular response specific to Tat with antiviral effects in vitro and in vivo. The post-challenge results (4/6 protected monkeys) confirm the expectation of the in vitro results and indicate that an anti-Tat vaccine induces protection against infection and therefore against the disease. The follow-up of the two vaccinated and infected monkeys will clarify the effects of the vaccination on disease progression.

Example 5

Inoculation in *Macaca fascicularis* of an Anti-Tat DNA Vaccine Analysis of Safety, Tolerability, Specific Immune Response and Efficacy of Protection Against Viral Challenge It is proposed the direct inoculation of DNA of the plasmid pCV-Tat, containing the cDNA of the tat gene, and of the plasmid pCV0 as control DNA. Plasmid DNAs to be admingradients and dialyzed for 48-72 hours against 100 volumes of PBS. DNA are then checked by restriction enzyme digestion. The functionality of the plasmid DNA is controlled by transfection of 5-10 µg of DNA using calcium-phosphate techniques (Ref. 110) in H3T1 cells ($1\times10^6$), which contain an integrated copy of the reporter plasmid HIV-1 LTR-CAT, and, 48 hours later, by the analysis of CAT activity (Ref. 55). The tolerability, the safety, the ability to elicit a specific immune response (both humoral and cellular) and the efficacy of protection against the virus challenge following immunization with pCV-Tat plasmid DNA were evaluated in cynomolgus monkeys (*Macaca fascicularis*). In a first pilot experiment, three monkeys were immunized according to the following schedule: monkey M1 was inoculated with 200 µg of pCV-Tat in 300 µl of PBS by the i.d. route in 2 sites of the back, near the axillary lymph nodes (150 µl/site); monkey M2 was inoculated with 500 µg of pCV-Tat in 500 µl of PBS by the i.m. route in 2 sites of the back (250 µl/site). At days 1 or 5 before the i.m. inoculation, 250 µl of physiological solution, containing 0.5% bupivacaine and 0.1% methylparaben, were injected in the two sites, previously marked, where plasmid DNA had to be inoculated. This was performed in order to increase the uptake and expression of DNA in the muscle (Ref. 37, 45). Monkey M3 was not inoculated and was used as a control animal. However, starting from week 10, this monkey was inoculated with 6 µg(5+1 µg) i.d. of Tat as a control for skin tests. Ten ml of blood were withdrawn from all monkeys 42 and 35 days preceding the first inoculation for analysis of basal parameters. Monkeys were inoculated at time 0 and after 5, 10, 15, 22, 27, 32 and 37 weeks. Finally, at week 42, animals received the last boost with recombinant Tat protein (16 µg) in 200 µl of ISCOM and 300 µl of PBS. Animals were observed daily for clinical parameters as described in Example 4. Moreover, 10 ml of blood were withdrawn the same day of inoculation as described in Example 4. The protective effect of vaccination was determined after challenge of the monkeys with 10 MID$_{50}$ of SHIV89.6P, that was injected by the intravenous route at week 65. The post-challenge follow up, still ongoing, was performed as described in Example 4. The results of this experiment are as follows. In two vaccinated monkeys and in the control monkey no alterations of clinical, haematological and behavioristic parameters were observed. Inflammatory signs or neovascularization in the site of injection were not observed. These results indicate that the pCV-Tat DNA was well tolerated by the animals and was non-toxic at the doses and inoculation routes used in the experiment. Monkey M1, vaccinated with 200 µg of DNA by the i.d. route, developed Tat-specific IgG antibodies since week 32 (FIG. 11). The antibody titers (from week 32 to week 58) ranged between 1:100 and 1:800 (FIG. 12). At week 37, epitope mapping analysis (performed as described in legend to FIG. 4) showed that these antibodies were directed against specific regions of Tat, mapping at aa 1-20, aa 46-60 and aa 65-80, with titers of 1:200, 1:100 and 1:50, respectively (data not shown). In monkey M2, vaccinated with 500 µg of DNA by the i.m. route, anti-Tat antibodies were barely detected (with a 1:50 titer, not shown) for the entire period of the study. The results are shown in FIG. 11. The ability of plasma from monkey M1, vaccinated with 200 µg of DNA by the i.d. route, to neutralize Tat activity was tested by assaying the inhibition of the rescue of viral replication in HLM1 cells incubated with exogenous Tat protein, as described in Example 4. This assay showed that the plasma of monkey M1, diluted 1:2, and obtained at week 37, reduced viral replication induced by 30 ng/ml of exogenous Tat. Conversely, the plasma of the same monkey obtained at time 0 (preimmune) did not block extracellular Tat (Table 19).

TABLE 19

Neutralizing activity of plasma on rescue of viral infection induced by extracellular Tat[a]

| Samples | Inhibition |
| --- | --- |
| Tat + M1 preimmune | 0 |
| Tat + M1 immune | 51 |

[a]The ability of anti-Tat antibodies to neutralize Tat activity was determined in HLM1 cells by adding 30 ng/ml of recombinant Tat protein, previously incubated with an equal volume of plasma obtained at time 0 (preimmune) or at week 37 (immune) from monkey M1, vaccinated with 200 µg of pCV-Tat plasmid DNA by the i.d. route. The assay was performed and the results expressed as described in Table 4.

The results shown in Table 20 demonstrate the presence of a proliferative response to Tat at week 42 in monkey M1 immunized with 200 µg of DNA by the i.d., whereas in monkey M2 this type of cellular response was not detected.

TABLE 20

Proliferative response to Tat[a]

| Monkey | Stimulus | Weeks after the primary immunization | | | | | | | |
| --- | --- | --- | --- | --- | --- | --- | --- | --- | --- |
| | | 15 | 22 | 27 | 32 | 37 | 42 | 48 | 58 |
| M1 | PHA | 32.9 | 45 | 89.3 | 40.5 | 3.1 | 13.3 | ND | 13.1 |
| | TT | 0.8 | 2.7 | 1.5 | 1.3 | 0.6 | 9 | 1.2 | 1.6 |
| | Tat | 0.9 | 1.7 | 1.2 | 1.1 | 1.1 | 5.9 | 1 | 1 |
| M2 | PHA | 11.7 | 18.5 | 21.8 | 32.2 | 1.1 | 6.2 | 7 | 18.9 |
| | TT | 0.9 | 1.8 | 0.8 | 1.1 | 1 | 1.5 | 1.1 | 1 |
| | Tat | 0.8 | 1.4 | 0.9 | 1.1 | 1.1 | 1.3 | 1.1 | 1 |
| M3 | PHA | 5.1 | 19.9 | 18.2 | 6.6 | 8.1 | 77.8 | ND | 2.1 |
| | TT | 7.2 | 6.2 | 5.5 | 2.8 | 5.6 | 36.8 | 1 | 2.1 |
| | Tat | 2.1 | 1.4 | 2.2 | 0.7 | 1.5 | 2.8 | 0.8 | 0.9 |

[a]PBMC were isolated, stimulated with PHA (4 µg/ml), tetanus toxoid (TT) and Tat (1 or 5 µg/ml) and tested as described in Table 5. Monkeys were vaccinated with 200 µg (M1) of pCV-Tat by the i.d. route or with 500 µg (M2) of pCV-Tat by the i.m. route. Monkey (M3) was not vaccinated but was inoculated since week 10 with 6 µg (5 + 1 µg) i.d. of Tat as a control for skin tests.
ND: not done.

The anti-Tat cytotoxic activity (CTL) was detected in monkey M1 at week 42 and 48 and in monkey M2 at week 48. Furthermore, a positive CTL response was observed at week 48 in monkey M3 which was inoculated since week 10 with 6 µg of Tat as a control for skin tests (Table 21).

TABLE 21

Analysis of Tat-specific cytotoxic activity (CTL)[a]

| Monkey | Week | Target:Effector ratio | | | | | CTL activity |
| --- | --- | --- | --- | --- | --- | --- | --- |
| | | 1:50 | 1:25 | 1:12.5 | 1:6.25 | 1:3.125 | Media | |
| M1 | 42 | 27.4 | 27.8 | 17.1 | 9.8 | 3.9 | 17.2 | + |
| | 48 | ND | ND | 21.3 | 0 | 11.7 | 11 | + |
| M2 | 42 | 1.2 | 5.9 | 2.4 | 1 | 0 | 2.1 | − |
| | 48 | ND | ND | ND | 57 | 25.1 | 41 | + |
| M3 | 42 | 0 | 0 | 0 | 1.2 | 0 | 0.6 | − |
| | 48 | ND | 12.4 | 4.2 | 0 | 0 | 0 | + |

[a]The assay was carried as described in Table 6. Monkeys were vaccinated with 200 µg (M1) of pCV-Tat by the i.d. route or with 500 µg (M2) of pCV-Tat by the i.m. route. Monkey (M3) was not vaccinated but was inoculated since week 10 with 6 µg (5 + 1 µg) i.d. of Tat as a control for skin tests.
ND: not done.

The results shown in Table 22 indicate at week 52 the presence of total antiviral activity (TAA) in both monkeys vaccinated with 200 and 500 μg of DNA.

TABLE 22

Analysis of total antiviral activity (TAA)[a]

| | Days post infection | |
|---|---|---|
| | 7 | 17 |
| Monkey | Minimum infectious dose (TCID$_{50}$/cell) | Minimum infectious dose (TCID$_{50}$/cell) |
| M1 | $10^{-4}$ | $10^{-4}$ |
| M2 | $10^{-4}$ | $10^{-4}$ |
| M3 | $10^{-8}$ | $10^{-8}$ |

[a]The assay was performed as described in Table 13. Monkeys were inoculated with 200 μg (M1) of pCV-Tat by the i.d. route or with 500 μg of pCV-Tat by the i.m. route. Monkey (M3) was not inoculated but since week 10 received 6 μg (5 + 1 μg) i.d. of Tat as a control for skin tests. PBMC were collected at week 52 from the primary immunization and were infected with SHIV 89.6P ($10^{-2}$, $10^{-4}$, $10^{-6}$, $10^{-8}$ TCID$_{50}$/cell) The results arerepresented as the minimum infectious dose of SHIV (TCID$_{50}$/cell) that was still able to infect the cells.

The results shown in Table 23 indicate the presence of soluble antiviral activity (CAF) mediated by CD8+ T lymphocytes, at week 22 and 27, in both vaccinated monkeys. This activity was lower in the control monkey.

TABLE 23

Analysis of the CD8+ cell mediated soluble antiviral activity (CAF)[a]

| Monkey | Weeks from primary immunization | % inhibition of viral replication | |
|---|---|---|---|
| | | Acute infection | Chronic infection |
| M1 | 22 | 62 | 27 |
| | 27 | 56 | 25 |
| M2 | 22 | 74 | ND |
| | 27 | 28 | ND |
| M3 | 22 | 24 | ND |
| | 27 | 37 | 22 |

[a]Analysis of the presence of soluble antiviral activity produced by CD8+ T lymphocytes (CAF) derived from monkeys inoculated with 200 μg (M1) and 500 μg (M2) of pCV-Tat and from the monkey M3. The antiviral activity was assayed on acute and chronic infection in CEM x 174 cells infected with SHIV 89.6P and in OM-10-1 cells chronically infected with HIV-1, as described in Table 7. The results are represented as the percentage (%) of inhibition of viral replication in cells treatedwith supernatants from CD8+ T lymphocytes compared to untreated cells. The results of the acute and chronic infection shown in the table refer to samples treated with 5 μl of CD8+ culture supernatants.
ND, not done.

The results shown in Table 24 demonstrate that monkey M1, inoculated with 200 μg of DNA by the i.d. route, had a positive skin test to Tat at week 22.

TABLE 24

Skin test to Tat[a]

| | Monkey | | |
|---|---|---|---|
| Weeks post immunization | M1 | M2 | M3 |
| 10 | − | − | − |
| 15 | − | − | − |
| 22 | + | − | − |

TABLE 24-continued

Skin test to Tat[a]

| | Monkey | | |
|---|---|---|---|
| Weeks post immunization | M1 | M2 | M3 |
| 27 | − | − | − |
| 32 | − | − | − |
| 37 | − | − | − |
| 42 | − | − | − |
| 48 | − | − | − |
| 52 | − | − | − |
| 58 | − | − | − |

[a]Tat (1 and 5 μg) in 150 μL of PBS-0.1% BSA or the buffer alone (control) were inoculated i.d. in a previously thrichotomized area of the upper back of the vaccinated animals and in the control monkey (control for the specificity of the response) at weeks 10, 15, 22, 27, 32, 37, 42, 48, 52, and 58 from the primary immunization. The monkey M1 was inoculated i.d. with 200 μg of DNA of the plasmid pCV-Tat, whereas the macaque M2 received 500 μg of the same plasmid, i.m.. Monkey M3 (control) was not vaccinated but since week 10 received 6 μg (5 + 1 μg) i.d. of Tat as a control for skin tests. The appearance of an erythematous nodule, 48 to 72 hours later, indicated the presence of delayed-type hypersensitivity (DTH): ++, φ ≧ 5 mm; + φ 1-4 mm; ±, erythema without hardening; −, φ < 1 mm.

These results indicate that the plasmid pCVTat (pCVTat-DNA) was well tolerated and safe both intradermally and intramuscularly at the given doses. Moreover, these results demonstrate that the immunization with the pCVTat-DNA induces both a humoral (although lower than that induced by the immunization with the recombinant Tat protein) and cellular anti-Tat immune response with antiviral effects. Concerning the protective efficacy after challenge (performed at week 65 from the initial immunization), the virological data, including measurements of antigenemia and cytoviremia, and determination of number of proviral DNA copies (DNA-PCR) in PBMCs, indicate that the monkey M2, immunized i.m. with Tat-DNA, resulted protected upon challenge with 10 MID$_{50}$ of SHIV-89.6P, whereas the macaque M1, immunized i.d. with a smaller dose of Tat-DNA (200 μg) resulted infected, suggesting that, in regard to the immunization with DNA, the i.m. route is more effective than the i.d. inoculation. The control monkey M3 also resulted resistent to the infection. However, as previously described, this monkey, unlike the controls of the other experimental protocols, received repeated skin tests for Tat in order to control the test specificity (Table 24), and anti-Tat antibodies, although at low titers (1:100), were detected since week 32 from the beginning of the immunization (data not shown). Moreover, the proliferative response to Tat in this monkey showed a weak and sporadic reactivity to the antigen (Table 20). Finally, monkey M3 showed the presence of specific anti-Tat CTLs (Table 21). Although preliminary, these data indicate that the repeated i.d. injection of 6 μg of Tat could have resulted in the immunization of the animal and in the is protection from challenge. Thus, the monkey M3 will be considered vaccinated i.d. with the Tat protein and studied as such.

TABLE 25

Analysis of the virological parameters

| | Days post-challenge with SHIV89.6P | | | | | | | | | | | |
|---|---|---|---|---|---|---|---|---|---|---|---|---|
| | 15 | | | | 30 | | | | 60 | | | |
| Monkey | p27[a] (pg/ml) | DNA PCR (copies/µg)[b] | Cyto-viremia[c] | Anti-SIV IgG[d] | P27 (pg/ml) | DNA PCR (copies/µg)[b] | Cyto-viremia[c] | anti-SIV IgG | p27 (pg/ml) | DNA PCR (copies/µg)[b] | Cyto-viremia[c] | anti-SIV IgG |
| M1 | 1796 | 1278 | >2818.3 | 1:10 | 68.6 | 1048 | 353.9 | 1:50 | <20 | 8 | 21.3 | 1:800 |
| M2 | <20 | <1 | Neg | 1:10 | <20 | <1 | Neg | 1:50 | <20 | <1 | Neg | 1:10 |
| M3 | <20 | <1 | Neg | >1:50 | <20 | <1 | Neg | >1:50 | <20 | <1 | Neg | 1:100 |

The monkey M1 had been immunized i.d. with 200 µg of pCVTat, the monkey M2 with 500 µg of pCVTat, i.m. The macaque M3 was injected several times with 6 µg of Tat protein, intradermally, in order to control the skin test specificity. Therefore, from the time of challenge on, M3 monkey is considered as a vaccinated monkey. The virological parameters were evaluated as described in the legend to Table 17.

The FACS evaluation of the percentage and of the absolute number of the CD4 and CD8 lymphocytes confirmed the virological data, with a clear reduction (of approximately 4 folds) of the CD4 lymphocytes in the infected monkey, already at the first post-challenge analysis (day 30) and confirmed later on (day 60) (Table 26).

inoculated into the two marked sites in which successively the plasmid would have been injected. The macaques were vaccinated at time 0 and at week 6, 11, 15, 21, 28, and 32. A final booster was performed at week 36 with the recombinant Tat protein (16 µg) resuspended in 200 µl of ISCOM and 300 µl of PBS. The animals were controlled every day for clinical parameters as described in the Example 4. Moreover, 10 ml of blood were drawn 9 days before the primary immunization and at every immunization, as described in the Example 4. In order to evaluate the protective effects of the vaccination, the monkeys were challenged at week 50 from the is beginning of the immunization by intravenous (i.v.) injection of 10 MID$_{50}$

TABLE 26

FACS analysis of CD4 and CD8 subsets.

| | 0 | | | 15 | | | 30 | | | 60 | | |
|---|---|---|---|---|---|---|---|---|---|---|---|---|
| | % (cells/µl) | | | % (cells/µl) | | | % (cells/µl) | | | % (cells/µl) | | |
| Monkey | CD4+ | CD8+ | CD4+/CD8+ | CD4+ | CD8+ | CD4+/CD8+ | CD4+ | CD8+ | CD4+/CD8+ | CD4+ | CD8+ | CD4+/CD8+ |
| M1 | 27.5 (940) | 40.7 (1390) | 0.68 | ND | ND | ND | 8.1 (250) | 56.5 (1780) | 0.14 | 9.5 (360) | 69.7 (2650) | 0.14 |
| M2 | 22.2 (490) | 36.8 (810) | 0.6 | ND | ND | ND | 16.4 (580) | 42.4 (1500) | 0.39 | 10.9 (940) | 52.7 (4560) | 0.21 |
| M3 | 28.7 (1170) | 41.1 (1680) | 0.7 | ND | ND | ND | 19.5 (970) | 48.7 (2430) | 0.4 | 17.9 (900) | 52.2 2620) | 0.34 |

The analysis was performed as indicated in the legend to Table 18. The monkey M1 had been immunized i.d. with 200 µg of pCVTat plasmid DNA, the monkey M2 with 500 µg of pCVTat-DNA, i.m. The macaque M3 was vaccinated with 6 µg of Tat protein intradermally.

Based on these results a second experiment was designed in which the effects of the immunization with the pCVTat-DNA were evaluated in 3 monkeys (M9-M11) as compared to the control monkey (M12) that received the pCV0-DNA. All animals were inoculated i.m. in 2 sites on the back with a total of 1 mg of pCVTat (M9-M11) or of pCV0 (M12). Either 1 or 5 days before the vaccination, 250 µl of saline solution containing 0.5% of bupivacaine and 0.1% of methylparaben were of SHIV-89.6P. The post-challenge follow-up is still ongoing and is performed as described in the Example 4.

The results of this experiment are the following. No modifications in terms of behavior, clinical parameters, and blood chemistry were noted both in the vaccinated and in the control animals. No signs of inflammation or vascular neo-formations were detected at the injection sites. These results confirm that 1 mg of the plasmid pCVTat DNA, injected i.m., was well tolerated and non-toxic. Anti-Tat IgG were detected since week 15 (FIG. 13), with titers ranging from 1:50 to 1:100 (data not shown). Moreover, a proliferative response to Tat was detected as early as week 2 in one monkey (M11) (table 27).

TABLE 27

Proliferative response to Tat[a]

| Monkey | Stimulus | Weeks from primary immunization |||||||||||
|---|---|---|---|---|---|---|---|---|---|---|---|
| | | 2 | 6 | 11 | 15 | 21 | 28 | 32 | 36 | 40 | 44 | 50 |
| M9 | PHA | 8.9 | 9.2 | 17.1 | 58.2 | 18 | 47.1 | 43.4 | 3.1 | 72.6 | 64.6 | 7 |
| | TT | 2.9 | 1.7 | 0.9 | 1 | 1.8 | 0.7 | 1.1 | 0.8 | 1 | 7 | 2.7 |
| | Tat | 0.4 | 0.5 | 0.6 | 1.5 | 1.6 | 0.9 | 1 | 0.7 | 1.1 | 7 | 1.9 |
| M10 | PHA | 8.5 | 18 | 19.8 | ND | 10.1 | 2.2 | 14.7 | 15.2 | 4.4 | 8.4 | ND |
| | TT | 2.4 | 0.3 | 0.8 | ND | 1.1 | 0.6 | 1 | 0.9 | 0.6 | 6.4 | ND |
| | Tat | 1 | 0.3 | 0.7 | ND | 1.1 | 0.5 | 1 | 0.9 | 0.7 | 4.2 | ND |
| M11 | PHA | 25.7 | 43.3 | | 12.1 | 27.8 | 3.4 | 21.3 | 14.1 | 15.9 | 25.8 | ND |
| | TT | 4.2 | 1.9 | 1.3 | 0.9 | 1.1 | 3.6 | 1.2 | 0.8 | 0.3 | 1.8 | ND |
| | Tat | 5.1 | 0.8 | 1.6 | 0.7 | 1.1 | 1.1 | 1.2 | 0.7 | 0.7 | 3 | ND |
| M12 | PHA | 28.7 | 30.9 | 41 | 50.7 | 30.8 | 7.6 | 43 | 22.6 | 34.6 | 19.9 | 55.1 |
| | TT | 3.2 | 1.6 | 0.9 | 5.2 | 1.6 | 1.6 | 1.3 | 1.1 | 1 | 0.7 | 3.1 |
| | Tat | 3.2 | 1.4 | 0.8 | 1.3 | 1 | 1.6 | 1 | 0.8 | 1 | 1.6 | 1.3 |

[a]PBMC were isolated, stimulated with PHA (4 µg/mL), or tetanus toxoid (TT, 10 µg/mL), or Tat (1 and 5 µg/mL) and assayed as described in table 5. The monkeys were injected i.m. with 1 mg of either pCVTat (M9-M11) or pCV0 (M12, control).
ND, not determined.

Anti-Tat CTLs were detected at week 32 post-immunization (Table 28).

TABLE 28

Analysis of the anti-Tat cytotoxic activity (CTLs)[a]

| Monkey | Week | Target:Effector ratio ||||| CTL Activity |
|---|---|---|---|---|---|---|---|
| | | 1:50 | 1:25 | 1:12.5 | 1:6.25 | 1:3.125 | Media | |
| M9 | 32 | 0 | 0 | 0 | 0 | 0 | 0 | − |
| | 50 | 4.2 | 0 | 0 | 0 | 0.9 | 1 | − |
| M10 | 32 | 0 | 0 | 9.9 | 2.7 | 0 | 2.5 | − |
| | 50 | 3.5 | 0 | 2.3 | 0 | 0 | 1.1 | − |
| M11 | 32 | 0 | 10.5 | 8.9 | 3.5 | 0.9 | 4.7 | + |
| | 50 | 0 | 0 | 0 | 3.8 | 0.3 | 0.8 | − |
| M12 | 32 | 0 | 0 | 0 | 0 | 0 | 0 | − |
| | 50 | 0 | 0 | 0 | 0 | 0 | 0 | − |

[a]The assay was performed as described in Table 6. The macaques were injected i.m. with 1 mg of either pCVTat (M9-M11) or pCV0 (M12, control).

PBMCs obtained from the monkey M11 at week 44 resulted resistent to in vitro infection with serial dilutions of the chimeric SHIV-89.6P virus by an assay described previously that detects the presence of total antiviral activity (TAA). In fact, TAA is evaluated as the capability of PBMCs from monkeys vaccinated with pCVTat-DNA, grown in the presence of autologous serum, to resist to the infection with serial virus dilutions. (Table 29)

TABLE 29

Analysis of the total antiviral activity (TAA)

| | Days post infection ||
|---|---|---|
| | 7 | 17 |
| Monkey | Minimum infectious dose (TCID$_{50}$/cell) | Minimum infectious dose (TCID$_{50}$/cell) |
| M9 | $10^{-2}$ | >$10^{-2}$** |
| M10 | $10^{-3}$ | $10^{-2}$ |
| M11 | >$10^{-2}$* | >$10^{-2}$* |
| M12 | $10^{-2}$ | >$10^{-2}$** |

[a]The assay was performed as described in Table 13. The macaques were injected i.m. with 1 mg of either pCVTat (M9-M11) or pCV0 (M12, control). PBMCs were withdrawn at week 44 from the first immunization and infected in vitro with $10^{-2}$, $10^{-3}$, $10^{-4}$, $10^{-5}$ TCID$_{50}$ of the SHIV-89.6P. The results are expressed as the minimum infectious dose of the SHIV (TCID$_{50}$/cell) still able to infect the cells.
*No culture resulted infected at the highest SHIV concentration used in the assay ($10^{-2}$ TCID$_{50}$/cell).
**The cultures became negative on day 17 post-infection.

The results shown in table 30 demonstrate the presence of the soluble antiviral activity (CAF) mediated by the CD8+ T lymphocytes in the vaccinated monkeys and in the control monkey (M12) injected with the empty vector (pCV0).

TABLE 30

Analysis of the soluble antiviral activity (CAF) mediated by the CD8+ T lymphocytes (CAF)[a]

| Monkey | Weeks from the primary immunization | % inhibition of viral replication ||
|---|---|---|---|
| | | Acute infection | Chronic infection |
| M9 | 0 | 21 | 14.6 |
| | 36 | 77 | 2.6 |
| M10 | 0 | 40 | 13.8 |
| | 36 | 67 | 25 |
| M11 | 0 | 49 | 19 |
| | 36 | 42 | 14 |
| M12 | 0 | 65 | 23 |
| | 36 | 62 | 14 |

[a]Analysis of the presence of the soluble antiviral activity mediated by the CD8+ T lymphocytes (CAF). PBMCs were obtained from the three monkeys (M9-M11) injected with 1 mg of pCVTat and from the control monkey (M12) inoculated with 1 mg of pCV0. The acute infection assay was carried out in CEM x 174 cells infected with the SHIV-89.6P, as described in Table 14. The chronic infection assay was carried out in U1 cells chronically infected with the HIV-1, as described in Table 14. The results are expressed as the percentage (%) of inhibition of viral replication in cells cultured in the presence or in the absence (control) of 5 µL of supernatants from CD8+ T cells.

The production of cytokines (γIFN, IL-4, TNFα) and of the chemokine RANTES was evaluated at week 44 in PBMCs from both the vaccinated and control monkeys (Table 31).

TABLE 31

Analysis of the production of cytokines and of RANTES[a]

| Monkey | Control | | | | PHA | | | | TT | | | |
|---|---|---|---|---|---|---|---|---|---|---|---|---|
| | γIFN | IL-4 | TNFα | RANTES | γIFN | IL-4 | TNFα | RANTES | γIFN | IL-4 | TNFα | RANTES |
| M9 | —/— | —/3.5 | —/— | —/— | 312/204 | —/— | 250/— | 536/2288 | —/— | —/— | —/— | nd/nd |
| M10 | nd/nd | nd/nd | nd/nd | nd/nd | nd/nd | Nd/nd | nd/nd | nd/nd | nd/nd | nd/nd | nd/nd | nd/nd |
| M11 | —/— | —/— | —/— | —/— | 420/183 | —/— | 388/— | 4336/3124 | —/— | —/— | —/nd | nd/nd |
| M12 | —/— | —/3.2 | —/— | —/— | 430/932 | —/— | —/— | 1936/2576 | —/— | —/— | 218/nd | nd/nd |

| Monkey | Tat (1 µg) | | | | Tat (5 µg) | | | |
|---|---|---|---|---|---|---|---|---|
| | γIFN | IL-4 | TNFα | RANTES | γIFN | IL-4 | TNFα | RANTES |
| M9 | —/— | —/— | —/— | —/— | —/— | —/— | —/— | —/— |
| M10 | nd/nd | nd/nd | nd/nd | nd/nd | nd/nd | nd/nd | nd/nd | nd/nd |
| M11 | —/— | —/4 | —/— | 544/368 | —/— | —/3.5 | —/— | 2124/— |
| M12 | —/— | —/— | —/— | —/— | —/— | —/— | —/— | —/— |

[a]The assay was performed as described in Table 15. The macaques were injected i.m. with 1 mg of either pCVTat (M9-M11) or pCV0 (M12, control). PBMCs were withdrawn at week 44 after the first immunization. Results are shown as pg/ml of cytokines and RANTES detected at 48 and 96 hours (48/96) respectively.
(—), the values were below the cut-off value.
The cut-off values (pg/ml) were:
γIFN: 31.2; IL-4: 3.12;
TNF-a: 15.6;
RANTES: 62.5.
ND: not done.

The results show the presence of a weak reactivity to the skin tests with Tat in one monkey (M9) at week 11 (Table 32)

TABLE 32

Skin test to Tat[a]

| | Weeks from the primary immunization | | | | | | |
|---|---|---|---|---|---|---|---|
| Monkey | 11 | 15 | 21 | 28 | 32 | 36 | 44 |
| M9 | +/− | − | − | − | − | − | − |
| M10 | − | − | − | − | − | − | − |
| M11 | − | − | − | − | − | − | − |
| M12 | ND | ND | ND | ND | ND | ND | ND |

[a]Tat (1 and 5 µg) in 150 µL of PBS-A, 0.1% BSA or the buffer alone (control) were inoculated i.d. in a previously thrichotomized area of the upper back of the vaccinated animals but not in the control monkeys at weeks 11, 15, 21, 28, 32, 36, and 44 from the initial immunization. The macaques were injected i.m. with 1 mg of either pCVTat (M9-M11) or pCV0 (M12, control). The appearance, 48 to 72 hours later, of an erythematosus nodule indicated the presence of delayed-type hypersensitivity (DTH): ++, φ ≧ mm; ±, φ 1-4 mm; ±, erythema without hardening: −, φ < 1 mm.

The post-challenge results indicate that all the vaccinated animals were protected from the infection with 10 MID$_{50}$ of the SHIV-89:6 P, as indicated by the virological tests (plasma antigenemia, determination of the proviral DNA copy number, cytoviremia) that were all negative (Table 33). Moreover, the presence of anti-SIV antibodies in the monkey M11 indicated the exposure to the virus or an abortive infection. On the contrary, they were not detected in the remaining monkeys, therefore we decided to carry out the in vitro antibody production assay (IVAP) as well as the lymphoproliferative response to SIV antigens. These assays are ongoing and preliminary data indicate the presence of anti-HIV Env antibodies in all the DNA-inoculated monkeys. The macaques will be inoculated with a higher dose of the virus, since even the control animal M12 resulted resistant to infection. This monkey had been vaccinated with the empty vector pCV0. Recent data from the literature have demonstrated the adjuvant role played by certain DNA sequences that are much more frequent in bacteria than in eukaryotic cells, and that, similarly to LPS and mannose, represent a strong stimulus for the natural immunity (Ref. 179). Thus, it is conceivable that the protection observed in the monkey M12 may be due to the induction of a non-specific antiviral immunity by these bacterial sequences, such as the production of IFNα, IFNβ, IL-12, and IL-18, known to exert immuno modulant and antiviral functions. This is strongly suggested by the presence in this macaque of TAA (Table 29) and CAF (Table 30) antiviral activities in the absence of anti-Tat specific humoral and cellular immunity. In fact, these assays also measure non-antigen specific antiviral activities. The naive monkey M13, inoculated with a 3.5 fold lower virus dose than that injected in the macaque M12, resulted infected. These results confirm that 10 MID$_{50}$ challenge dose with which M12 monkey was inoculated were infectious (Table 33). On the basis of this result the inventor plans to utilize the pCV0 vector or parts of it as an adjuvant.

TABLE 33

| | Days post challenge with SHIV89.6P virus | | | | | | | | | | | |
|---|---|---|---|---|---|---|---|---|---|---|---|---|
| | 15 | | | | 30 | | | | 60 | | | |
| Monkey | p27[a] (pg/ml) | DNA PCR (copies/ µg)[b] | cyto-viremia[c] | Anti-SIV IgG[d] | p27 (pg/ml) | DNA PCR (copies/ µg) | cyto-viremia | Anti-SIV IgG | p27 (pg/ml) | DNA PCR (copies / µg) | Cyto-viremia | Anti-SIV IgG |
| M9 | <20 | <1 | Neg | Neg | <20 | <1 | Neg | Neg | <20 | <1 | Neg | Neg |
| M10 | <20 | <1 | Neg | Neg | <20 | <1 | Neg | Neg | <20 | <1 | Neg | Neg |
| M11 | <20 | <1 | Neg | 1:2 | <20 | <1 | Neg | 1:2 | <20 | <1 | Neg | Neg |

TABLE 33-continued

| | Days post challenge with SHIV89.6P virus | | | | | | | | | | | |
|---|---|---|---|---|---|---|---|---|---|---|---|---|
| | 15 | | | | 30 | | | | 60 | | | |
| Monkey | p27[a] (pg/ml) | DNA PCR (copies/ μg)[b] | cyto-viremia[c] | Anti-SIV IgG[d] | p27 (pg/ml) | DNA PCR (copies/ μg) | cyto-viremia | Anti-SIV IgG | p27 (pg/ml) | DNA PCR (copies / μg) | Cyto-viremia | Anti-SIV IgG |
| M12 | <20 | <1 | Neg | Neg | <20 | <1 | Neg | Neg | <20 | <1 | Neg | Neg |
| M13 | 1876 | +[f] | +[e] | ND | <20 | +[f] | ND | 1:1600 | <20 | 43 | ND | 1:3200 |

[a,b,c,d]The assays were performed as described in Table 17. The macaques were injected i.m. with 1 mg of either pCVTat (M9-M11) or pCV0 (M12, control). The monkey M13 was a naive animal infected with 2.85 MID$_{50}$ of SHIV89.6P.
[e]Viral isolation was performed in place of cytoviremia and resulted positive.
[f]DNA PCR was not quantitative and resulted positive.

FACS analysis of the CD4 and CD8 (Table 34) subsets confirmed the virological data.

In fact, a significant decline of the percentage and absolute number of the CD4 lymphocytes was observed at 15 and 60 days post-challenge only for the naive monkey M13, resulted infected as indicated by the positiveness of plasma antigenemia, proviral DNA, and virus isolation. (Table 33).

Example 6

Therapeutic Vaccine

A protocol of vaccination, based both on Tat-protein and Tat DNA, was made to evaluate the safety and toxicity of anti-Tat vaccine in already infected individuals. The experiment was performed on monkeys infected with decreasing

TABLE 34

FACS analysis of CD4 and CD8 lymphocytes.

| | Days post challenge with SHIV89.6P | | | | | | | | | | | |
|---|---|---|---|---|---|---|---|---|---|---|---|---|
| | 0 % (cells/μl) | | | 15 % (cells/μl) | | | 30 % (cells/μl) | | | 60 % (cells/μl) | | |
| Monkey | CD4+ | CD8+ | CD4+/CD8+ | CD4+ | CD8+ | CD4+/CD8+ | CD4+ | CD8+ | CD4+/CD8+ | CD4+ | CD8+ | CD4+/CD8+ |
| M9 | 21.5 (1500) | 37.6 (2630) | 0.57 | ND | ND | ND | 26.4 (1340) | 51.6 (2610) | 0.51 | 30.6 (2000) | 45.5 (2980) | 0.67 |
| M10 | 39.5 (1050) | 36.3 (960) | 1.1 | ND | ND | ND | 34.8 (1730) | 41.8 (2080) | 0.83 | 31.6 (3760) | 52.2 (6200) | 0.61 |
| M11 | 35.8 (1080) | 37.7 (1140) | 0.95 | ND | ND | ND | 28.7 (1330) | 36.7 (1710) | 0.78 | 24.5 (890) | 48.7 (1770) | 0.5 |
| M12 | 30.9 (1860) | 46 (2760) | 0.67 | ND | ND | ND | 26.7 (1300) | 49.6 (2420) | 0.54 | 23.7 (2620) | 52.1 (5760) | 0.45 |
| M13 | 40.5 (2590) | 39.7 (2544) | 1.01 | 38.4 (434) | 33.6 (380) | 1.14 | 35.1 (1721) | 32.2 (1479) | 1.16 | 3.1 (111) | 62.3 (2225) | 0.05 |

[a]The assay was performed as described in Table 18. The macaques were injected i.m. with 1 mg of either pCVTat (M9-M11) or pCV0 (M12, control). The monkey M13 was a naive animal infected with 2.85 MID$_{50}$ of SHIV89.6P.

These results demonstrate that the vaccination with the pCVTat plasmid was well tolerated and non-toxic and confirm those on the safety and tolerability of the DNA vaccination, obtained in the first pilot study. In addition, these data provide evidence that the pCVTat-DNA plasmid induces a specific humoral (although weaker than that induced by the Tat protein) and cellular immune response with antiviral effects, part of which may be due to particular DNA sequences present in the pCV0 vector that could function as adjuvants.

Immunization protocols that will include combinations of the DNA coding for other HIV-1 and cytokines genes described in the Example 3 will be evaluated. In these experiments SHIV containing the tat, rev, and nef genes of HIV will be used (Ref. 146, 85, 142, 65, 94, 129).

The pCV0 and pCVTat plasmids will be inoculated in the animals utilizing other delivery systems that may improve the immunization effectiveness, such as liposomes, nanoparticles, erythrocytes, gene gun delivery, or Tat DNA will be delivered through the utilization of herpes vectors as described in the prophetic Examples 9 and 10.

doses of SHIV89.6P and with immunodeficiency disease (AIDS). The viral stock used for the infection was obtained from spleen and lymph nodes of a cynomolgus monkey infected 14 days before. Lymphocytes, purified by mechanical separation, were divided into two aliquots ($1,5 \times 10^6$ cells/ml each). One aliquot was depleted of CD8+ T-cells by using immuno-magnetic beads (Dynal, Norway). Both cultures were stimulated with PHA (1 μg/ml) for three days and seeded at the concentration of $1 \times 10^6$ cells/ml in presence of 50 U/ml of IL-2. Viral replication was detected by the presence of reverse transcriptase (RT) in the culture medium harvested after three days. Before testing, the supernatant was clarified and ultracentrifuged at 100,000 rpm, for 11 minutes at +4° C. (Beckman TL-100 ultracentrifuge) and pellet was lysed. Thirty μl of the suspension were added to the reaction mix (TRIS HCl 1M, pH 8; $MgCl_2$, 0.5 M; KCl, 1M; Poly A 1 mg/ml; oligo-dT 12-18 100 μg/ml; DTT 0.02 M; 1,2 $^3$[H]-Methyl thymidine tri-phosphate 1mCi/ml) and incubated at 37° C. for 60 minutes. The reaction was stopped by adding 500 μl of Na Pyrophosphate 0.1 M pH5 and 600 μl of tri-chlor-acetic acid (TCA) 20% and the sample was spotted on a 0.45 μm filter (Millipore) and then read with a β-counter after the addition of 5 ml of scintillation cocktail (Filter Count, Packard).

Culture media containing more than 20,000 cpm were centrifuged and supplemented with 10% human serum AB. The virus was concentrated by ultra-centrifugation at 30,000 rpm (90 minutes at 4° C.), resuspended in RPMI 1640 containing 10% of human serum (AB group) and then stored in small aliquots in liquid nitrogen. The viral stock was titred in vitro on the human cell lines CEMx174 and C8166 ($3 \times 10^9$ $TCID_{50}$/cell), and in vivo on cynomolgus monkeys ($3.17 \times 10^{5.69}$ $MID_{50}$/ml).

A first pilot experiment has been performed on 7 monkeys infected i.v. with SHIV89.6P prepared as described above. Each monkey received 1 ml of SHIV diluted in saline buffer supplemented with 2% of human serum (AB, Rh-) according to the following protocol. One monkey (IM1) was inoculated with 1:500 of viral dilution; two monkeys (IM2, IM3) received the dilution 1:5,000; two monkeys (IM4, IM5) were inoculated with 1:50,000; the monkey IM6 received the 1:500,000 dilution; the last monkey (IM7) received 1:5,000,000 dilution. Each monkey was bleed at day 7 before infection with SHIV for determination of the basal parameters. Serum and plasma samples were frozen at −20° C. or −80° C. and then used to re-suspend the protein inoculum. At time 0 all monkeys were inoculated with SHIV89.6P. Monkeys were checked daily. Moreover, at day 0 and after 2 and 4 weeks they were bled and 10 ml of blood were used for hemato-chemical determinations (chemical-clinical analysis, electrolytes, white cells and platelets counts, hemoglobin) and virological and immunological analysis (i.e. plasma p27 Ag determination and viral load in plasma and cells). At week 4 post-infection, 6 monkeys (IM1-6) were infected. The monkey IM7, which received the lowest viral dilution (1:5,000,000) was SHIV-negative (Table 35).

after SHIV infection, and 1, 4, 5, 10, 11, 13, 14, 17, 18 weeks on. To evaluate the effects of this vaccination on disease progression, each macaque was daily checked for the presence or signs of disease and at time 0 and after 3, 8, 12, 16 and 21 weeks, 10 ml of blood were withdrawn for laboratory tests (chemical-clinical analysis, electrolytes, white cells and platelets counts, hemoglobin), for the evaluation of immunological status (presence of specific immunoglobulins, measure of Th1 and Th2 cytokines, chemokines production), for characterization of lymphocytes by FACS analysis (CD4, CD8, CD28, CD40, CD86, CD20, CD2, CD26 and CD20), and finally for evaluation of virological parameters (proviral DNA detection by semi-quantitative PCR, plasma viral load by competitive RT-PCR, plasma p27 Gag antigen by ELISA and presence of anti-SHIV Ab, as described previously). Other boosts will be made on the basis of the immunological, virological and clinical results.

After the last inoculum, monitoring will be scheduled monthly and at the appearance of clinical modifications. PBMC, sera, plasma and urine samples will be frozen at every time point for future tests as previously described.

The results already available from this experiment, obtained at week 8 after is immunization, are described. In both the vaccinated asymptomatic and control monkeys no signs of inflammation and neo-angiogenesis in the inoculation sites or general symptoms of disease were observed. No modifications of the clinical status were evident in the monkeys already symptomatic. Moreover, no activation of viral replication was detected. Taken together these results indicate

TABLE 35

Detection of the presence of SHIV89.6P in monkeys infected with serial viral dilutions

| | | Weeks post infection | | | | | |
|---|---|---|---|---|---|---|---|
| | | 0 | | 2 | | 4 | |
| Monkey | SHIV 89.6P dilution | Viral isolation[a] | p27 (pg/ml)[b] | Viral isolation | p27 (pg/ml)[b] | Viral isolation | p27 (pg/ml)[b] |
| IM1 | 1:500 | ND | ND | + | >450 | + | 47 |
| IM2 | 1:5.000 | ND | ND | + | >450 | + | 161.8 |
| IM3 | 1:5.000 | ND | ND | + | >450 | + | 6.67 |
| IM4 | 1:50.000 | ND | ND | + | <20 | + | >450 |
| IM5 | 1:50.000 | ND | ND | + | >450 | + | 166.7 |
| IM6 | 1:500.000 | ND | ND | + | >450 | + | 0 |
| IM7 | 1:5.000.000 | ND | ND | − | 0 | − | 0 |

[a]Virus isolation and
[b]plasma p27 Ag (pg/ml) were carried out as described in the legend to table 17. Monkeys were inoculated i.v. with serial dilutions of the virus stock, as described in text.

After 7 weeks from infection, all the animals showing serious immunodeficiency symptoms were vaccinated with both the Tat protein and DNA of the plasmid pCVTat according to the following protocol. Monkeys IM1, IM3, 1M5 and IM6 received the Tat protein (20 µg), dissolved in 250 µl of PBS-A supplemented with 0.1% BSA and 20% of autologous plasma and then added to 250 µl of Alum adjuvant. The protein inoculum was performed sub-cutaneously on a single site of monkey's upper back, whether the plasmid pCVTat (1 mg), resuspended in 1 ml of PBS-A, was injected i.m. in a different site in the back. Monkeys IM2 and IM4 (controls) were injected with 250 µl of Alum and 250 µl of PBS-A, 0.1% BSA 20% autologous plasma, s.c., in a site of the upper back and with pCV-0 (1 mg) resuspended in 1 ml of PBS-A, i.m., in a site in the upper back different from the previous one. The uninfected monkey IM7 was not vaccinated. The schedule of vaccination consisted of a time 0, corresponding to 7 weeks the absence of toxicity or increased viral replication in the monkeys vaccinated with a biologically active Tat protein or DNA (Table 36).

TABLE 36

Analysis of virological parameters

| | Weeks from the beginning of vaccination | | | | | |
|---|---|---|---|---|---|---|
| | 0 | | 3 | | 8 | |
| Monkey | p27 (pg/ml) | DNA PCR copies/µg | p27 (pg/ml) | DNA PCR Copies/µg | p27 (pg/ml) | DNA PCR Copies/µg |
| IM1 | 12.3 | 68 | 17.3 | 52 | 141 | 41 |
| IM3 | 0 | 61 | 0 | 48 | 0 | 71 |

TABLE 36-continued

Analysis of virological parameters

| | Weeks from the beginning of vaccination | | | | | |
|---|---|---|---|---|---|---|
| | 0 | | 3 | | 8 | |
| Monkey | p27 (pg/ml) | DNA PCR copies/μg | p27 (pg/ml) | DNA PCR Copies/μg | p27 (pg/ml) | DNA PCR Copies/μg |
| IM5 | 97.1 | 20 | 21.7 | 15 | 23.6 | 95 |
| IM6 | 0 | 43 | 0 | 55 | 0 | 24 |
| IM2 | 21.2 | ND | 36.6 | 53 | 27.4 | 78 |
| IM4 | 81 | 195 | 22 | 288 | 15.4 | 135 |
| IM7 | ND | ND | ND | ND | 0 | >1 |

The tests were performed as described in Table 17. Monkeys IM1, IM3, IM5 and IM6 were injected with Tat protein (20 μg) and Alum adjuvant s.c. and with pCVTat (1 mg) i.m. Monkeys IM2 and IM4 (infected controls) were injected with Alum adjuvant s.c. and pCV0 (1 mg) i.m. IM7 was an uninfected naive monkey. FACS analyses indicate that no modifications were observed in CD4+ and CD8+ T-lymphocytes after vaccination (Table 37).

tion degree was evaluated by FACS analysis and considered as acceptable if higher than 95%. The CD8-depleted cells (named CD8−PBMC) were grown in the presence of PHA (2 μg/ml) and IL-2 (40 U/ml) or immuno-magnetic beads previously coated with two monoclonal antibodies against the CD3 (Clone FN18, BioSource) and the CD28 (Clone 9.3) antigens (anti-CD3/28 beads). To improve the binding of anti-CD3/28 beads with target cells, the incubation was performed on a rotating wheel disposal. Then, the bound cells (named CD8−CD3+CD28+) were selected with a magnet and seeded in culture. Three times a week, cell concentrations were adjusted to the starting level and IL-2 was added where indicated; moreover, regarding the cells stimulated with anti-CD3/28 beads, preliminary results suggest that the continuous stimulation regimen coupled with a constant control of the bead:cell ratio, adjusted at every time point, is highly effective in the induction of the proliferative response. Our previous studies have shown that in the absence of exogenous IL-2, the CD8−CD3+CD28+ cell population proliferates better then CD8-PBMC stimulated with anti-CD3/28 beads. Moreover, the addition of exogenous IL-2 (40 U/ml, three

TABLE 37

FACS analysis of CD4+ and CD8+ lymphocytes

| | Time 0 % (cells/μl) | | | Weeks from beginning of vaccination | | | | | | | | |
|---|---|---|---|---|---|---|---|---|---|---|---|---|
| | | | | 0 % (cells/μl) | | | 3 % (cells/μl) | | | 8 % (cells/μl) | | |
| Monkey | CD4+ | CD8+ | CD4/CD8 | CD4+ | CD8+ | CD4/CD8 | CD4 | CD8 | CD4/CD8 | CD4 | CD8 | CD4/CD8 |
| IMI | 25.39 (1264) | 36.8 (1831) | 0.69 | 3.3 (101) | 64.16 (1963) | 0.05 | 2.32 (52) | 63.34 1431) | 0.04 | 3.41 (96) | 55.41 (1559) | 0.06 |
| IM3 | 19.26 (869) | 26.45 (1193) | 0.73 | 2.84 (74) | 58.22 (1526) | 0.05 | 3.21 (92) | 58.16 (1663) | 0.05 | 3.18 (91) | 50.12 (1434) | 0.06 |
| IM5 | 24.75 (580) | 58.04 (1361) | 0.42 | 2.28 (38) | 57.3 (946) | 0.04 | 2.89 (48) | 55.6 (917) | 0.05 | 2.15 (60) | 54.3 (1527) | 0.04 |
| IM6 | 40.46 (2590) | 39.74 (2544) | 1.01 | 3.12 (111) | 62.3 (2225) | 0.05 | 2.75 (138) | 65.40 (3290) | 0.04 | 2.3 (73) | 52.18 (1659) | 0.04 |
| IM2 | 42 (1787) | 34.7 (1476) | 1.21 | 2.41 (68) | 58.12 (1632) | 0.03 | 2.7 (121) | 57.6 (2580) | 0.05 | 1.89 (66) | 50.6 (1763) | 0.04 |
| IM4 | 30.72 (1589) | 27.76 (1680) | 1.10 | 2.12 (113) | 61.13 (3248) | 0.03 | 1.92 (90) | 60.3 (2828) | 0.03 | 3.12 (164) | 53.12 (2790) | 0.06 |
| IM7 | 17.02 (871) | 55.8 (2857) | 0.30 | ND | ND | ND | 20.26 (770) | 51.40 (1957) | 0.39 | 24.1 (868) | 50.43 (1842) | 0.48 |

FACS analysis was performed as described in the legend to Table 18. Monkeys IM1, IM3, IM5 and IM6 were injected with Tat protein (20 μg) and Alum adjuvant s.c. and with pCVTat (1 mg) i.m.. Monkeys IM2 and IM4 (infected controls) were injected with Alum adjuvant s.c. and pCV0 (1 mg) i.m.. IM7 was an uninfected naive monkey.

These data confirm that both Tat protein and pCVTat plasmid, at the used doses and inoculation routes, were well tolerated and without any toxic effect in the vaccinated monkeys and, moreover, they did not increase viral replication nor the CD4 T cell decline in infected animals.

Example 7

Co-Stimulation of Purified CD4+ Lymphocytes from SIV-Infected Monkeys, with Anti-CD3/28 Coated Beads Results in a Logarithmic Expansion of the Cell Number Without Significant Viral Replication and Transmission Peripheral blood mononuclear cells were depleted of CD8+ cell-population by using anti-CD8 immuno-magnetic beads (Dynal, Oslo; Dynabeads M-450 CD8). The purificatimes per week) significantly increases the kinetic of proliferation both in terms of number of cells and duration of effect (FIG. 14).

To evaluate the antiviral activity of this stimulation, CD8−CD3+CD28+ purified cells from 4 uninfected monkeys were infected at day 0 with 0.1 M.O.I. of SIV and then cultivated under continuous stimulation. CD8-PBMC stimulated with PHA and IL-2 were the control of the experiment. Viral infection was followed through detection of p27 Gag antigen in culture supernatant by a commercial ELISA (Coulter, Hialeah, Fla.). The p27 Gag antigen levels (ng/ml) were measured on day 6 and 12 after infection. As shown in FIG. 15, there is a significant difference in the infection in the two stimulation regimens. In fact, at day 6 after infection, the p27 antigen in the CD3/28 beads-stimulated cultures was 40% to 87% lower than cultures stimulated with PHA plus IL-2, and at day 12 this difference was increased in 2 out of 4 monkeys.

This suggests a reduction of viral infection susceptibility. In only one case (MK 9401) we observed a viral propagation in both stimulation regimens.

The results here described demonstrate that *Macaca fascicularis* is a good model for the ex vivo expansion of lymphocyte sub-population by anti-CD3/28 beads co-stimulation, without viral replication. This represents the rationale for the therapeutic vaccine we propose, based on expansion and re-infusion of autologous anti-viral specific lymphocytes, in HIV-infected individuals.

Example 8

Use of Dendritic Cells for Vaccination

Figure 16B:
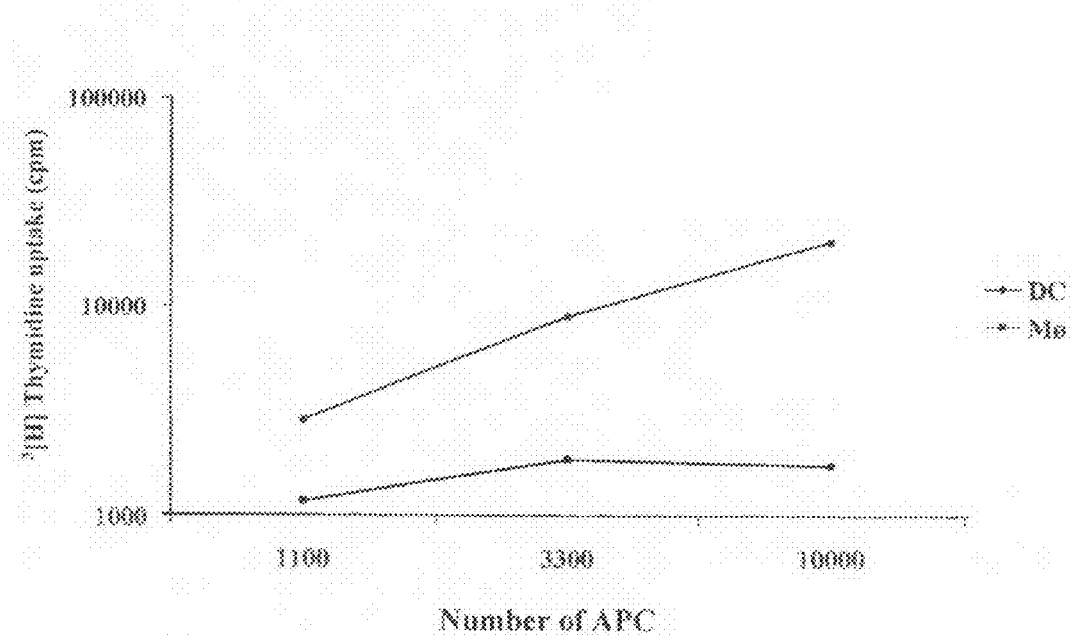
FIG. 16B. Functional characterization of dendritic cells obtained from monkey's peripheral blood. APCs, such as DC and Mø, obtained as reported in FIG. 16A, were challenged with T lymphocytes from another monkey.

The dendritic cells (DC) and macrophages, in a lesser extent, are able to efficaciously present antigens to the T lymphocytes and induce, in this cell subset, proliferation or acquisition of specific cytotoxic activities. These cells are named "antigen presenting cells" (APCs) and can start the immune response. Thus, DC may be utilized in ex vivo immunization protocols. For this reason, DC precursors were isolated from peripheral blood of *Macaca fascicularis* by culturing in vitro adherent cells after seven days of GM-CSF and IL-2 stimulation. Alternatively, CD34+ cells were purified with immuno-magnetic beads and then cultured in vitro with GM-CSF and TNF-α for 14 days. To confirm that DC were isolated, morphologic analysis and phenotypic characterization (FACS analysis and immuno-histochemistry) were performed. Functional analysis was based on the unique capability of DC to induce proliferation of allogeneic lymphocytes. The results obtained fully confirm the effectiveness of the purification and the functional characterization of DC. In details, to isolate DC precursors, PBMCs, obtained by Ficoll density gradient centrifugation, were again stratified on Percoll discontinuous gradient (50% and 42.5%). The cellular fraction that, after centrifugation at 500 g for 30 min, was between the two gradients was mainly constituted of monocytes (as confirmed by FACS analysis, data not shown). These cells were kept at 4° C. to avoid cell adhesion to the plastic tubes, then collected, washed, counted and seeded in culture at 37° C. The day after, non adherent cells were washed away with 4 gentle washings. To induce differentiation into DC, a complete medium supplemented with GM-CSF (200 ng/ml, Leucomax, Sandoz, Milan, Italy) and IL-4 (200 U/ml, Pepro tech, London, England) was added to adherent cells. As control, a complete medium without cytokines was added to induce the normal differentiation of monocytes in the macrophage lineage. Twice a week, half of the supernatant was replaced with fresh medium identical as that one utilized at day 0. The maturation of DC in the wells treated with cytokines was detected by typical morphological changes, like clustering, loss of adherence and development of cellular offshoots. The monocyte/macrophages adherent cells grown without cytokines were detached by EDTA treatment (0.5 mM in PBS-A), washed twice, counted and resuspended in fresh medium at different concentrations depending on the experiment performed. For the allogeneic mixed leukocyte reactions (AMLR), the obtained APCs (DC or macrophages) were tested with a fixed amount of allogeneic T lymphocytes, purified by Ficoll and Percoll gradients and adhesion, and then frozen. The AMLR was performed in 48-well plates with $0.5 \times 10^6$ T lymphocytes and serial dilutions of APCs. At day 4 of culture, a fixed amount of the cell suspension was seeded in a 96-well plate in triplicate. One µCi of $^3$H-tymidine was added to each well and the plate was then incubated at 37° C. for 16 hours. At the end of incubation, the amount of $^3$H-tymidine incorporated by the cells was measured with a β-counter and expressed as counts per minute (cpm). Results indicate that the DC obtained are potent APC as demonstrated by the higher induction of proliferation in allogeneic human lymphocytes compared to the macrophages stimulation, and by the capability to induce T lymphocyte proliferation in monkeys at all the concentrations used (FIG. 16B).

For the use in vaccination, DC will be resuspended at the concentration of $1 \times 10^5$ cells/100 µl in RPMI 1640 supplemented with 5% of autologous serum, 10 mM of Hepes buffer, 100 U/ml of penicillin-streptomycin, 0.5 mg/ml of amphotericin B and 0.03% of glutamine, and then incubated for 2 hours at 37° C. in presence of Tat protein or Tat-peptides or combination of Tat, Rev, Nef, Gag and/or cytokines. Then, this treated DC will be inoculated twice or more within 2-4 weeks from first injection, intravenously. Alternatively, DC will be transduced with tat-gene-containing vectors alone or associated with other vectors mentioned above and then injected intravenously.

Prophetic Example 9

The described immunogens will be utilized in order to induce and/or potentiate a specific immune response at the mucosa level. One of the approaches is based on the use bacteria (*S. Gordonii* and *Lactobacillus*) "engineered" to express the viral antigens mentioned above. These bacteria colonize the oral and vaginal mucosa of mice and induce a specific both local and systemic antibody response against heterologous antigens expressed on surface of recombinant bacteria (Ref. 116, 104, 106, 121, 117, 139, 105, 107). These bacteria can work as live vectors of vaccines and take the advantage to cause a prolonged stimulation of the immune system. Moreover, we will evaluate the possibility to co-express, on the bacterial surface, viral antigens and molecules involved in the immune response, such as the B sub-unit of the temperature-sensitive toxin of *E. Coli* or cytokines. The preparation of the recombinant strains of *S. Gordonii* will be carried out as previously described (Ref. 116). Briefly, (i) chromosomal integration of recombinant DNA molecules; (ii) transcriptional fusions with strong chromosomal promoters; (iii) transcriptional fusions with the gene coding for the protein M6, a surface protein of *Streptococcus*. The recombinant strains of *S. Gordonii* will be utilized to colonize the vaginal mucosa of the monkeys. It has been demonstrated that the recombinant strains of *S. Gordonii* which express the V3 region of gp120 of HIV-1 and the E7 protein of HPV-16, permanently colonize the vaginal mucosa of the mouse after a single inoculum, inducing an antigen-specific antibody response both local and systemic. The systemic response is in prevalence composed of IgG2a antibodies, which suggests a Th1-type response (Ref. 105, 106). We will select human vaginal strains of *Lactobacillus*, which are able to colonize the vaginal mucosa of the monkeys. Thereafter, an already developed genetic system will be utilized, which permits the expression of heterologous antigens on the surface of *Lactobacillus* (Rush, 1997). This strategy is based on: (i) cloning of genetic fusions (emm6/heterologous gene) into insertion vectors which carry homologies with the conjugative transposon Tn916; (ii) transformation of the vectors in bacterial strains which work as intermediate host (*Bacillus Subtilis*); (iii) conjugative mobilization of the recombinant transposons from *B. subtilis* to *Lactobacillus*. The recombinant strains of *Lactobacillus* will be utilized to colonize the vaginal mucosa of the monkeys.

Vaginal samples will be obtained utilizing special absorbent filters (Ref. 38, 105, 106). Colonization will be evaluated by plating the vaginal samples on selective plates and expression of HIV antigens in vivo will be monitored by immunofluorescence on vaginal swaps (Ref: 105). By using already standardized methods (Ref. 38), the vaginal swabs will be utilized for i) Papanicolau test, in the case of is vaginal vaccination; ii) presence of vaccine antigens in the cells; iii) phenotypic characterization of cells by cytofluorometric analysis (CD1, CD2, CD4, CD5, CD8, CD11c, CD14, CD20, CD28, CD40, CD25, HLA-DR); iv) evaluation of cytokine production (IL-2, IFNγ, TNFα, IL-4, IL-10, IL-15, semi-quantitative RT-PCR), determination of the presence of cytokines and 13-chemokines in the mucosal fluids, by Elisa assays; v) dosage of total and specific immunoglobulins (IgA and IgG) in the mucosal fluid by Elisa [Di Fabio et al., Vaccine 15: 1 (1997)]. One month after the last inoculum of the immunogen, the monkeys will be infected intravenously or through the mucosal route with the SHIV 89.6P. The follow-up of the monkeys will be carried out as described in the Example 4. Blood samples will be obtained in order to execute the routine laboratory exams, the evaluation of immunological parameters, both humoral and cellular, as described in the Example 4. The inventor believes that this method can be utilized successfully to induce specific immunization in monkeys, using the vaginal route. Alternatively, the mucosal immunity can be induced by administering the protein immunogens, above described, directly through the mucosal route in the presence of adjuvants, such as the thermo sensitive toxin of *E. Coli* and the choleric toxin, or utilizing other bacterial and non bacterial delivery systems, such as cytofectins and liposomes or through the inoculation by other routes which are able to induce the most efficient and protective immune response (Ref. 83, 81, 62).

Moreover, the inventor believes that recombinant herpes vectors, expressing the above described viral proteins, can be excellent systems to induce an effective mucosal immune response. Recombinant viral vectors from the herpes simplex type 1 virus (HSV-1) will be utilized to express viral proteins for the induction, of a systemic (through cutaneous immunization, i.d.) and mucosal (through the oral, vaginal or nasal route) responses. Non pathogenic, non replicative herpes vectors will be utilized (Ref. 99) for their ability to include large exogenous sequences, without interfering with the efficacy of the infection (Ref. 52, 64). Therefore, vectors able to contain more than one HIV gene (accessory, regulatory and structural) will be constructed. The mucosal immunity could be induced by an oral, vaginal or nasal vaccine. The herpes vectors can be used in these vaccinal approaches, since HSV-1 can be administered directly by the mucosal route (Ref. 176, 75). The recombinant viruses will be constructed utilizing a two-steps method which facilitates the insertion of exogenous sequences into the viral genome. The first step requires the insertion of an expression cassette with a reporter gene (β-galactosidase, LacZ) cloned in the restriction site PacI, which is not present in the HSV-1 genome, flanked by the wanted target sequence of HSV-1, using the standard procedure for the homologous recombination, to interrupt the HSV-1 gene. The recombinant virus is selected by formation of plaques with a blue phenotype, using "x-gal staining". The digestion of viral DNA with PacI releases the marker gene and generates two large fragments of viral DNA, not able to produce infectious viral particles. The second step consists of a co-transfection of the viral DNA, digested with the same plasmid used to create the deletion, where the reporter gene is substituted by the wanted gene. The recombinant viruses will be identified through the selection of plaques with a white phenotype after "x-gal staining". This recombination will lead to the elimination of PacI sites allowing the use of this method to insert many genes in different loci of HSV-1 genome (Ref. 74). By crossing the different vectors containing the single genes, we might be able to create all the different genetic combinations. The vector containing all the wanted genes will be isolated by screening with different markers, phenotypes and selective growth on competent cells. All the combinations will be created by alternating DNA transfections and viral recombinations.

Vectors expressing the single genes tat, rev, nef or gag will be constructed utilizing, as basic vector, that one containing the mutations in the genes 4-/22-/27-/41, that is better for the low toxicity and the strong expression of the exogenous gene, compared to the other HSV-1 not replicative vectors. Constitutive promoters will be used, such as those from HCMV (human cytomegalovirus immediate early promoter), or as ICP0 lep (infected cell protein immediate early promoter) and the Moloney Murine Leukemia virus LTR, for inducing the expression of the genes above mentioned. Non replicative HSV-1 vectors expressing HIV-proteins in different combinations will be constructed. The production of these viruses containing more different genes will be obtained by a genetic crossing over of the vectors containing the single genes described in the previous point. Double, triple and quadruple vectors will be created. The vectors will be inoculated in the monkeys i.d. or through mucosal (oral, vaginal or nasal) route with particular attention to this last type of administration (Ref. 176, 101, 102). Vaccination schedule consists of multiple inocula at different time points, which must be determined in relation to immunogen or the combination of immunogens. During immunization the animals will be monitored for the evaluation of hematochemical and immunological parameters as described in the Example 4. With methods already standardized vaginal samples will be obtained, that will be studied as previously described in this Example.

Prophetic Example 10

Delivery Systems

Tat (protein and/or DNA) alone or in combination (as described above) will be inoculated using new delivery systems, such as erythrocytes or nanoparticles. The delivery system involving the use of erythrocytes is based on the possibility to deliver the antigen bound on autologous erythrocytes. In fact erythrocytes, at the end of their life span (around 120 days in humans), are removed from the circulation by the macrophages, known to have the function of professional antigen presenting cells. This property can be used for vaccine strategies. Thus, antigens will be bound to the erythrocytes with a particular technique (Ref. 95, 96), that allows the preservation of the immunogenic properties of the antigen (Ref: 29,30). Through this procedure, biotinilation of erythrocytes can be performed in the absence of significative modification of their properties and life span (Ref. 95). Phagocytosis of old erythrocytes by macrophage cells will start an immune response. Antibodies opsonization of erythrocytes carrying the antigen will help antigen removal from circulation. The main advantages of this methodology are: to 1) small quantity of antigen needed to induce a humoral and cellular immune response, 2) long lasting immunization due to the lasting presence of antigens carried by the erythrocytes in the periphery, 3) adjuvant functions provided by the system itself.

In fact, it has been shown in animal studies that the administration of antigens is bound on the membrane of autologous erythrocytes induces a similar or higher immune response compared to the immune response obtained with the same antigen administered with Freund's adjuvant (Ref. 29). These properties are very useful to develop an anti-HIV vaccine, in particular when it is needed to increase the immunogenicity of the antigen and the antigen availability and when a low number of immunizations is required. In addition, this strategy can be used when no adjuvants are included in the vaccination protocol. In fact, it has been shown in the mouse model that antigens administered through autologous erythrocytes induce similar or higher immune responses compared to those obtained with the same antigen administered with Freund's adjuvant known as the most powerful adjuvant commercially available (Ref. 29), although not approved for human studies because of the important side effects. Thus, the adjuvant effect of erythrocytes carrying Tat protein, alone or in combination with other immunogens previously described, will be analyzed in non human primates. Comparison among these data and those obtained with the administration of Tat protein in the presence of Alum, RIBI or ISCOM will be performed.

The use of nanoparticles can represent an additional delivery strategy. Functional nanoparticles represent an important system for the transport and release of proteins and DNA (Ref. 27, 172). The nanospheres are colloid polymeric particles of different chemical composition, with a large range of diameter from 10 to 1000 nm. It is possible to adsorb different kind of substances on the surface or inside the nanospheres (oligonucleotides, drugs, proteins, peptides, DNA) that are then brought to the cytoplasm or to the nucleus of cells where they are slowly released. In addition, a small amount of the immunogen is needed to be delivered due to the characteristics of nanospheres. Nanoparticles are a good delivery system to especially for molecules with low stability in the extracellular environment or when the delivery is directed to a specific target cell.

The inventor believes that nanospheres can be used to deliver the viral antigens above described. It is possible to prepare and characterize three types of nanospheres designed for the delivery and controlled release of DNA (nanospheres type 1 and 2) and proteins (nanospheres type 3).

For the DNA delivery, two types of nanospheres (nanospheres type 1 and 2) are available. The first type of nanospheres (nanospheres type 1) has a triple layers structure with an external layer of poly-oxy-ethylen-glicole (PEG). Recent reports based on stealth systems studies (Ref. 180, 78), show that PEG makes nanospheres invisible to Kupfer cells. In contrast, the more internal layer is made of monomers with tensioactive features containing quaternary ammonium groups that reversibly adsorb the DNA through a mechanism of ionic exchange and an internal core made of methyl-metacrylate as monomer. These nanospheres are obtained by polymerization in microemulsion involving the polymerization of a vinilic or vinilidenic monomer in the presence of a mix of tensioactive reagents. These reagents are thus able to polymerize the monomer. Of these, one has a quaternary ammonium group interacting with oligonucleotides and the other one has a long chain of PEG.

The second type of DNA delivery system is made of functional nano and microspheres (nanospheres type 2) with hydrogel characteristics. These nanospheres should be made in the presence of DNA to trap it inside the delivery system. Nanospheres core-shell are needed to deliver proteins (nanospheres type 3). They are made by an internal core of poly-methyl-metacrylate and an external shell of hydrosoluble statistic copolymer of acrylic acid and methyl-metacrylate, known to have an high degree of affinity for proteins (Ref. 79, 80). This copolymer is commercially available (EUDRAGIT) and is obtained with different percentages of the two co-monomers. The preparation process leading to the manufacture of this second type of nanospheres involves the polymerization in dispersion. The synthesis involves the radical polymerization of a vinilic or vinilidenic monomer in the presence of EUDRAGIT having steric stabilizing functions. After nanospheres nucleation, the EUDRAGIT arranges outside the particles. Thus, modifying the concentration of the radical initiator, the ratio between the monomer and EUDRAGIT and the reaction time, numerous nanospheres samples are obtained with different morphologic and chemical characteristics.

Thus, it can be evaluated whether the delivery of Tat protein or Tat DNA by nanoparticles, alone or in combination with the immunogens mentioned above (either protein or DNA) will induce an immune response against HIV. In particular, the humoral or cellular-mediated immune responses will be evaluated and compared to those obtained with the not delivered immunogens in the monkey model.

The inventor believes that the information derived from these studies can be useful to develop an anti-HIV vaccine. In addition, the information derived from this experimental protocol will be transferred also to other vaccines studies, in particular to those studies dealing with low immunogenicity recombinant proteins or peptides. The possibility to develop a vaccine with only one administration will lead to enormous advantages in terms of efficacy of the vaccine and decrease of managing costs of vaccine programs.

REFERENCES

1. Agostini et al., Blood 90:1115 (1997)
2. Albini et al., Proc. Natl. Acad. Sci. USA 92:4838 (1995)
3. Allan et al., Science 230:813 (1985)
4. Antibodies—A laboratory manual, Eds. Harlow E., Lane D., Cold Spring Harbor Laboratory (1988)
5. Arya et al., Science 229:69 (1985)
6. Aryoshi et al., AIDS 9:555 (1995)
7. Audibert et al., Immunol. Today 14:281 (193)
8. Badolato et al., Blood 90:2804 (1997)
9. Barillari et al., J. Immunol. 149:3727 (1992)
10. Barillari et al., Proc. Natl. Acad. Sci. USA 90:7941 (1993)
11. Barillari et al., Proc. Natl. Acad. Sci. USA 149:3727 (1993)
12. Blomberg et al., J. Immunol. Methods 160:27-34 (1993)
13. Blomberg et al., J. Immunol. Methods 168:267-273 (1994)
14. Blomberg et al., J. Immunol. Methods 193: 199-206 (1996)
15. Bohan et al., Gene Expr. 2:391 (1992)
16. Bourgault et al., J. Virol. 66:75 (1992)
17. Boyer et al., Nature Med. 3:526 (1997)
18. Bruisten et al., J. Infect. Dis. 166:620 (1992)
19. Buseyne et al., J. Virol. 67:694 (1993)
20. Butera et al., J. Virol. 65:4645 (1991)
21. Butera et al., J. Virol. 68:2726 (1994)
22. Cafaro et al., AIDS Res. Hum. Retrov. 7:204 (1991)
23. Carrol et al, Science. 276: 273-276, (1997)
24. Carson et al., J. Clin. Invest. 99:937 (1997)
25. Chang et al., J. Biomed. Sci. 2:189 (1995)
26. Chang et al., AIDS 11: 1421 (1997)
27. Chavany et al., Phar. Res. 9: 441 (1994)
28. Chen et al., J. Immunol. 149:4060 (1992)
29. Chiarantini et al., Vaccine 15: 276 (1997)
30. Chiarantini e at., Clin. Diag. Lab. Immunol. 5: 235 (1998)
31. Chirmule et al., J. Virol. 69:492 (1995)

32. Choppin et al., J. Immunol. 147:569 (1991)
33. Corallini et al., Cancer Res. 53: 1 (1993)
34. Corallini et al., Cancer Res, 53: 5569 (1993)
35. Culman et al., J. Immunol. 146:1560 (1991)
36. Couillin et al., J. Exp. Med. 180:1129 (1994)
37. Danko et al., Vaccine 12:1499 (1994)
38. Di Fabio et al., Vaccine 15: 1 (1997)
39. Ensoli et al., IV International Conference on AIDS, Stockholm, 1:241 (1988)
40. Ensoli et al., Nature 345:84 (1990)
41. Ensoli et al., J. Virol. 67:277 (1993)
42. Ensoli et al., Nature 371:674 (1994)
43. Ensoli et al., AIDS Updates, Eds. V. De Vita, Jr., Hellman S., Rosenberg S. A., Lippincott J. B., Philadelphia; 7: 1 (1994)
44. Felber et al., Proc. Natl. Acad. Sci. 86:1495 (1989)
45. Fine et al., Ann. Plast. Surg. 20:6 (1988)
46. Fiorelli et al., J. Clin. Invest. 95:1723 (1995)
47. Folks et al., Science 238:800 (1987)
48. Franchini et al., Virology 155:593 (1986)
49. Frankel et al., Cell 55:1189 (1988)
50. Fugier-Vivier et al, J. Exp. Med. 186: 813 (1997)
51. Gait et al., Trends Biochem. Sci. 18:255 (1993)
52. Glorioso et al., Ann. Rev. Microbiol. 49:675 (1995)
53. Gobert et al., Virology 176:458 (1990)
54. Goletti et al., J. Virol. 69:2540 (1995)
55. Gorman et al., Mol. Cell. Biol. 2:1044 (1982)
56. Grabstein et al., Science 264:965 (1994)
57. Grosjean et al, J. Exp. Med. 186: 801 (1997)
58. Guy et al., Nature 330:266 (1987)
59. Harrer et al., AIDS Res. Hum. Retrov. 12:585 (1996)
60. Harrich et al., EMBO J. 16:6 (1997)
61. Hinkula et al., J. Virol. 71:5528 (1997)
62. Honenbang et al., Infect. Immun. 62:15 (1994)
63. Huang et al., EMBO J. 13:2886 (1994)
64. Huard et al. Gene Ther. 2:385 (1995)
65. Igarashi et al., AIDS Res. Hum. Retrov. 10:1021 (1994)
66. Jonuleit et al., J. Immunol. 158:2610 (1997)
67. Jullien et al., J. Immunol. 158:800 (1997)
68. Kanai et al., J. Immunol. 157:3681 (1996)
69. Karlosson et al., J. Virol. 71:4218 (1997)
70. Kashanchi et al., J. Virol. 70:5503 (1996)
71. Kestler et al., Science 248:1109 (1991)
72. Kim et al., Oncogene 7: 1525 (1992)
73. Koup et al., J. Virol. 68:4650 (1994)
74. Krisky et al., Gene Ther. 4:1120 (1997)
75. Kuklin et al., J. Virol. 240:245 (1998)
76. Landes, Austin, p. 107 (1997)
77. Lanzavecchia, Science 260: 937 (1993)
78. Lasic et al., Chemical Reviews 95: 2601 (1995)
79. Laus et al., Polymer 37: 343 (1996)
80. Laus et al., Polymers for Adv. Techn. 7: 548 (1996)
81. Lehnen et al., Vaccine Research 1:319 (1992)
82. Levine et al., Science. 272: 1939-1943 (1996)
83. Lewis et al., Vaccine Press, Ed. Robinson, Farrar, Wiblin; Human Press, Totowa, N.J. (1996)
84. Li et al., Proc. Natl. Acad. Sci. USA 94:8116 (1997)
85. Li et al., J. AIDS 5:639 (1992)
86. Li et al., Science 268:229 (1995)
87. Li et al., Proc. Natl. Acad. Sci. USA 94:8116 (1997)
88. Lippincott J. B., Stockholm, Sweden, May 31-Jun. 3 (1997)
89. Littaua et al., J. Virol. 65:40 (1991)
90. Lövgren et al., Vaccine 14:753 (1996)
91. Lu et al., J. Virol. 70:3978 (1996)
92. Lubaki et al., J. Infect. Dis. 175:1360 (1997)
93. Lucey et al., Clin. Diagn. Lab. Immunol. 4:43 (1997)
94. Luciw et al., Proc. Natl. Acad. Sci. 92:7490 (1995)
95. Magnani et al., Biotech. Appl. Biochem. 16: 188 (1992)
96. Magnani et al., Biotech. Appi. Biochem. 20: 335 (1994)
97. Malim et al., Nature 338:254 (1989)
98. Mann et al., EMBO J. 10:1733 (1991)
99. Marconi et al., Proc. Natl. Acad. Sci. 93:11319 (1996)
100. Marcuzzi et al., J. Virol. 66:4228 (1992)
101. McLean et al., J. Infect. Dis. 66:341 (1994)
102. McLean et al., Vaccine 14:987 (1996)
103. Mcfarland et al., J. Inf. Dis. 170:766 (1994)
104. Medaglini et al., Proc. Natl. Acad. Sci. USA 92: 6868 (1995)
105. Medaglini et al., Biotech. Annu. Rev. 3:297 (1997)
106. Medaglini et al., Vaccine 15:1330 (1997)
107. Medaglini et al., Am. J. Reprod. Immunol. 39:199 (1998)
108. Meyerhans et al., Cell 58:901 (1989)
109. Morein et al., AIDS Res. Hum. Retrov. S10:S109 (1994)
110. Molecular cloning A laboratory manual; Eds. Maniatis T., Fritsch E. F., Sambrook J., Cold Spring Harbor Laboratory, Cold Spring Harbor, N.Y. (1992)
111. Myers et al., Human Retroviruses and AIDS: A compilation and analysis of nucleic acid and amino acid sequences, Los Alamos Laboratory, Los Alamos, NM p. 1 (1993)
112. Myers et al., Human Retroviruses and AIDS. Theoretical Biology and Biophysics Group. Los Alamos, N.H. (1995)
113. Neuvet et al., J. Virol. 70:5572 (1996)
114. Nietfield et al., J. Immunol. 154:2189 (1995)
115. Nixon et al., Nature 336:484 (1988)
116. Oggioni et al., Vaccine 13:775 (1995)
117. Oggioni, et al., Gene 169:85 (1996)
118. O'Hagan et al., Novel Delivery Systems for Oral Vaccines, Eds. O'Hagan, D. T. CRC Press Boca Raton, Fla., p. 176 (1994)
119. Parslow, Human Retroviruses, Ed. B. R. Cullen, IRL press, Oxford, England, p. 101 (1993)
120. Pilkington et al., Mol. Immunol. 33:439 (1996)
121. Pozzi et al., in "Gram-positive bacteria as vaccine vehicles for mucosal immunization", eds. Pozzi G. & Wells, J. M. Landes, Austin, p. 35 (1997)
122. Puri et al., Cancer Res., 52:3787 (1992)
123. Puri et al., AIDS Res. 11:31 (1995)
124. Quesada-Rolander et al., ABS 6-S1, 2nd European Conference on Experimental AIDS Research, Stockholm, Sweeden, May 31-Jun. 3 (1997)
125. Quinn et al., Biochem. Biophys. Res. Commun. 239:6 (1997)
126. Ratner et al., Nature 313:277 (1985)
127. Re et al., J. Acquir. Immun. Defic. Syndr. 10:408 (1995)
128. Reimann et al., J. Virol. 70:3189 (1996)
129. Reimann et al., J. Virol. 70:6922 (1996)
130. Reiss et al., J. Med. Virol. 30:163 (1990)
131. Reiss et al., AIDS Res. Hum. Retrov. 5:621 (1989)
132. Riley et al, J. Immunol. 158: 5545-5553, (1997)
133. Rinaldo et al., AIDS Res. Hum. Retrov. 11:481 (1995)
134. Rinaldo et al., J. Virol., 69:5838 (1995)
135. Rodman et al., Proc. Natl. Acad. Sci. USA 90:7719 (1993)
136. Rodman et al., J. Exp. Med. 175:1247 (1992)
137. Rosenberg et al., Int. Immunol. 9 (5):703 (1997)
138. Rosenthal et al., Seminars in Immunology 9:303 (1997)
139. Rush, et al., in "Gram-positive bacteria as vaccine vehicles for mucosal immunization", eds. Pozzi G. & Wells, J. M. Landes, Austin, p. 107 (1997)
140. Sadaie et al., New Biol. 2:479 (1990)
141. Saiki et al., Science 230:1350 (1985)

142. Sakuragi et al., J. Gen. Virol. 73:2983 (1992)
143. Salter et al., Immunogenetics 21:235 (1985)
144. Schnorr et al, Proc. Natl. Acad. Sci. USA. 94: 5326 (1997)
145. Sharma et al., Biochem. Biophys. Res. Co. 208:704 (1995)
146. Shibata et al., J. Virol. 1.65:314 (1991)
147. Sipsas et al., J. Clin. Invest. 99:752 (1997)
148. Sodroski et al., Science 227:171, (1985)
149. Steinaa et al., Arch. Virol. 139:263 (1994)
150. Steinman R. M., Exp. Hematol. 24: 859 (1996)
151. Tahtinen et al., Virology 187:156 (1992)
152. Theoretical Biology and Biophysics, Los Alamos, N.H., (1995)
153. Titti et al., Cell. Pharmacol. AIDS 3:123 (1996)
154. Trinchieri, Curr. Opin. Hematol. 4:59 (1997)
155. van Baalen et al., J. Gen. Virol., 77:1659 (1996)
156. van Baalen et al., J. Gen. Virol. 78:1913 (1997)
157. Vellutini et al., AIDS Res. Hum. Retrov. 11:21 (1995)
158. Venet et al., J. Immunol. 148:2899 (1992)
159. Viscidi et al., Science 246:1606 (1989)
160. Vogel et al., Nature 335: 601 (1988)
161. Voss et al., Virology 208:770 (1995)
162. Wain-Hobson, Curr. Opin. Genet. Dev. 3:878 (1993)
163. Westendorp et al., J. Virol. 68:4177 (1994)
164. Westendorp et al., Nature 375:497 (1995)
165. Wolf et al., J. Immunol. 146:3074 (1991)
166. Yang et al., J. Virol. 70:4576 (1996)
167. Yang et al., J. Virol. 70:5799 (1996)
168. Yasutomi et al., J. Virol. 70:678 (1996)
169. Zauli et al., Blood 86:3823 (1995)
170. Zauli et al., Blood 80:3036 (1996)
171. Zauli et al., J. Immunol. 157:2216 (1996)
172. Zobel et al., Antisense Nucleic Acid Drug Dev. 7: 483 (1997)
173. Gibellini et al., Blood 89:1654 (1997)
174. Bauer et al., J. Infect. Dis. 165:419 (1992)
175. Klein et al., J. Exp. Med. 181:1365 (1995)
176. Bowen et al., Res. Virol. 143:269 (1992)
177. Zamarchi et al., AIDS Res. Human Retrov. 9:1139 (1993)
178. Fiore et al., AIDS 5:1034 (19912)
179. Roman et al., Nature Med. 3:849 (1997)
180. Allen et al., Biochim. Biophis. Acta 1237:99 (1995)

---

The invention claimed is:

1. A composition comprising: an isolated HIV Tat protein in combination with a pharmaceutically acceptable carrier or excipient, wherein said isolated HIV Tat protein is biologically active, as shown by (1) the ability of said isolated HIV Tat protein to activate virus replication when said isolated HIV Tat protein is added to HIV-1 infected cells, which ability to activate is determined by (A) the rescue of Tat-defective proviruses in HLM-1 cells after the addition of said isolated HIV Tat protein at a concentration of up to 1 μg/ml, or (B) the transactivation of HIV-1 gene expression in cells transfected with HIV-1 promoter-reporter plasmid after the addition of said isolated HIV Tat protein at a concentration of up to 1 μg/ml; and (2) the ability of said isolated HIV Tat protein to do one or both of the following (i) and (ii):
  (i) enter and localize in the nuclei of activated endothelial cells or dendritic cells, which entering and localizing is determined by (a) incubating activated endothelial cells or dendritic cells with up to 1 μg/ml of said isolated HIV Tat protein which is labeled with rhodamine, and (b) detecting the presence or absence of rhodamine in the activated endothelial cells or dendritic cells by fluorescence microscopy; or
  (ii) activate the proliferation, migration, and invasion of Kaposi's sarcoma (KS) cells or cytokine-activated endothelial cells in culture when said isolated HIV Tat protein is present at a concentration of up to 1 μg/ml,
  wherein said composition is pharmaceutically acceptable for administration to a human.

2. The composition of claim 1, wherein said isolated HIV Tat protein is purified.

3. The composition of claim 1, wherein said isolated HIV Tat protein is a wild type HIV Tat protein.

4. The composition of claim 1, 2 or 3, wherein the administration is selected from the group consisting of mucosal, nasal, oral, vaginal, rectal, intramuscular, subcutaneous, intradermal, systemic, and local administration.

5. The composition of claim 2, wherein said isolated HIV Tat protein is purified by a method comprising performing heparin affinity chromatography.

6. The composition of claim 5, wherein said performing step is followed by steps of (a) lyophilizing said isolated HIV Tat protein, and (b) resuspending said lyophilized isolated HIV Tat protein in a degassed buffer.

7. The composition of claim 1, 2 or 3 which further comprises a biologically acceptable fluid.

8. A product which is produced by a process comprising lyophilizing the composition of claim 1, 2 or 3.

9. A product which is produced by a process comprising lyophilizing the composition of claim 1, 2 or 3 and resuspending the lyophilized composition in a biologically acceptable fluid.

10. The composition of claim 3, wherein the amino acid sequence of said wild type HIV Tat protein consists of SEQ ID NO:2.

11. The composition of claim 7, wherein the biologically acceptable fluid is serum, plasma, or one or more fractions thereof.

12. The product of claim 9, wherein the biologically acceptable fluid is serum, plasma, or one or more fractions thereof.

13. The composition of claim 1, 2, 3, or 6 which further comprises an adjuvant.

14. The composition of claim 13 which further comprises a biologically acceptable fluid.

15. The composition of claim 13, wherein the adjuvant is RIBI, alum, or ISCOM, or a combination thereof.

16. The composition of claim 1, 2 or 3, wherein said isolated HIV Tat protein is bound to a delivery vehicle.

17. The composition of claim 16, wherein said delivery vehicle is a nanoparticle.

18. The composition of claim 16, wherein said delivery vehicle is an autologous erythrocyte.

19. The composition of claim 4, wherein the administration is systemic.

20. The composition of claim 4, wherein the administration is intradermal.

21. The composition of claim 4, wherein the administration is subcutaneous.

22. The composition of claim 4, wherein the administration is mucosal.

23. The composition of claim 13, wherein the administration is selected from the group consisting of mucosal, nasal, oral, vaginal, rectal, intramuscular, subcutaneous, intradermal, systemic, and local administration.

24. The composition of claim 23, wherein the administration is systemic.

25. The composition of claim 23, wherein the administration is intradermal.

26. The composition of claim 23, wherein the administration is subcutaneous.

27. The composition of claim 26 which further comprises Alum.

28. The composition of claim 23, wherein the administration is mucosal.

29. The composition of claim 1, 2, 3, or 4, wherein said isolated HIV Tat protein is conjugated to a T-helper peptide or T-helper universal epitope of Tetanus Toxoid.

30. The composition of claim 1, 2, 3 or 6, which further comprises HIV Rev, Nef or Gag, or an immunogenic fragment thereof.

31. The composition of claim 1, 2, 3, or 4, which further comprises an immuno-modulant cytokine.

32. The composition of claim 31, wherein said immuno-modulant cytokine is IL-12 or IL-15.

33. The composition of claim 1, 2, 3 or 6, wherein said isolated HIV Tat protein is fused to HIV Rev, Nef or Gag, or an immunogenic fragment thereof.

34. The composition of claim 1, 2, 3, or 4, wherein said isolated HIV Tat protein is fused to an immuno-modulant cytokine.

35. The composition of claim 34, wherein said immuno-modulant cytokine is IL-12 or IL-15.

36. The composition of claim 1, 2, 3, or 6, which further comprises an inhibitor of viral replication.

37. The composition of claim 1 which comprises a combination of said isolated HIV Tat protein.

38. The composition of claim 1 or 2 which is suitable for inducing an immune response in the human to said isolated HIV Tat protein.

39. The composition of claim 3, wherein said wild type HIV Tat protein is purified.

40. The composition of claim 10, wherein said wild type HIV Tat protein is purified.

41. The composition of claim 1, wherein said isolated HIV Tat protein is biologically active, as shown by (1) the ability of said isolated HIV Tat protein to activate virus replication when said isolated HIV Tat protein is added to HIV-1 infected cells, and (2) the ability of said isolated HIV Tat protein to enter and localize in the nuclei of activated endothelial cells or dendritic cells; which ability to activate is determined by (A) the rescue of Tat-defective proviruses in HLM-1 cells after the addition of said isolated HIV Tat protein at a concentration of up to 1 µg/ml, or (B) the transactivation of HIV-1 gene expression in cells transfected with a HIV-1 promoter-reporter plasmid after the addition of said isolated HIV Tat protein at a concentration of up to 1 µg/ml, and which ability to enter and localize is determined by (a) incubating activated endothelial cells or dendritic cells with up to 1 µg/ml of said isolated HIV Tat protein which is labeled with rhodamine, and (b) detecting the presence or absence of rhodamine in the activated endothelial cells or dendritic cells by fluorescence microscopy.

42. The composition of claim 41, wherein the isolated HIV Tat protein is a wild type HIV Tat protein.

43. The composition of claim 42, wherein said wild type HIV Tat protein is purified.

44. The composition of claim 42, wherein the amino acid sequence of said wild type HIV Tat protein consists of SEQ ID NO:2.

45. The composition of claim 44, wherein said wild type HIV Tat protein is purified.

46. The composition of claim 41, 42, 43, or 45 which further comprises an adjuvant.

47. The composition of claim 41, 42, 43, or 45, wherein the administration is intradermal.

48. The composition of claim 41, 42, 43, or 45, wherein the administration is subcutaneous.

49. The composition of claim 48 which further comprises Alum.

50. The composition of claim 1, wherein said isolated HIV Tat protein is biologically active, as shown by (1) the ability of said isolated HIV Tat protein to activate virus replication when said isolated HIV Tat protein is added to HIV-1 infected cells, which ability to activate is determined by (A) the rescue of Tat-defective proviruses in HLM-1 cells after the addition of said isolated HIV Tat protein at a concentration of up to 1 µg/ml, or (B) the transactivation of HIV-1 gene expression in cells transfected with a HIV-1 promoter-reporter plasmid after the addition of said isolated HIV Tat protein at a concentration of up to 1 µg/ml; and (2) the ability of said isolated HIV Tat protein to do both of the following (i) and (ii):

(i) enter and localize in the nuclei of activated endothelial cells or dendritic cells, which entering and localizing is determined by (a) incubating activated endothelial cells or dendritic cells with up to 1 µg/ml of said isolated HIV Tat protein which is labeled with rhodamine, and (b) detecting the presence or absence of rhodamine in the activated endothelial cells or dendritic cells by fluorescence microscopy; and (ii) activate the proliferation, migration, and invasion of Kaposi's sarcoma (KS) cells or cytokine-activated endothelial cells in culture when said isolated HIV Tat protein is present at a concentration of up to 1 µg/ml.

51. The composition of claim 50, wherein the isolated HIV Tat protein is a wild type HIV Tat protein.

52. The composition of claim 51, wherein said wild type HIV Tat protein is purified.

53. The composition of claim 51, wherein the amino acid sequence of said wild type HIV Tat protein consists of SEQ ID NO:2.

54. The composition of claim 53, wherein said wild type HIV Tat protein is purified.

55. The composition of claim 50, 51, 52, or 54 which further comprises an adjuvant.

56. The composition of claim 50, 51, 52, or 54, wherein the administration is intradermal.

57. The composition of claim 50, 51, 52, or 54, wherein the administration is subcutaneous.

58. The composition of claim 57 which further comprises Alum.

59. The composition of claim 1 or 2, wherein said isolated HIV Tat protein comprises the cysteine rich region of HIV Tat and is in a non-oxidated form.

60. The composition of claim 10, wherein said wild type HIV Tat protein is in a non-oxidated form.

61. The composition of any of claims 42-45, wherein said wild type HIV Tat protein is in a non-oxidated form.

62. The composition of any of claims 51-54, wherein said wild type HIV Tat protein is in a non-oxidated form.

63. A composition comprising: an isolated HIV Tat protein in combination with a pharmaceutically acceptable carrier or excipient, wherein said isolated HIV Tat protein is in a non-oxidated form, wherein said composition is pharmaceutically acceptable for administration to a human, and wherein the isolated HIV Tat protein is a wild type HIV Tat protein.

64. The composition of claim 63, wherein said wild type HIV Tat protein is purified.

65. The composition of claim 63, wherein the amino acid sequence of said wild type HIV Tat protein consists of SEQ ID NO:2.

66. The composition of claim 65, wherein said wild type HIV Tat protein is purified.

67. The composition of claim 63, 64, or 66 which further comprises an adjuvant.

68. The composition of claim 63, 64, or 66, wherein the administration is intradermal.

69. The composition of claim 63, 64, or 66, wherein the administration is subcutaneous.

70. The composition of claim 69 which further comprises Alum.

71. The composition of claim 63, wherein said isolated HIV Tat protein is conjugated to a T-helper peptide or T-helper universal epitope of Tetanus Toxoid.

72. The composition of claim 63, which further comprises HIV Rev, Nef or Gag, or an immunogenic fragment thereof.

73. The composition of claim 63, which further comprises an immuno-modulant cytokine.

74. The composition of claim 73, wherein said immuno-modulant cytokine is IL-12 or IL-15.

75. The composition of claim 1, wherein said isolated HIV Tat protein is biologically active, as shown by (1) the ability of said isolated HIV Tat protein to activate virus replication when said isolated HIV Tat protein is added to HIV-1 infected cells, and (2) the ability of said isolated HIV Tat protein to activate the proliferation, migration, and invasion of Kaposi's sarcoma (KS) cells or cytokine-activated endothelial cells in culture when said isolated HIV Tat protein is present at a concentration of up to 1 µg/ml; which ability to activate is determined by (A) the rescue of Tat-defective proviruses in HLM-1 cells after the addition of said isolated HIV Tat protein at a concentration of up to 1 µg/ml, or (B) the transactivation of HIV-1 gene expression in cells transfected with a HIV-1 promoter-reporter plasmid after the addition of said isolated HIV Tat protein at a concentration of up to 1 µg/ml.

76. The composition of claim 75, wherein the isolated HIV Tat protein is a wild type HIV Tat protein.

77. The composition of claim 76, wherein said wild type HIV Tat protein is purified.

78. The composition of claim 76, wherein the amino acid sequence of said wild type HIV Tat protein consists of SEQ ID NO:2.

79. The composition of claim 78, wherein said wild type HIV Tat protein is purified.

80. The composition of claim 75, 76, 77, or 79 which further comprises an adjuvant.

81. The composition of claim 75, 76, 77, or 79, wherein the administration is intradermal.

82. The composition of claim 75, 76, 77, or 79, wherein the administration is subcutaneous.

83. The composition of claim 82 which further comprises Alum.

* * * * *

SEQUENCE LISTING

<160> NUMBER OF SEQ ID NOS: 36

<210> SEQ ID NO 1
<211> LENGTH: 261
<212> TYPE: DNA
<213> ORGANISM: Human immunodeficiency virus
<220> FEATURE:
<221> NAME/KEY: CDS
<222> LOCATION: (1)...(261)
<223> OTHER INFORMATION: Wild-type HIV-1 Tat

<400> SEQUENCE: 1

```
atg gag cca gta gat cct aga cta gag ccc tgg aag cat cca gga agt      48
Met Glu Pro Val Asp Pro Arg Leu Glu Pro Trp Lys His Pro Gly Ser
 1               5                  10                  15 cag cct aaa act gct tgt acc aat tgc tat tgt aaa aag tgt tgc ttt      96
Gln Pro Lys Thr Ala Cys Thr Asn Cys Tyr Cys Lys Lys Cys Cys Phe
             20                  25                  30 cat tgc caa gtt tgt ttc ata aca aaa gcc tta ggc atc tcc tat ggc     144
His Cys Gln Val Cys Phe Ile Thr Lys Ala Leu Gly Ile Ser Tyr Gly
         35                  40                  45 agg aag aag cgg aga cag cga cga aga cct cct caa ggc agt cag act     192
Arg Lys Lys Arg Arg Gln Arg Arg Arg Pro Pro Gln Gly Ser Gln Thr
     50                  55                  60 cat caa gtt tct cta tca aag cag ccc acc tcc caa tcc cga ggg gac     240
His Gln Val Ser Leu Ser Lys Gln Pro Thr Ser Gln Ser Arg Gly Asp
 65                  70                  75                  80 ccg aca ggc ccg aag gaa tag                                         261
Pro Thr Gly Pro Lys Glu *
                 85
```

<210> SEQ ID NO 2
<211> LENGTH: 86
<212> TYPE: PRT
<213> ORGANISM: Human immunodeficiency virus
<220> FEATURE:
<223> OTHER INFORMATION: Wild-type HIV-1 Tat

<400> SEQUENCE: 2

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85

<210> SEQ ID NO 3
<211> LENGTH: 261
<212> TYPE: DNA
<213> ORGANISM: Artificial Sequence
<220> FEATURE:
<221> NAME/KEY: CDS
<222> LOCATION: (1)...(261)
<223> OTHER INFORMATION: HIV-1 Tat having an amino acid
      substitution at position 22 (changed from Cys to Gly)

<400> SEQUENCE: 3 atg gag cca gta gat cct aga cta gag ccc tgg aag cat cca gga agt     48
Met Glu Pro Val Asp Pro Arg Leu Glu Pro Trp Lys His Pro Gly Ser
1               5                   10                  15 cag cct aaa act gct ggt acc aat tgc tat tgt aaa aag tgt tgc ttt     96
Gln Pro Lys Thr Ala Gly Thr Asn Cys Tyr Cys Lys Lys Cys Cys Phe
            20                  25                  30 cat tgc caa gtt tgt ttc ata aca aaa gcc tta ggc atc tcc tat ggc    144
His Cys Gln Val Cys Phe Ile Thr Lys Ala Leu Gly Ile Ser Tyr Gly
        35                  40                  45 agg aag aag cgg aga cag cga cga aga cct cct caa ggc agt cag act    192
Arg Lys Lys Arg Arg Gln Arg Arg Pro Pro Gln Gly Ser Gln Thr
    50                  55                  60 cat caa gtt tct cta tca aag cag ccc acc tcc caa tcc cga ggg gac    240
His Gln Val Ser Leu Ser Lys Gln Pro Thr Ser Gln Ser Arg Gly Asp
65                  70                  75                  80 ccg aca ggc ccg aag gaa tag                                        261
Pro Thr Gly Pro Lys Glu *
                85

<210> SEQ ID NO 4
<211> LENGTH: 86
<212> TYPE: PRT
<213> ORGANISM: Artificial Sequence
<220> FEATURE:
<223> OTHER INFORMATION: HIV-1 Tat having an amino acid substitution
      at position 22 (changed from Cys to Gly)

<400> SEQUENCE: 4

Met Glu Pro Val Asp Pro Arg Leu Glu Pro Trp Lys His Pro Gly Ser
1               5                   10                  15

Gln Pro Lys Thr Ala Gly Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Arg Gly Asp
```

Pro Thr Gly Pro Lys Glu
            85

<210> SEQ ID NO 5
<211> LENGTH: 261
<212> TYPE: DNA
<213> ORGANISM: Artificial Sequence
<220> FEATURE:
<221> NAME/KEY: CDS
<222> LOCATION: (1)...(261)
<223> OTHER INFORMATION: HIV-1 Tat having an amino acid
      substitution at position 41 (changed from Lys to Thr)

<400> SEQUENCE: 5

```
atg gag cca gta gat cct aga cta gag ccc tgg aag cat cca gga agt      48
Met Glu Pro Val Asp Pro Arg Leu Glu Pro Trp Lys His Pro Gly Ser
 1               5                  10                  15 cag cct aaa act gct tgt acc aat tgc tat tgt aaa aag tgt tgc ttt      96
Gln Pro Lys Thr Ala Cys Thr Asn Cys Tyr Cys Lys Lys Cys Cys Phe
            20                  25                  30 cat tgc caa gtt tgt ttc ata aca aca gcc tta ggc atc tcc tat ggc     144
His Cys Gln Val Cys Phe Ile Thr Thr Ala Leu Gly Ile Ser Tyr Gly
        35                  40                  45 agg aag aag cgg aga cag cga cga aga cct cct caa ggc agt cag act     192
Arg Lys Lys Arg Arg Gln Arg Arg Arg Pro Pro Gln Gly Ser Gln Thr
    50                  55                  60 cat caa gtt tct cta tca aag cag ccc acc tcc caa tcc cga ggg gac     240
His Gln Val Ser Leu Ser Lys Gln Pro Thr Ser Gln Ser Arg Gly Asp
 65                 70                  75                  80 ccg aca ggc ccg aag gaa tag                                         261
Pro Thr Gly Pro Lys Glu *
            85
```

<210> SEQ ID NO 6
<211> LENGTH: 86
<212> TYPE: PRT
<213> ORGANISM: Artificial Sequence
<220> FEATURE:
<223> OTHER INFORMATION: HIV-1 Tat having an amino acid substitution at
      position 41 (changed from Lys to Thr)

<400> SEQUENCE: 6

Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Thr Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Arg Gly Asp
 65                 70                  75                  80

Pro Thr Gly Pro Lys Glu
            85

<210> SEQ ID NO 7
<211> LENGTH: 252
<212> TYPE: DNA
<213> ORGANISM: Artificial Sequence
<220> FEATURE:
<221> NAME/KEY: CDS
<222> LOCATION: (1)...(252)

<223> OTHER INFORMATION: HIV-1 Tat having a three-amino acid deletion at
      positions 78-80 (Arginine-Glycine-Aspartic acid (RGD))

<400> SEQUENCE: 7

```
atg gag cca gta gat cct aga cta gag ccc tgg aag cat cca gga agt        48
Met Glu Pro Val Asp Pro Arg Leu Glu Pro Trp Lys His Pro Gly Ser
1               5                   10                  15 cag cct aaa act gct tgt acc aat tgc tat tgt aaa aag tgt tgc ttt        96
Gln Pro Lys Thr Ala Cys Thr Asn Cys Tyr Cys Lys Lys Cys Cys Phe
            20                  25                  30 cat tgc caa gtt tgt ttc ata aca aaa gcc tta ggc atc tcc tat ggc       144
His Cys Gln Val Cys Phe Ile Thr Lys Ala Leu Gly Ile Ser Tyr Gly
        35                  40                  45 agg aag aag cgg aga cag cga cga aga cct cct caa ggc agt cag act       192
Arg Lys Lys Arg Arg Gln Arg Arg Pro Pro Gln Gly Ser Gln Thr
    50                  55                  60 cat caa gtt tct cta tca aag cag ccc acc tcc caa tcc ccg aca ggc       240
His Gln Val Ser Leu Ser Lys Gln Pro Thr Ser Gln Ser Pro Thr Gly
65                  70                  75                  80 ccg aag gaa tag                                                        252
Pro Lys Glu *
```

<210> SEQ ID NO 8
<211> LENGTH: 83
<212> TYPE: PRT
<213> ORGANISM: Artificial Sequence
<220> FEATURE:
<223> OTHER INFORMATION: HIV-1 Tat having a three-amino acid deletion at
      positions 78-80 (Arginine-Glycine-Aspartic acid (RGD))

<400> SEQUENCE: 8

```
Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
    50                  55                  60

His Gln Val Ser Leu Ser Lys Gln Pro Thr Ser Gln Ser Pro Thr Gly
65                  70                  75                  80

Pro Lys Glu
```

<210> SEQ ID NO 9
<211> LENGTH: 252
<212> TYPE: DNA
<213> ORGANISM: Artificial Sequence
<220> FEATURE:
<221> NAME/KEY: CDS
<222> LOCATION: (1)...(252)
<223> OTHER INFORMATION: HIV-1 Tat having a three-amino acid deletion at
      positions 78-80 (Arginine-Glycine-Aspartic acid (RGD)) and
      having an amino acid substitution at position 41 (from Lys to Thr)

<400> SEQUENCE: 9

```
atg gag cca gta gat cct aga cta gag ccc tgg aag cat cca gga agt        48
Met Glu Pro Val Asp Pro Arg Leu Glu Pro Trp Lys His Pro Gly Ser
1               5                   10                  15 cag cct aaa act gct tgt acc aat tgc tat tgt aaa aag tgt tgc ttt        96
Gln Pro Lys Thr Ala Cys Thr Asn Cys Tyr Cys Lys Lys Cys Cys Phe
            20                  25                  30 cat tgc caa gtt tgt ttc ata aca aca gcc tta ggc atc tcc tat ggc       144
His Cys Gln Val Cys Phe Ile Thr Thr Ala Leu Gly Ile Ser Tyr Gly
```

```
His Cys Gln Val Cys Phe Ile Thr Thr Ala Leu Gly Ile Ser Tyr Gly
        35                  40                  45 agg aag aag cgg aga cag cga cga aga cct cct caa ggc agt cag act    192
Arg Lys Lys Arg Arg Gln Arg Arg Arg Pro Pro Gln Gly Ser Gln Thr
    50                  55                  60 cat caa gtt tct cta tca aag cag ccc acc tcc caa tcc ccg aca ggc    240
His Gln Val Ser Leu Ser Lys Gln Pro Thr Ser Gln Ser Pro Thr Gly
65                  70                  75                  80 ccg aag gaa tag                                                    252
Pro Lys Glu *

<210> SEQ ID NO 10
<211> LENGTH: 83
<212> TYPE: PRT
<213> ORGANISM: Artificial Sequence
<220> FEATURE:
<223> OTHER INFORMATION: HIV-1 Tat having a three-amino acid deletion at
      positions 78-80 (Arginine-Glycine-Aspartic acid (RGD)) and having
      an amino acid substitution at position 41 (changed from Lys to
      Thr)

<400> SEQUENCE: 10

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Thr Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Pro Thr Gly
65                  70                  75                  80

Pro Lys Glu

<210> SEQ ID NO 11
<211> LENGTH: 20
<212> TYPE: PRT
<213> ORGANISM: Artificial Sequence
<220> FEATURE:
<223> OTHER INFORMATION: HIV-1 Tat peptide

<400> SEQUENCE: 11

Met Glu Pro Val Asp Pro Arg Leu Glu Pro Trp Lys His Pro Gly Ser
1               5                   10                  15

Gln Pro Lys Thr
            20

<210> SEQ ID NO 12
<211> LENGTH: 20
<212> TYPE: PRT
<213> ORGANISM: Artificial Sequence
<220> FEATURE:
<223> OTHER INFORMATION: HIV-1 Tat peptide

<400> SEQUENCE: 12

Ala Cys Thr Asn Cys Tyr Cys Lys Lys Cys Cys Phe His Cys Gln Val
1               5                   10                  15

Cys Phe Ile Thr
            20

<210> SEQ ID NO 13
<211> LENGTH: 16
```

```
<212> TYPE: PRT
<213> ORGANISM: Artificial Sequence
<220> FEATURE:
<223> OTHER INFORMATION: HIV-1 Tat peptide

<400> SEQUENCE: 13

Gln Val Cys Phe Ile Thr Lys Ala Leu Gly Ile Ser Tyr Gly Arg Lys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: HIV-1 Tat peptide

<400> SEQUENCE: 14

Ser Tyr Gly Arg Lys Lys Arg Arg Gln Arg Arg Pro Pro Gln
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: HIV-1 Tat peptide

<400> SEQUENCE: 15

Arg Pro Pro Gln Gly Ser Gln Thr His Gln Val Ser Leu Ser Lys Gln
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: HIV-1 Tat peptide

<400> SEQUENCE: 16

His Gln Val Ser Leu Ser Lys Gln Pro Thr Ser Gln Ser Arg Gly Asp
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: HIV-1 Tat peptide

<400> SEQUENCE: 17

Pro Thr Ser Gln Ser Arg Gly Asp Pro Thr Gly Pro Lys Glu
1               5                   10

<210> SEQ ID NO 18
<211> LENGTH: 15
<212> TYPE: DNA
<213> ORGANISM: Artificial Sequence
<220> FEATURE:
<223> OTHER INFORMATION: Forward primer Rev

<400> SEQUENCE: 18
atggcaggaa gaagc                                                          15

<210> SEQ ID NO 19
<211> LENGTH: 15
<212> TYPE: DNA
<213> ORGANISM: Artificial Sequence
```

```
<220> FEATURE:
<223> OTHER INFORMATION: Reverse primer Rev

<400> SEQUENCE: 19
ctattcttta gttcc                                                    15

<210> SEQ ID NO 20
<211> LENGTH: 15
<212> TYPE: DNA
<213> ORGANISM: Artificial Sequence
<220> FEATURE:
<223> OTHER INFORMATION: Forward primer Nef

<400> SEQUENCE: 20
atgggtggca agtgg                                                    15

<210> SEQ ID NO 21
<211> LENGTH: 15
<212> TYPE: DNA
<213> ORGANISM: Artificial Sequence
<220> FEATURE:
<223> OTHER INFORMATION: Reverse primer Nef

<400> SEQUENCE: 21
tcagcagtcc ttgta                                                    15

<210> SEQ ID NO 22
<211> LENGTH: 15
<212> TYPE: DNA
<213> ORGANISM: Artificial Sequence
<220> FEATURE:
<223> OTHER INFORMATION: Forward primer Gag

<400> SEQUENCE: 22
atgggtgcga gagcg                                                    15

<210> SEQ ID NO 23
<211> LENGTH: 15
<212> TYPE: DNA
<213> ORGANISM: Artificial Sequence
<220> FEATURE:
<223> OTHER INFORMATION: Reverse primer Gag

<400> SEQUENCE: 23
ttattgtgac gaggg                                                    15

<210> SEQ ID NO 24
<211> LENGTH: 15
<212> TYPE: DNA
<213> ORGANISM: Artificial Sequence
<220> FEATURE:
<223> OTHER INFORMATION: Forward primer IL-12

<400> SEQUENCE: 24
atgtggcccc ctggg                                                    15

<210> SEQ ID NO 25
<211> LENGTH: 15
<212> TYPE: DNA
<213> ORGANISM: Artificial Sequence
<220> FEATURE:
<223> OTHER INFORMATION: Reverse primer IL-12

<400> SEQUENCE: 25
ttaggaagca ttcag                                                    15
```

<210> SEQ ID NO 26
<211> LENGTH: 15
<212> TYPE: DNA
<213> ORGANISM: Artificial Sequence
<220> FEATURE:
<223> OTHER INFORMATION: Forward primer IL-15

<400> SEQUENCE: 26
atgagaattt cgaaa                                                          15

<210> SEQ ID NO 27
<211> LENGTH: 15
<212> TYPE: DNA
<213> ORGANISM: Artificial Sequence
<220> FEATURE:
<223> OTHER INFORMATION: Reverse primer IL-15

<400> SEQUENCE: 27
tcaagaagtg ttgat                                                          15

<210> SEQ ID NO 28
<211> LENGTH: 15
<212> TYPE: DNA
<213> ORGANISM: Artificial Sequence
<220> FEATURE:
<223> OTHER INFORMATION: Forward primer Tat

<400> SEQUENCE: 28
atggagccag tagat                                                          15

<210> SEQ ID NO 29
<211> LENGTH: 15
<212> TYPE: DNA
<213> ORGANISM: Artificial Sequence
<220> FEATURE:
<223> OTHER INFORMATION: Reverse primer Tat

<400> SEQUENCE: 29
ctattccttc gggcc                                                          15

<210> SEQ ID NO 30
<211> LENGTH: 27
<212> TYPE: DNA
<213> ORGANISM: Artificial Sequence
<220> FEATURE:
<223> OTHER INFORMATION: Forward primer Tat/Rev

<400> SEQUENCE: 30
ggcccgaagg aaatggcagg aagaagc                                             27

<210> SEQ ID NO 31
<211> LENGTH: 27
<212> TYPE: DNA
<213> ORGANISM: Artificial Sequence
<220> FEATURE:
<223> OTHER INFORMATION: Forward primer Tat/Nef

<400> SEQUENCE: 31
ggcccgaagg aaatgggtgg caagtgg                                             27

<210> SEQ ID NO 32
<211> LENGTH: 28
<212> TYPE: DNA
<213> ORGANISM: Artificial Sequence
<220> FEATURE:
<223> OTHER INFORMATION: Forward primer Tat/Gag

```
<400> SEQUENCE: 32
ggccctgaag gaaatgggtg cgagagcg                                              28

<210> SEQ ID NO 33
<211> LENGTH: 27
<212> TYPE: DNA
<213> ORGANISM: Artificial Sequence
<220> FEATURE:
<223> OTHER INFORMATION: Forward primer Tat/IL-12

<400> SEQUENCE: 33
ggcccgaagg aaatgtggcc ccctggg                                               27

<210> SEQ ID NO 34
<211> LENGTH: 27
<212> TYPE: DNA
<213> ORGANISM: Artificial Sequence
<220> FEATURE:
<223> OTHER INFORMATION: Forward primer Tat/IL-15

<400> SEQUENCE: 34
ggcccgaagg aaatgagaat ttcgaaa                                               27

<210> SEQ ID NO 35
<211> LENGTH: 24
<212> TYPE: DNA
<213> ORGANISM: Artificial Sequence
<220> FEATURE:
<223> OTHER INFORMATION: Primer SG1096Ngag

<400> SEQUENCE: 35
ttaggctacg acccggcgga aaga                                                  24

<210> SEQ ID NO 36
<211> LENGTH: 24
<212> TYPE: DNA
<213> ORGANISM: Artificial Sequence
<220> FEATURE:
<223> OTHER INFORMATION: Primer SG1592CgagD

<400> SEQUENCE: 36 ataggggtg cagccttctg acag                                                   24
```